(12) United States Patent
Shturman et al.

(10) Patent No.: US 6,494,890 B1
(45) Date of Patent: Dec. 17, 2002

(54) ECCENTRIC ROTATIONAL ATHERECTOMY DEVICE

(75) Inventors: Leonid Shturman, Minneapolis, MN (US); Andrei Nevzorov, Moscow (RU)

(73) Assignee: Shturman Cardiology Systems, Inc., Minneapolis, MN (US)

( * ) Notice: Subject to any disclaimer, the term of this patent is extended or adjusted under 35 U.S.C. 154(b) by 656 days.

(21) Appl. No.: 08/911,586

(22) Filed: Aug. 14, 1997

(51) Int. Cl.⁷ .............................................. A61B 17/22
(52) U.S. Cl. ...................................................... 606/159
(58) Field of Search .......................... 606/1, 159, 170, 606/180, 171; 604/22

(56) References Cited

U.S. PATENT DOCUMENTS

| | | | |
|---|---|---|---|
| 4,030,503 A | 6/1977 | Clark, III | 128/304 |
| 4,883,460 A | 11/1989 | Zanetti | 604/22 |
| 4,990,134 A | 2/1991 | Auth | 604/22 |
| 5,158,564 A | 10/1992 | Schnepp-Pesch et al. | 606/159 |
| 5,192,291 A | 3/1993 | Pannek, Jr. | 606/159 |
| 5,217,474 A | 6/1993 | Zacca et al. | |
| 5,308,354 A | 5/1994 | Zacca et al. | |
| 5,312,427 A | 5/1994 | Shturman | |
| 5,314,438 A | 5/1994 | Shturman | 606/159 |
| 5,356,418 A | 10/1994 | Shturman | |
| 5,358,485 A | 10/1994 | Vance et al. | 604/22 |
| 5,360,432 A | 11/1994 | Shturman | |
| 5,395,311 A | 3/1995 | Andrews | 604/22 |
| 5,490,859 A | 2/1996 | Mische et al. | 606/159 |
| 5,501,694 A | 3/1996 | Ressemann et al. | |
| 5,554,163 A | 9/1996 | Shturman | |

FOREIGN PATENT DOCUMENTS

| | | | | |
|---|---|---|---|---|
| DE | 91 06 690.5 | 8/1991 | .......... | A61M/29/00 |
| EP | 0 421 457 B1 | 4/1991 | | |
| RU | 2055991 C1 | 10/1996 | .......... | F01D/15/06 |
| WO | WO 94/08519 | 4/1994 | .......... | A61B/17/32 |
| WO | WO 94/09709 | 5/1994 | .......... | A61B/17/32 |

*Primary Examiner*—Michael J. Milano
(74) *Attorney, Agent, or Firm*—Perman & Green, LLP

(57) ABSTRACT

A rotational atherectomy device having a flexible, elongated, rotatable drive shaft with an eccentric enlarged diameter section. At least part of the eccentric enlarged diameter section has a tissue removing surface. The eccentric enlarged diameter section of the drive shaft has a center of mass and/or geometric center spaced radially from the rotational axis of the drive shaft, facilitating the ability of the device to open the stenotic lesion to a diameter substantially larger than the outer diameter of the enlarged diameter section.

106 Claims, 54 Drawing Sheets

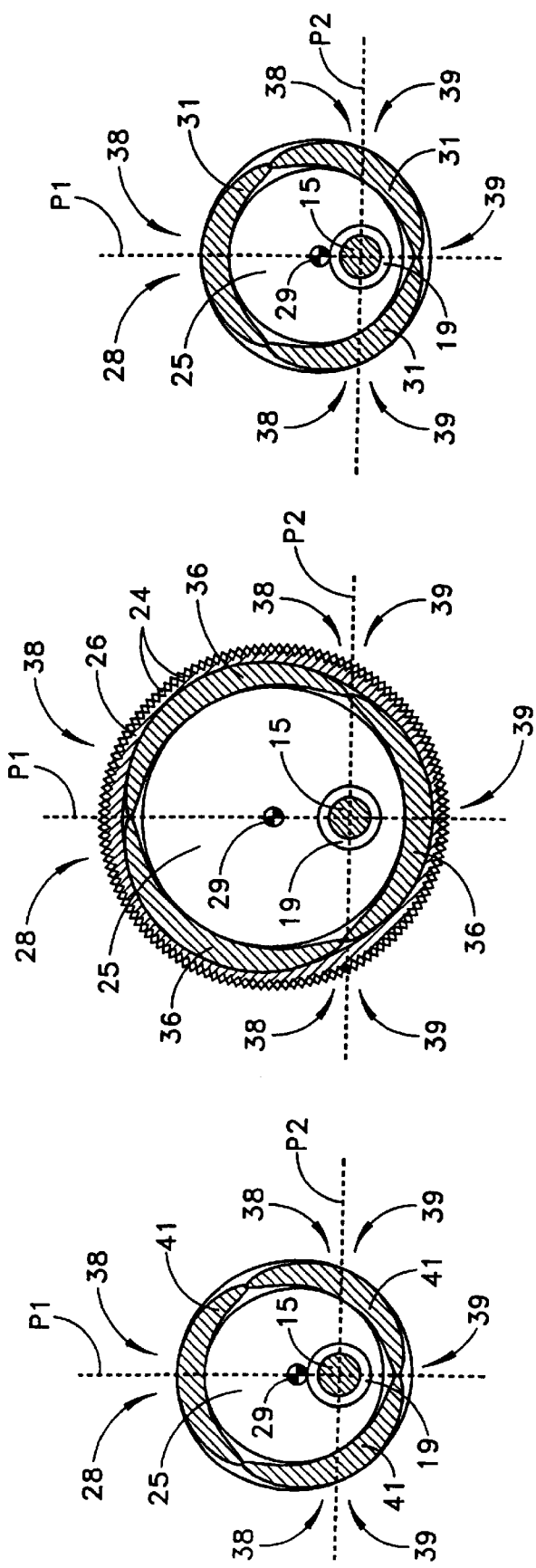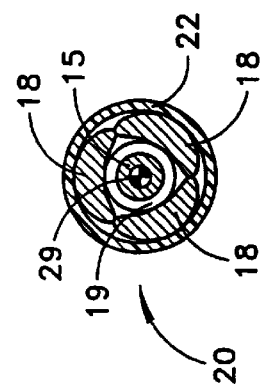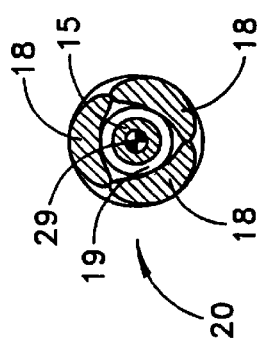
FIG. 3C
FIG. 3B
FIG. 3A
FIG. 3E
FIG. 3D

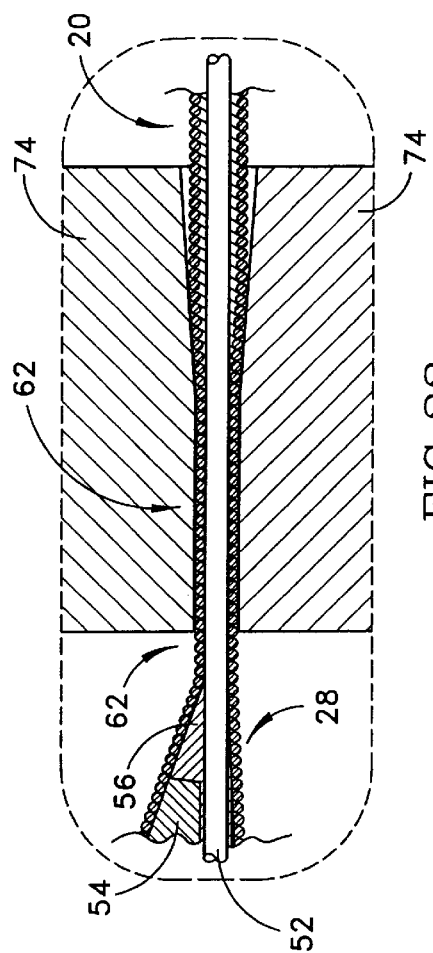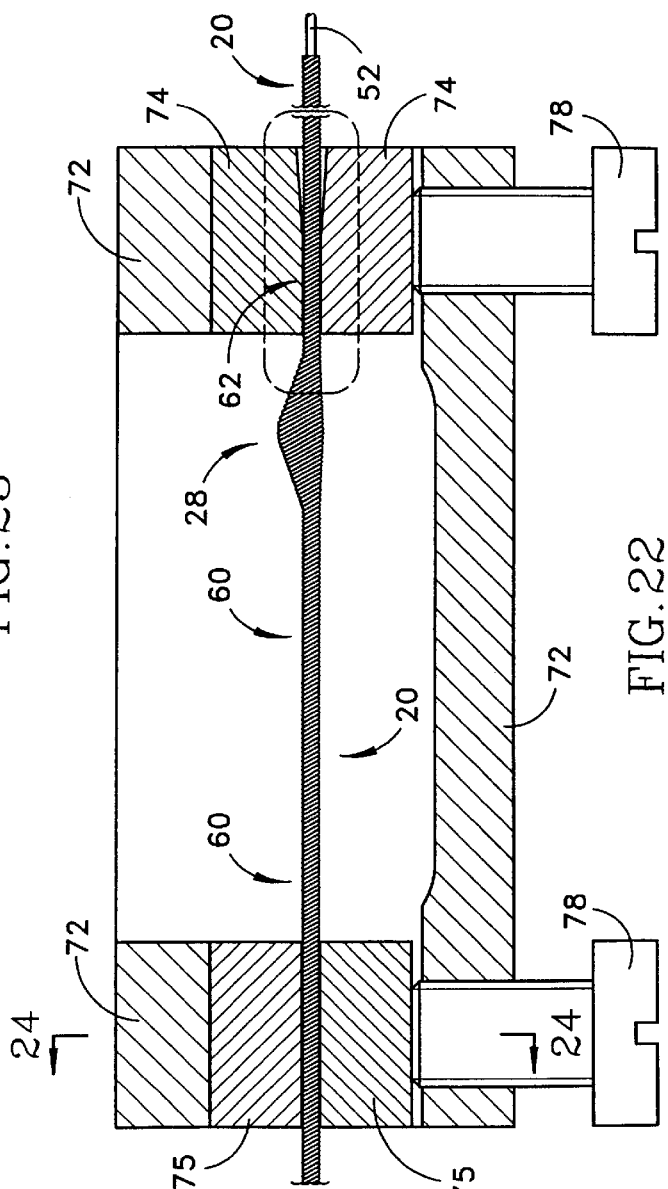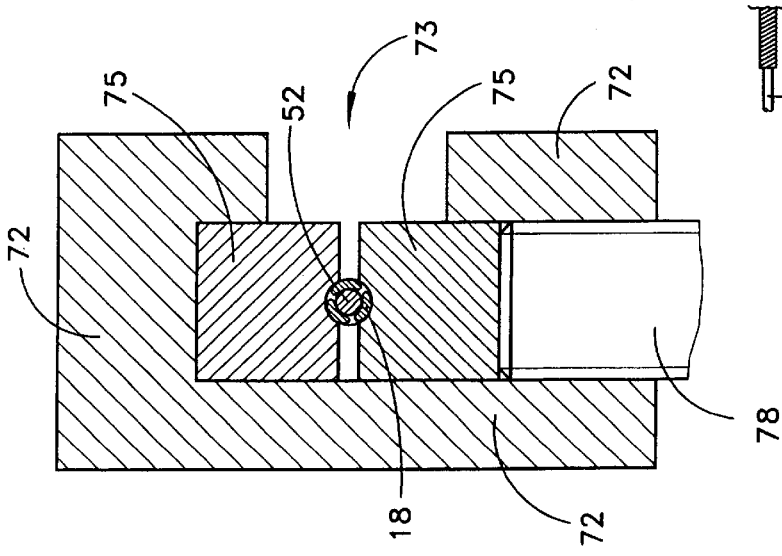

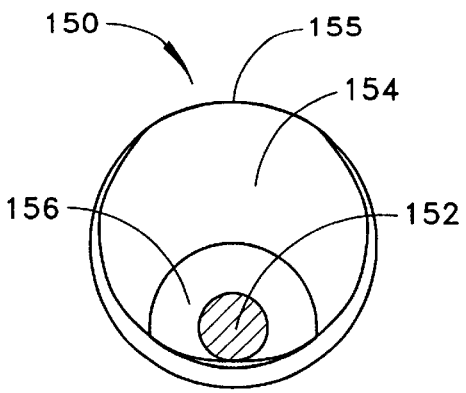
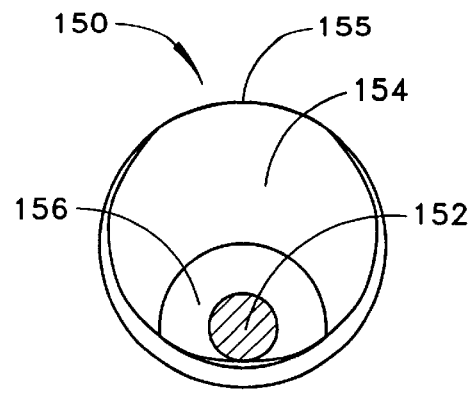
FIG.26A     FIG.26B
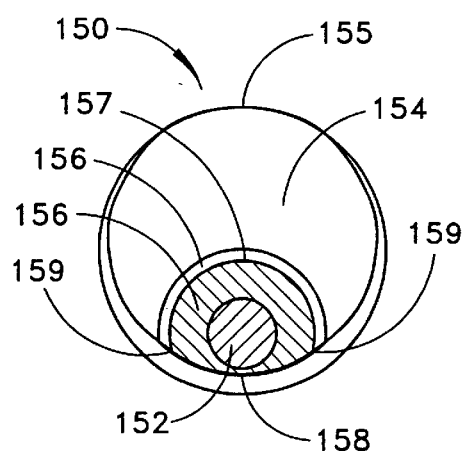
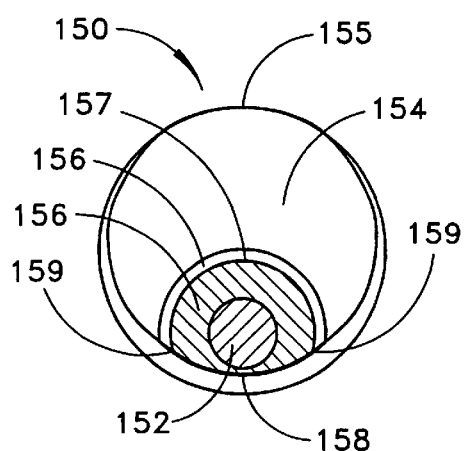
FIG.26C     FIG.26D
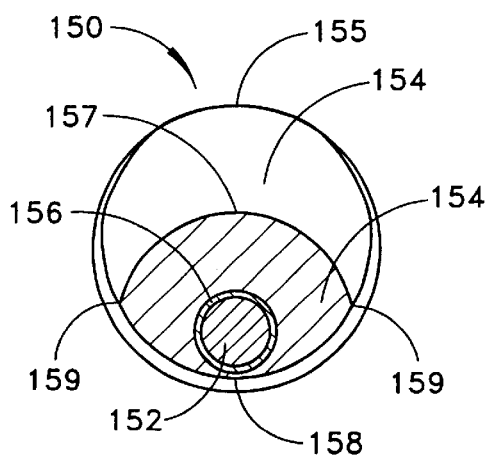
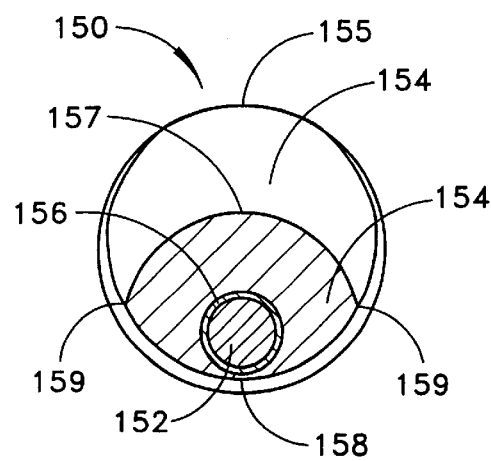
FIG.26E     FIG.26F

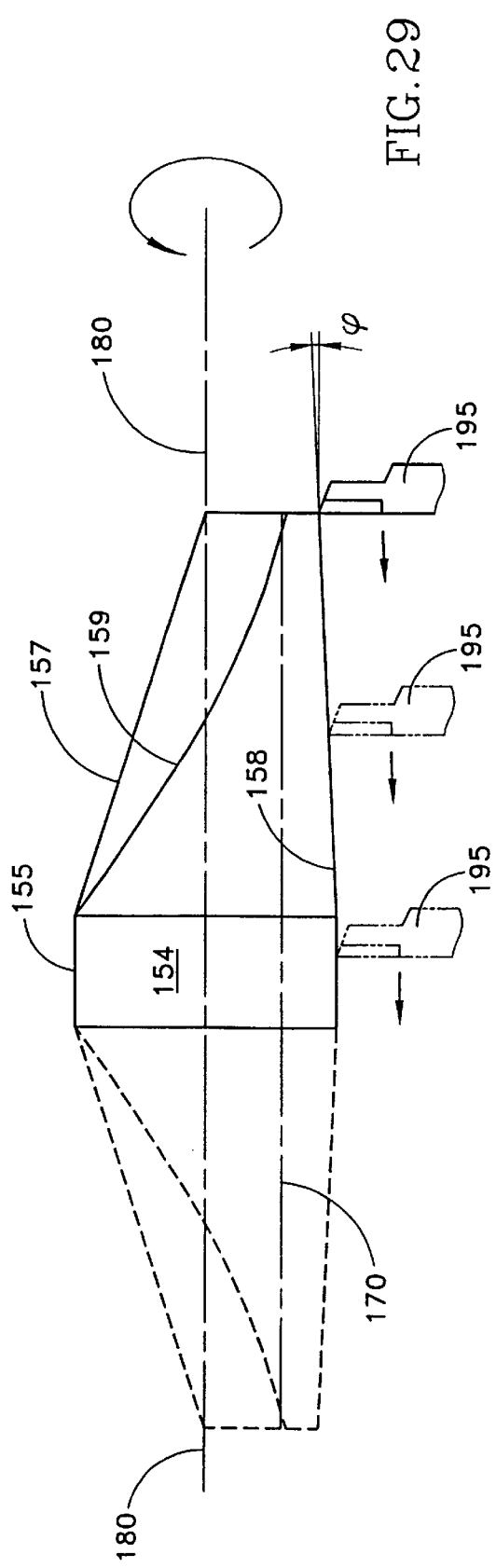
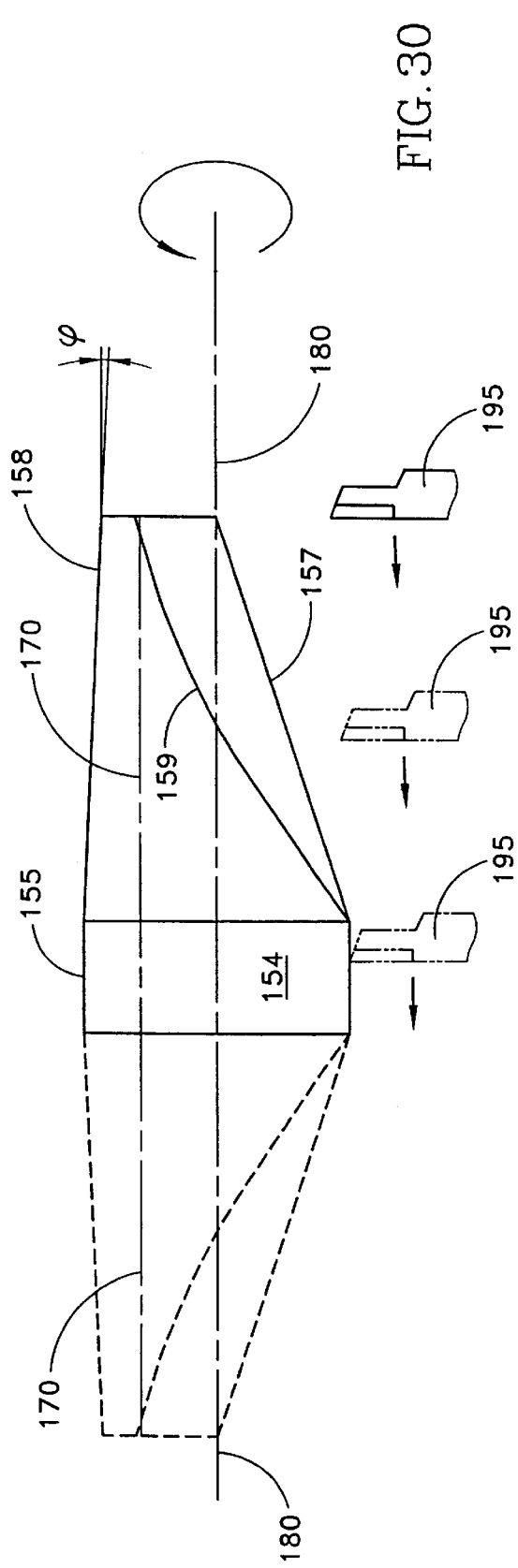

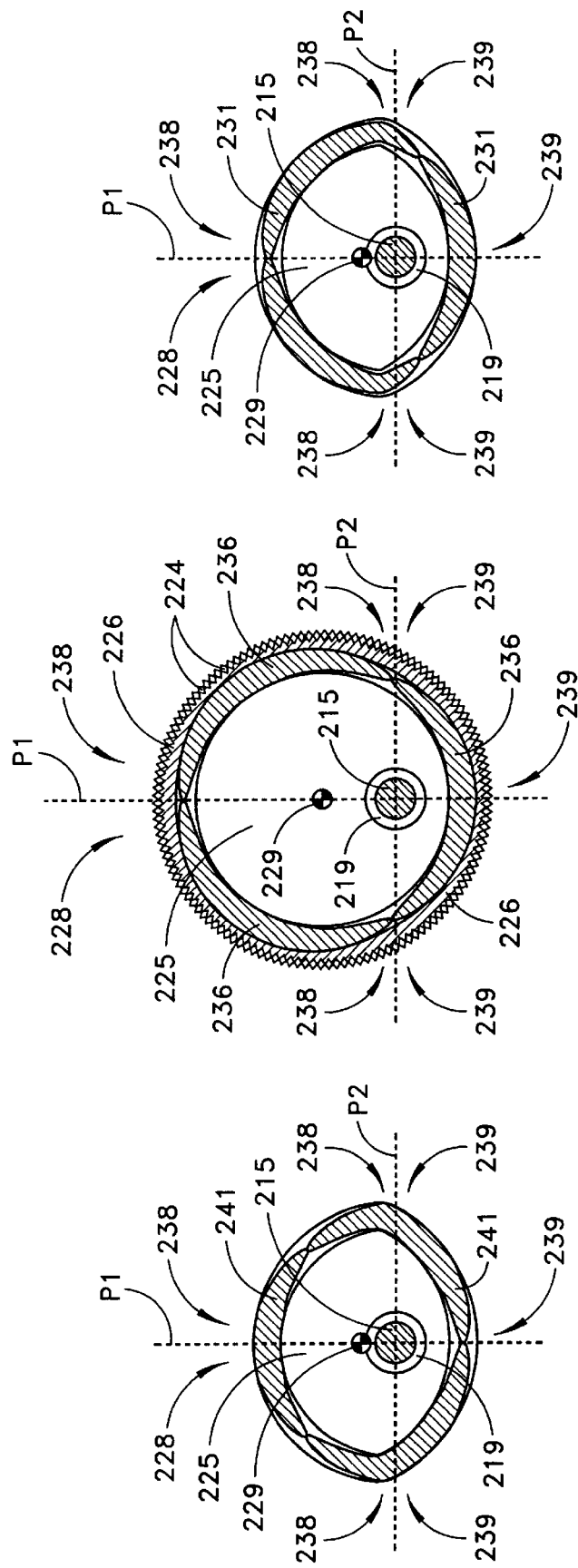

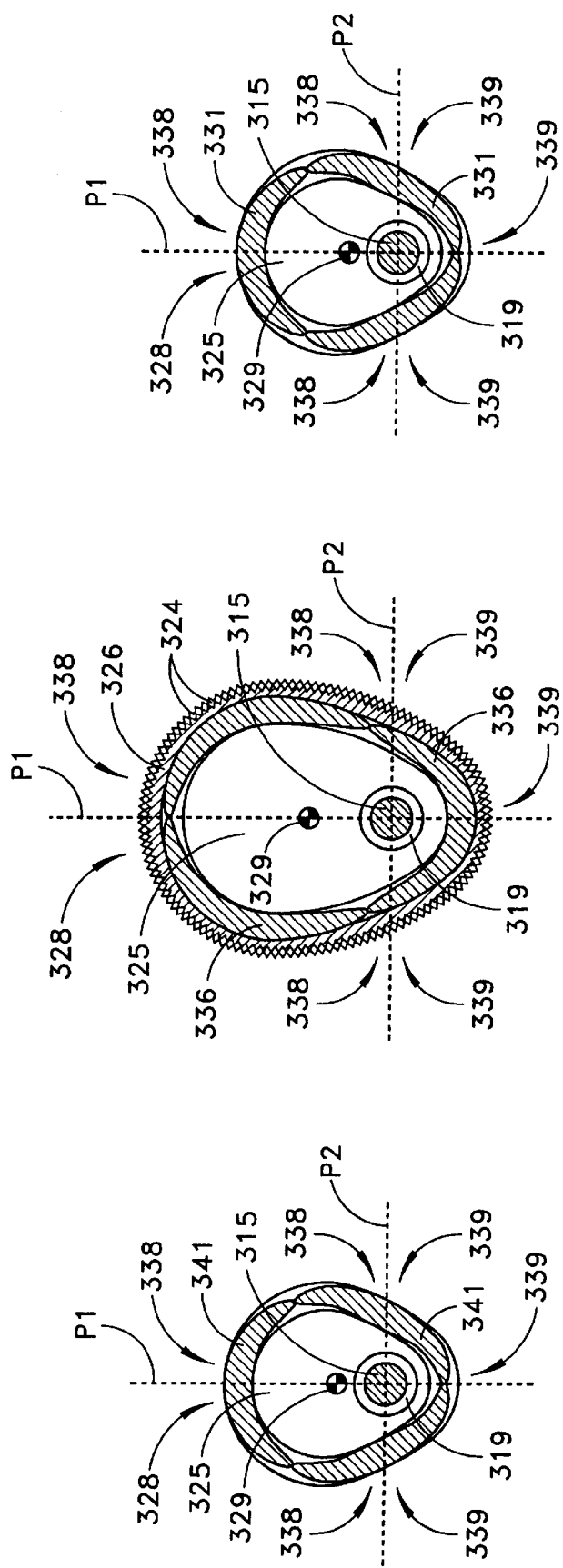
FIG. 34C
FIG. 34E
FIG. 34B
FIG. 34A
FIG. 34D

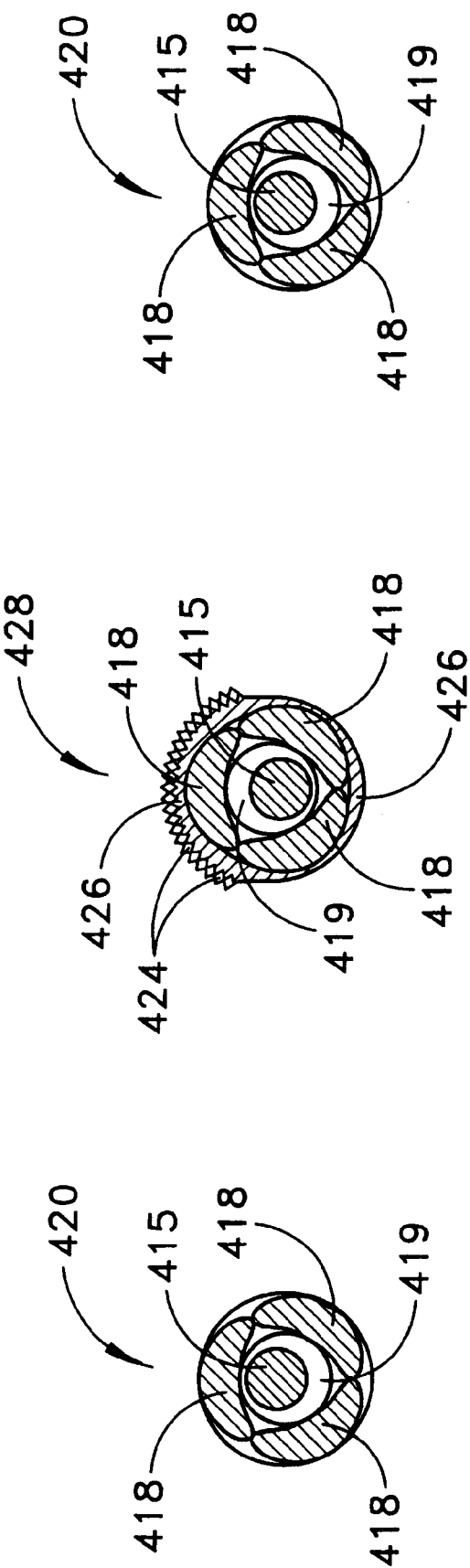

ECCENTRIC ROTATIONAL ATHERECTOMY DEVICE

TECHNICAL FIELD

The invention relates to devices and methods for removing tissue from body passageways, such as removal of atherosclerotic plaque from arteries, utilizing a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive cutting material such as diamond particles is carried at the distal end of a flexible drive shaft. The burr is rotated at high speeds (typically, e.g., in the range of about 150,000–190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) shows another atherectomy device having a drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged diameter section of the drive shaft.

SUMMARY OF THE INVENTION

The invention provides a rotational atherectomy device having a flexible, elongated, rotatable drive shaft with an eccentric enlarged diameter section. At least part of the eccentric enlarged diameter section has a tissue removing surface—typically an abrasive surface—to define a tissue removing segment of the drive shaft. When placed within an artery against stenotic tissue and rotated at sufficiently high speeds (e.g., in the range of about 20,000 rpm to about 200,000 rpm) the eccentric nature of the enlarged diameter section of the drive shaft causes such section to rotate in such a fashion as to open the stenotic lesion to a diameter substantially larger than the outer diameter of the enlarged diameter section. Preferably the eccentric enlarged diameter section of the drive shaft has a center of mass spaced radially from the rotational axis of the drive shaft, facilitating the ability of the device to open the stenotic lesion to a diameter substantially larger than the outer diameter of the enlarged diameter section. Typically this is achieved by spacing the geometric center of the eccentric enlarged diameter section of the drive shaft away from the rotational axis of the drive shaft. Such spacing of the geometric center from the rotational axis of the drive shaft can also be accomplished in rotational atherectomy devices having an eccentric tissue removal section with a diameter that is not enlarged, or by attaching an eccentric abrasive burr to a drive shaft. The rotational atherectomy device of the invention is capable of opening stenotic lesions to a diameter sufficiently large that balloon angioplasty is not needed to complete the procedure. The device is particularly useful for cleaning out partially blocked stents.

BRIEF DESCRIPTION OF THE DRAWINGS

FIGS. 3A–3E are transverse cross-sectional views of FIG. 3, taken along lines 3A—3A through 3E—3E thereof;

FIG. 22 is a longitudinal cross-sectional view of the clamp of FIG. 21;

FIG. 23 is an enlarged view showing in longitudinal cross-section details of a portion of FIG. 22;

FIG. 24 is an enlarged cross-sectional view, partially broken away, of FIG. 22, taken along lines 24—24 thereof;

FIGS. 26A–26K are transverse cross-sectional views of FIG. 26, taken along lines 26A—26A through 26K—26K thereof;

FIGS. 28–30 are schematic diagrams of steps in the process of machining the eccentric enlarged diameter component of the mandrel of FIG. 26;

FIGS. 31A–31C are transverse cross-sectional views of FIG. 31, taken along lines 31A—31A through 31C—31C thereof;

FIGS. 34A–34E are transverse cross-sectional views of FIG. 34, taken along lines 34A—34A through 34E—34E thereof;

FIGS. 36A–36C are transverse cross-sectional views of FIG. 36, taken along lines 36A—36A through 36C—36C thereof;

DETAILED DESCRIPTION OF THE INVENTION

Figure 1:
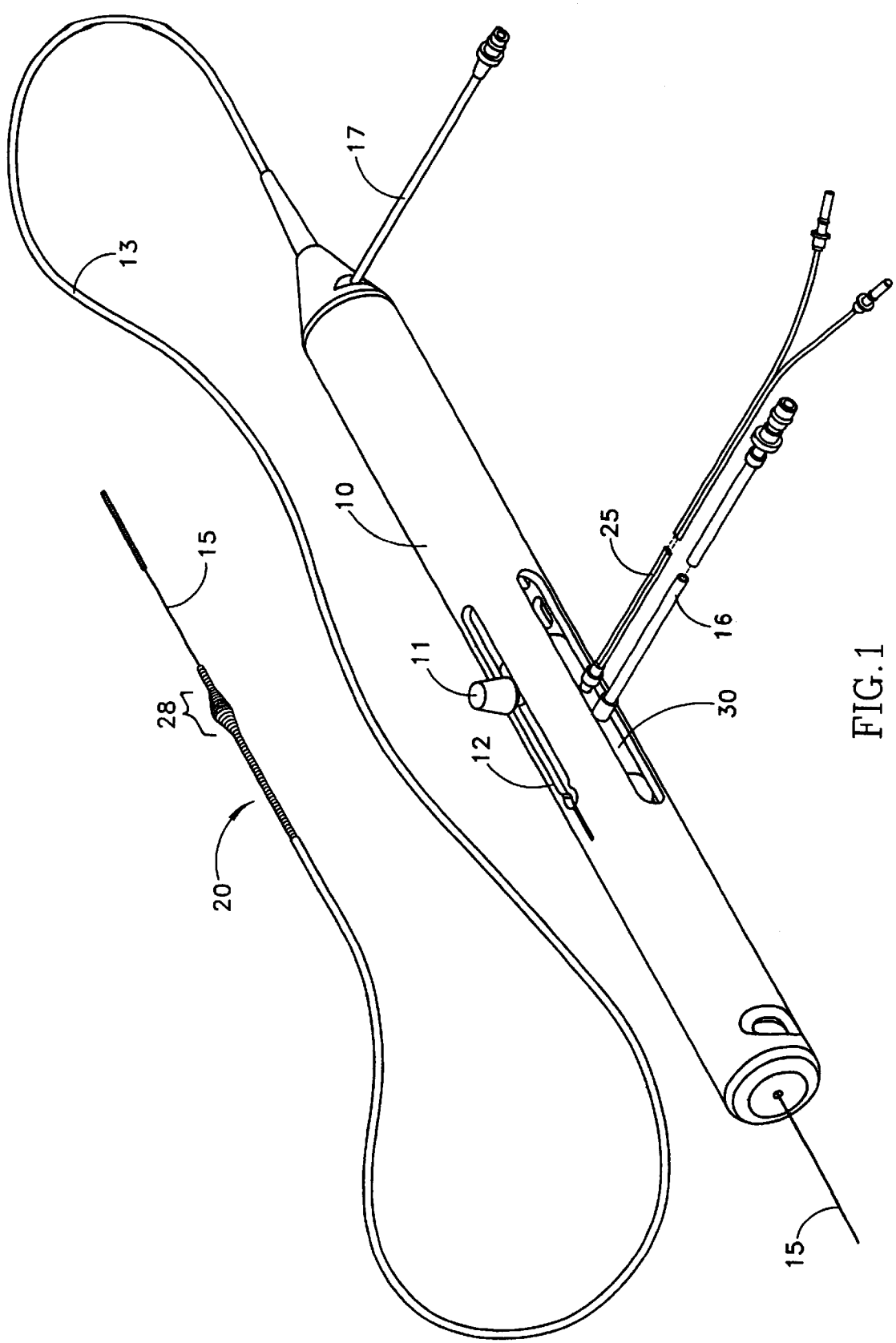
FIG. 1 is a perspective view of a rotational atherectomy device of the invention.
Figure 2:
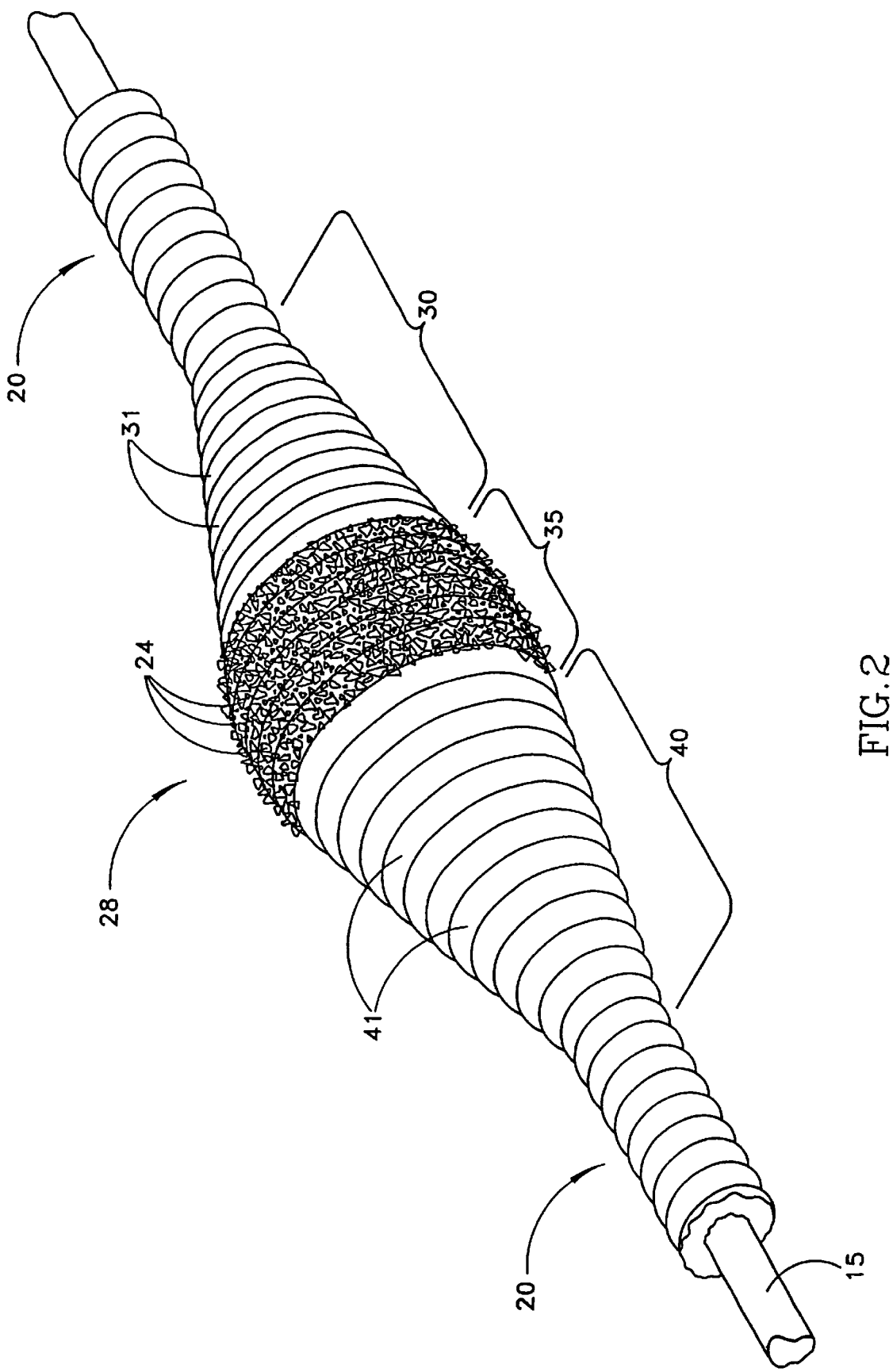
FIG. 2 is perspective, broken-away view of an eccentric enlarged diameter section of the drive shaft of a rotational atherectomy device of the invention.

FIG. 1 illustrates a typical rotational atherectomy device of the invention. The device includes a handle portion 10, an elongated, flexible drive shaft 20 having an eccentric enlarged diameter section 28, and an elongated catheter 13 extending distally from the handle portion 10. The drive shaft 20 and its eccentric enlarged diameter section 28 are constructed from helically coiled wire. The catheter 13 has a lumen in which most of the length of the drive shaft 20 is disposed, except for its enlarged diameter section 28 and a short section distal to the enlarged diameter section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25 may also be provided for monitoring the speed of rotation of the turbine and drive shaft 20 (details regarding such handles and associated instrumentation are well know in the industry, and are described, e.g., in U.S. Pat. No. 5,314,407, issued to Auth). The handle 10 also desirably includes a control knob 11 for advancing and retracting the turbine and drive shaft 20 with respect to the catheter 13 and the body of the handle.

FIGS. 2–5 illustrate details of the eccentric enlarged diameter section 28 of one embodiment of the invention. The drive shaft 20 is comprised of one or more helically wound wires 18 which define a guide wire lumen 19 and a hollow cavity 25 within the enlarged diameter section 28. Except for the guide wire 15 traversing the hollow cavity 25, the hollow cavity 25 is substantially empty. The eccentric enlarged diameter section 28 includes proximal 30, intermediate 35 and distal 40 portions. Wire turns 31 of the proximal portion 30 of the eccentric enlarged diameter section 28 preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35 are provided with gradually changing diameters to provide a generally convex outer surface which is shaped to provide a smooth transition between the proximal and distal conical portions of the enlarged diameter section 28 of the drive shaft 20.

At least part of the eccentric enlarged diameter section 28 (preferably the intermediate portion 35) includes an external surface capable of removing tissue. Preferably the tissue removing surface comprises a coating of an abrasive material 24 to define a tissue removing segment of the drive shaft 20. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable binder 26—such attachment may be achieved using well known techniques, such as conventional electroplating or fusion technologies (see, e.g., U.S. Pat. No. 4,018,576). Alternately the external tissue removing surface may be simply a section of the wire turns which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface.

Figure 3:
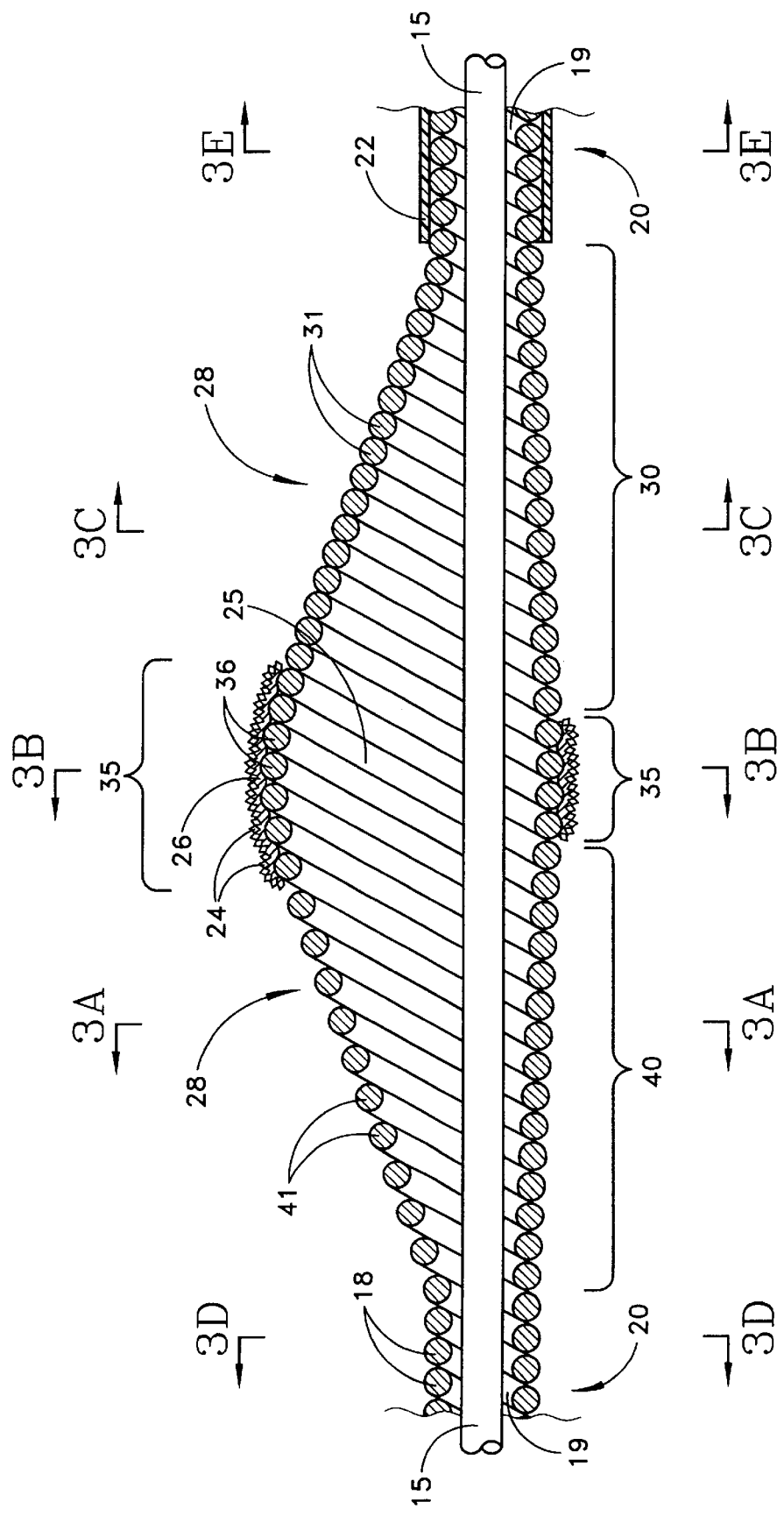
FIG. 3 is a broken-away, longitudinal cross-sectional view of the eccentric enlarged diameter section of the atherectomy device of the invention.
Figure 4:
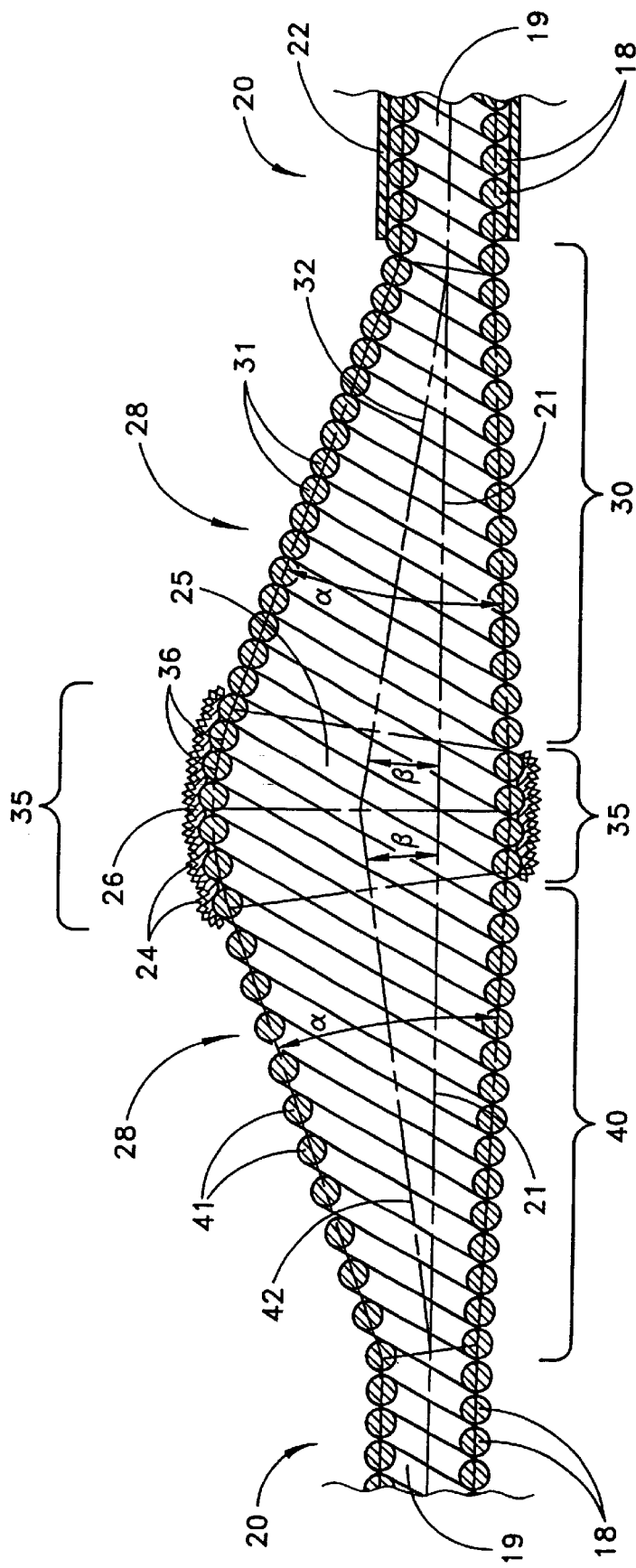
FIG. 4 is a broken-away, longitudinal cross-sectional view similar to FIG. 3, illustrating the geometry of one embodiment of an eccentric enlarged diameter section of the atherectomy device of the invention.

FIGS. 3–4 illustrate the particular geometry of one embodiment of an eccentric enlarged diameter section 28 of the invention. The elongated drive shaft 20 has a rotational axis 21 (see FIG. 4) which is coaxial with the guide wire 15 (see FIGS. 33E), the guide wire 15 being disposed within the lumen 19 of the drive shaft 20. The proximal portion 30 of the eccentric enlarged diameter section 28 has an outer surface which is substantially defined by the lateral surface of a frustum of a cone, the cone having an axis 32 which intersects the rotational axis 21 of the drive shaft 20 at a relatively shallow angle. Similarly, the distal portion 40 of the enlarged diameter section 28 has an outer surface which is substantially defined by the lateral surface of a frustum of a cone, the cone having an axis 42 which also intersects the rotational axis 21 of the drive shaft 20 at a relatively shallow angle. The cone axis 32 of the proximal portion 30 and the cone axis 42 of the distal portion 40 intersect each other and are coplanar with the longitudinal rotational axis 21 of the drive shaft.

The opposing sides of the cones generally should be at an angle $\alpha$ of between about 10° and about 30° with respect to each other; preferably the angle $\alpha$ is between about 20° and about 24°, and most preferably the angle $\alpha$ is about 22°. Also, the cone axis 32 of the proximal portion 30 and the cone axis 42 of the distal portion 40 normally intersect the rotational axis 21 of the drive shaft 20 at an angle $\beta$ of between about 20 and about 8°. Preferably the angle $\beta$ is between about 3° and about 6°. Although in the preferred embodiment shown in the drawings the angles $\alpha$ of the distal and proximal portions of the enlarged diameter section 28 are generally equal, they need not be equal. The same is true for the angles $\beta$.

Because the cone axes 32 and 42 intersect the rotational axis 21 of the drive shaft 20 at an angle $\beta$, the eccentric enlarged diameter section 28 has a center of mass that is spaced radially away from the longitudinal rotational axis 21 of the drive shaft 20. As will be described in greater detail below, offsetting the center of mass from the drive shaft's axis of rotation 21 provides the enlarged diameter section 28 with an eccentricity that permits it to open an artery to a diameter substantially larger than the nominal diameter of the enlarged diameter section 28.

FIGS. 3A–3C depict the positions of the centers of mass 29 of three cross-sectional slices (shown as faces of transverse cross-sections) of the eccentric enlarged diameter section 28. The entire eccentric enlarged diameter section 28 may be divided into many such thin slices, each slice having its own center of mass. FIG. 3B is taken at a position where the eccentric enlarged diameter section 28 has its maximum cross-sectional diameter (which, in this case, is the maximum diameter of the intermediate portion 35 of the eccentric enlarged diameter section 28), and FIGS. 3A and 3C are taken, respectively in the distal 40 and proximal 30 portions of the eccentric enlarged diameter section 28. In each of these cross-sectional slices the center of mass 29 is spaced away from the rotational axis of the drive shaft, the rotational axis of the drive shaft 20 coinciding with the center of the guide wire 15. The center of mass 29 of each cross-sectional slice also generally coincides with the geometric center of such cross-sectional slice. FIG. 3B shows the slice having the greatest cross-sectional diameter. In this slice both the center of mass 29 and the geometric center are located the furthest (i.e., maximally spaced away) from the rotational axis of the drive shaft. Of course, the center of mass of the entire enlarged diameter section is a composite of the individual centers of mass of multiple slices of the enlarged diameter section, and the overall center of mass will, therefore, be closer to the axis of rotation of the drive shaft than the center of mass of the slice depicted in FIG. 3B. FIGS. 3D–3E illustrate the fact that both the centers of mass 29 and the geometric centers of those slices of the drive shaft 20 which are taken both proximally and distally of the eccentric enlarged diameter section 28 coincide with the center of the guide wire 15 and, thus, the rotational axis of the drive shaft 20. Therefore, such portions of the drive shaft located proximally and distally of the enlarged diameter section 28 are not eccentric (are balanced) with respect to the rotational axis of the drive shaft.

In considering the eccentricity of the enlarged diameter section 28 of the drive shaft one can geometrically divide the enlarged diameter section 28 into two generally symmetrical lobes, such lobes being on opposite sides of a plane $P_1$. drawn through the longitudinal rotational axis and either the center of mass of the eccentric enlarged diameter section (see FIGS. 3A–3C, which show centers of mass 29 of individual slices) or the point on the outer surface of the eccentric enlarged diameter section which is most distant from the rotational axis. A second plane $P_2$, perpendicular to the first plane $P_1$ and containing the rotational axis, divides the eccentric enlarged diameter section 28 into major 38 and minor 39 lobes (located respectively above and below the plane $P_2$ in FIGS. 3A–3C). The major lobe 38 has a mass larger than the mass of the minor lobe 39, due primarily to the fact that the major lobe 38 includes a larger portion of the outer surface area than the minor lobe 39. Thus, the center of mass of the entire eccentric enlarged diameter section 28 is located within the major lobe 38. The maximum distance from the rotational axis of the drive shaft to the outer surface of the major lobe 38 is larger than a maximum distance from the rotational axis of the drive shaft to the outer surface of the minor lobe 39.

It should be understood that, as used herein, the word "eccentric" is intended to refer to either a difference in location between the geometric center of the enlarged diameter section 28 and the rotational axis of the drive shaft, or to a difference in location between the center of mass of the enlarged diameter section 28 and the rotational axis of the drive shaft. Either such difference, at the proper rotational speeds, will enable the eccentric enlarged diameter section 28 to open a stenosis to a diameter substantially greater than the nominal diameter of the eccentric enlarged diameter section. Moreover, for an eccentric enlarged diameter section having a shape that is not a regular geometric shape, the concept of "geometric center" can be approximated by locating the mid-point of the longest chord which is drawn through the rotational axis of the drive shaft and connects two points on a perimeter of a transverse cross-section taken at a position where the perimeter of the eccentric enlarged diameter section has its maximum length.

Figure 5:
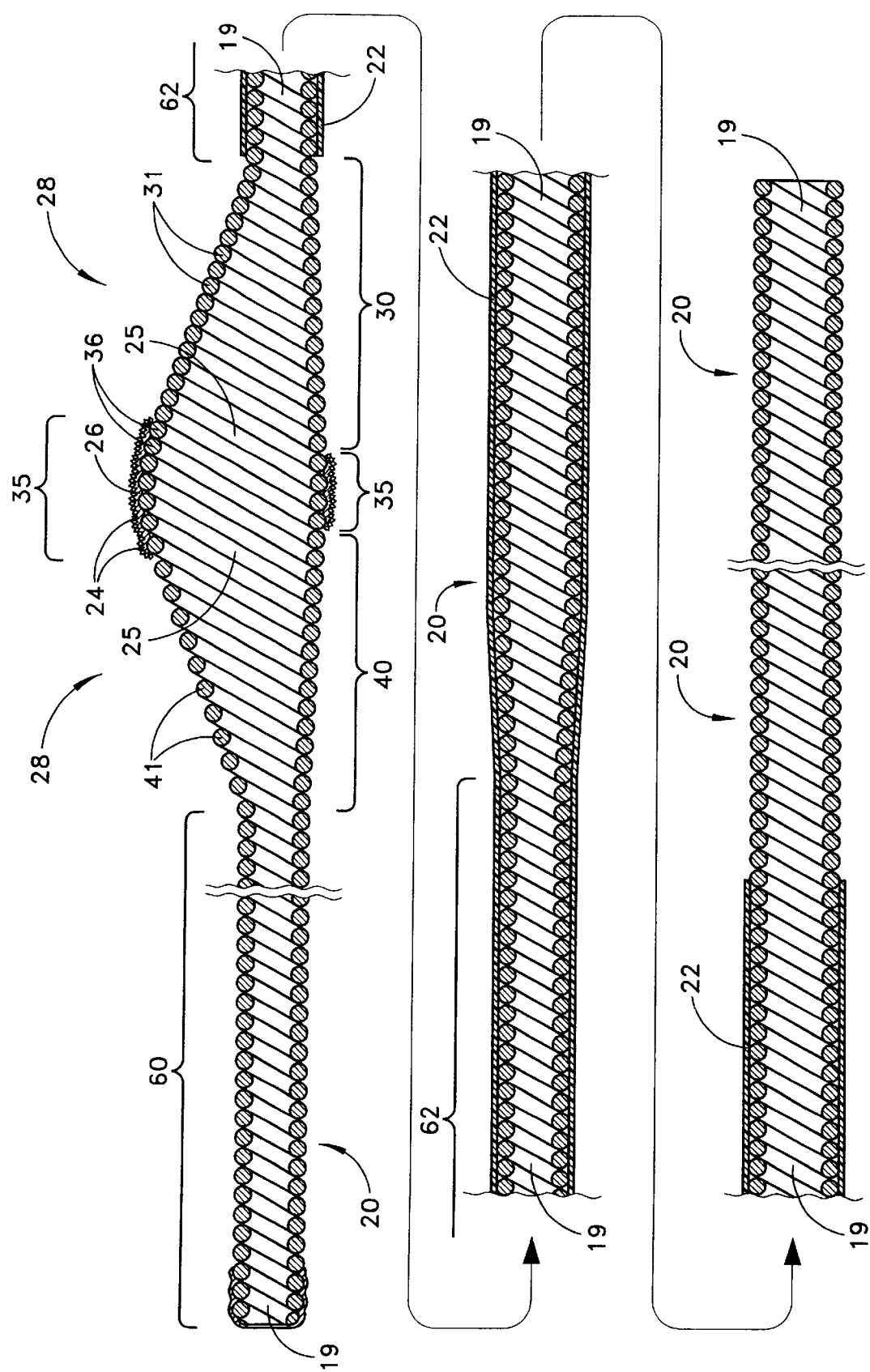
FIG. 5 is a broken-away, longitudinal cross-sectional view of the drive shaft of an atherectomy device of the invention.

Referring to FIG. 5, the elongated drive shaft 20 has proximal and distal sections, located proximally and distally of the eccentric enlarged diameter section 28 of the drive shaft. Except, of course, for the enlarged diameter section 28, the lumen 19 of the drive shaft 20 has a generally constant diameter along substantially its entire length. To reduce vibrations which may occur during rotation of the drive shaft 20 and its eccentric enlarged diameter section 28 around the guide wire 15, portions of the drive shaft 20 immediately proximal and distal to the enlarged diameter section 28 are provided with a slightly reduced inner diameters, the reduced diameter portions of the drive shaft thus functioning as bearings to facilitate sufficiently smooth rotation of the drive shaft 20 around the guide wire 15. In FIG. 5, the entire distal section 60 of the drive shaft 20 and portion 62 of the proximal section are provided with such reduced inner diameters. If desired, the reduced diameter portion may be limited only to the distal segment of the drive shaft 20. Limiting the reduced diameter portion only to the proximal segment of the drive shaft 20 is also possible, but less desirable. In addition, if desired, more than one such reduced diameter segment could be provided on either side of the enlarged diameter section 28.

A portion of the drive shaft 20 proximal to the eccentric enlarged diameter section 28 may be encased in a thin, flexible, low friction sheath or coating 22. In a preferred embodiment, the sheath or coating 22 is sufficiently long so that its proximal end remains disposed inside the catheter 13 even when the drive shaft 20, with its enlarged diameter section 28, is fully advanced distally with respect to the catheter 13. Applicants have successfully utilized heat shrinkable polyester tubing to make such sheath 22 (available, e.g., from Advanced Polymers, Inc. of Salem, N.H.). The sheath or coating 22 may be made from other suitable materials, including, e.g., polytetrafluoroethylene compounds.

FIGS. 6–14A illustrate a series of steps in which the eccentric rotational atherectomy device of the invention is used to open a stenotic lesion to a diameter substantially larger than the nominal diameter of the eccentric enlarged diameter section 28 of the drive shaft 20.

Figure 6:
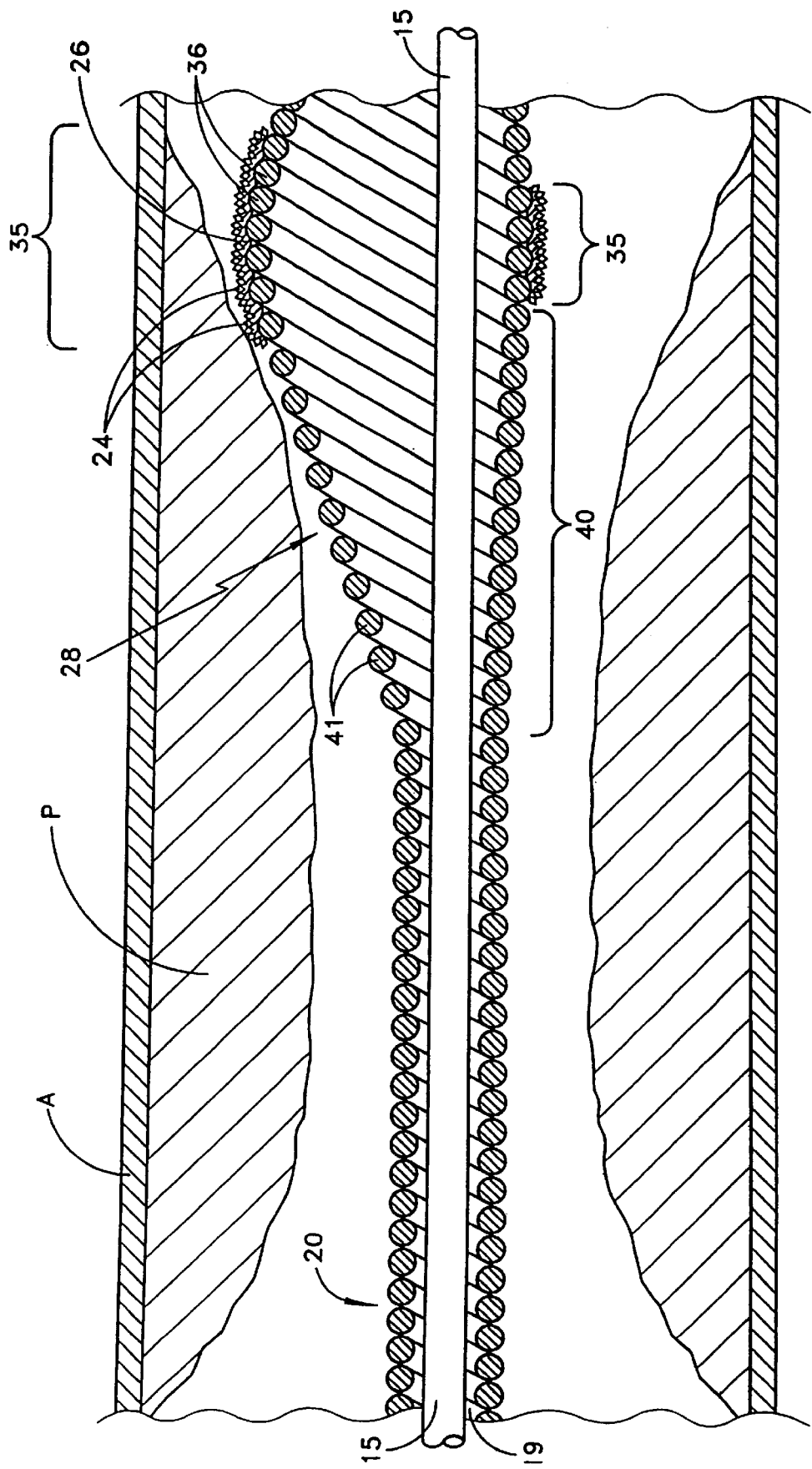
FIG. 6 is a longitudinal cross-sectional view of an eccentric enlarged diameter section of the atherectomy device of the invention, shown just prior to being used to remove stenotic tissue from an artery.
Figure 7:
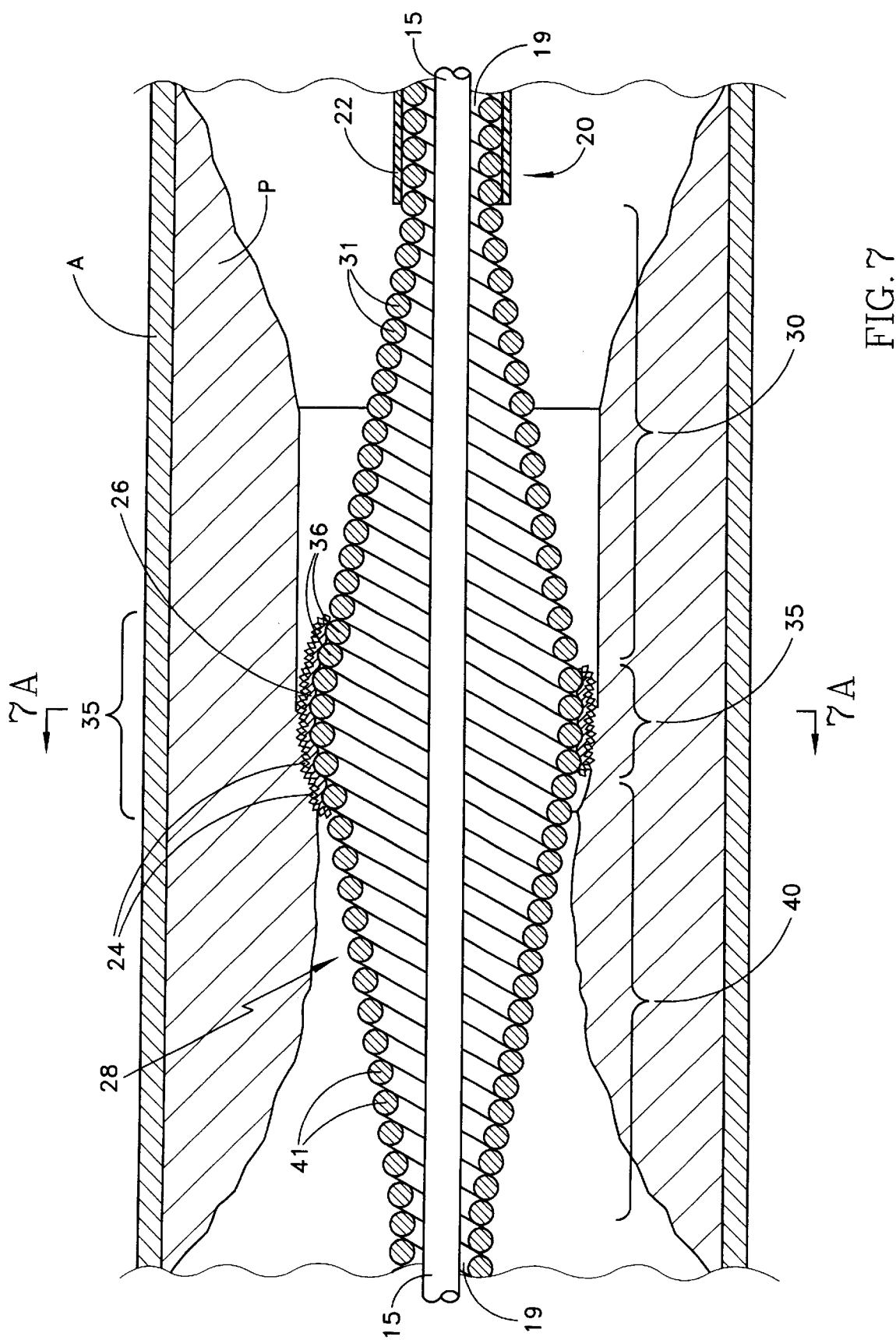
FIG. 7 is a longitudinal cross-sectional view similar to FIG. 6, showing the eccentric enlarged diameter section being moved distally to remove stenotic tissue from an artery.
Figure 7A:
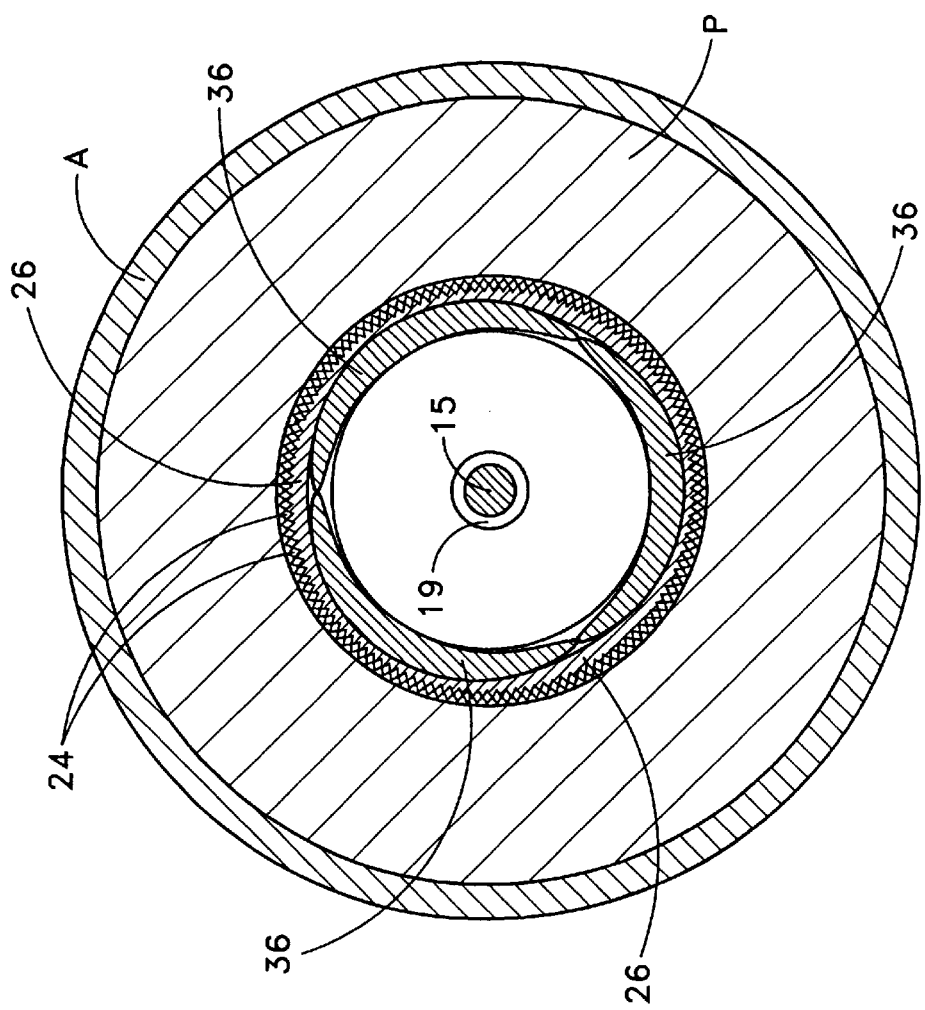
FIG. 7A is a transverse cross-sectional view of FIG. 7, taken along lines 7A—7A thereof.

In FIG. 6 the eccentric enlarged diameter section 28 has been advanced over the guide wire 15 to a position just proximal to a stenosis in an artery "A", the diameter of the stenosis (defined by plaque "P") being slightly smaller than the nominal maximum diameter of the eccentric enlarged diameter section 28 of the drive shaft 20. In FIG. 7 the eccentric enlarged diameter section 28 is being advanced across the stenosis, removing a thin first layer of plaque "P." As can be seen in FIG. 6, the guide wire 15 is centered with respect to the stenosis, while the enlarged diameter section 28 is at its "at-rest" eccentric configuration with respect to the guide wire 15. As described above, in the "at-rest" eccentric configuration both the geometric center and the center of mass of the enlarged diameter section 28 are spaced away from the center of the guide wire 15 and, thus, the rotational axis of the drive shaft 15. FIGS. 7 and 7A illustrate that further advancement of eccentric enlarged diameter section 28 into the stenosis causes the section 28 to be deformed by the stenosis to a configuration in which the enlarged diameter section 28 becomes substantially symmetrical with respect to the guide wire 15. Thus, in FIGS. 7–7A, the enlarged diameter section 28 temporarily has changed its shape to a configuration in which its center of mass and its geometric center have been moved close to the center of the guide wire 15, thereby making the enlarged diameter section temporarily substantially balanced (not eccentric) with respect to the guide wire 15 and the rotational axis of the drive shaft. This change in configuration of the enlarged diameter section 28 is made possible because adjacent wire turns in the proximal 30 and distal 40 portions of the enlarged diameter section 28 are not secured to each other, thereby permitting these portions to flex to the configuration depicted in FIGS. 7–7A.

Figure 8:
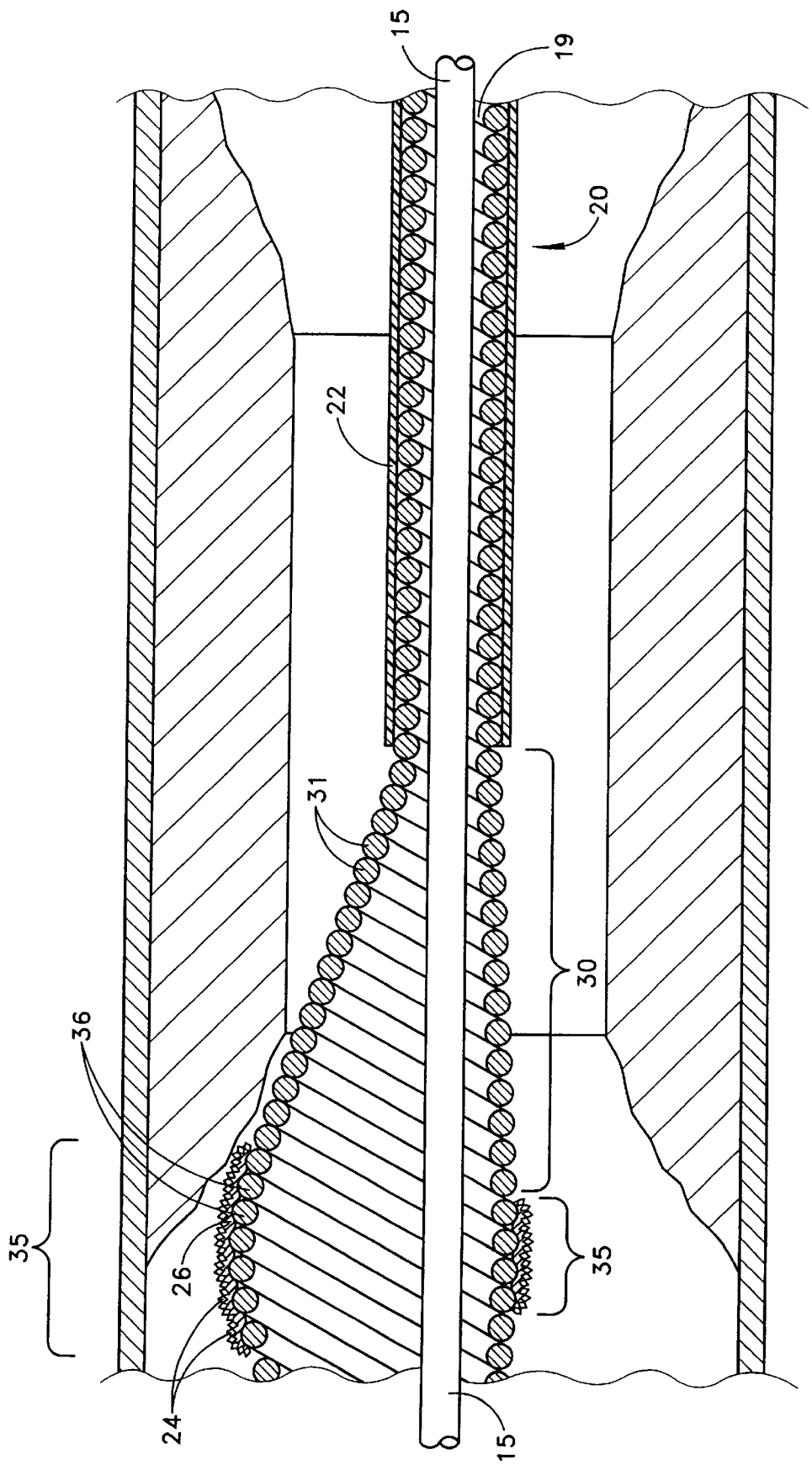
FIG. 8 is a longitudinal cross-sectional view similar to FIGS. 6–7, showing the eccentric enlarged diameter section after it has moved distally through a stenosis.

In FIG. 8 the eccentric enlarged diameter section 28 has entirely crossed the stenosis, removing a first layer of the plaque "P" from the stenosis. Having emerged distally from the stenosis, the eccentric enlarged diameter section 28 has again regained its "at-rest" eccentric configuration.

Figure 9:
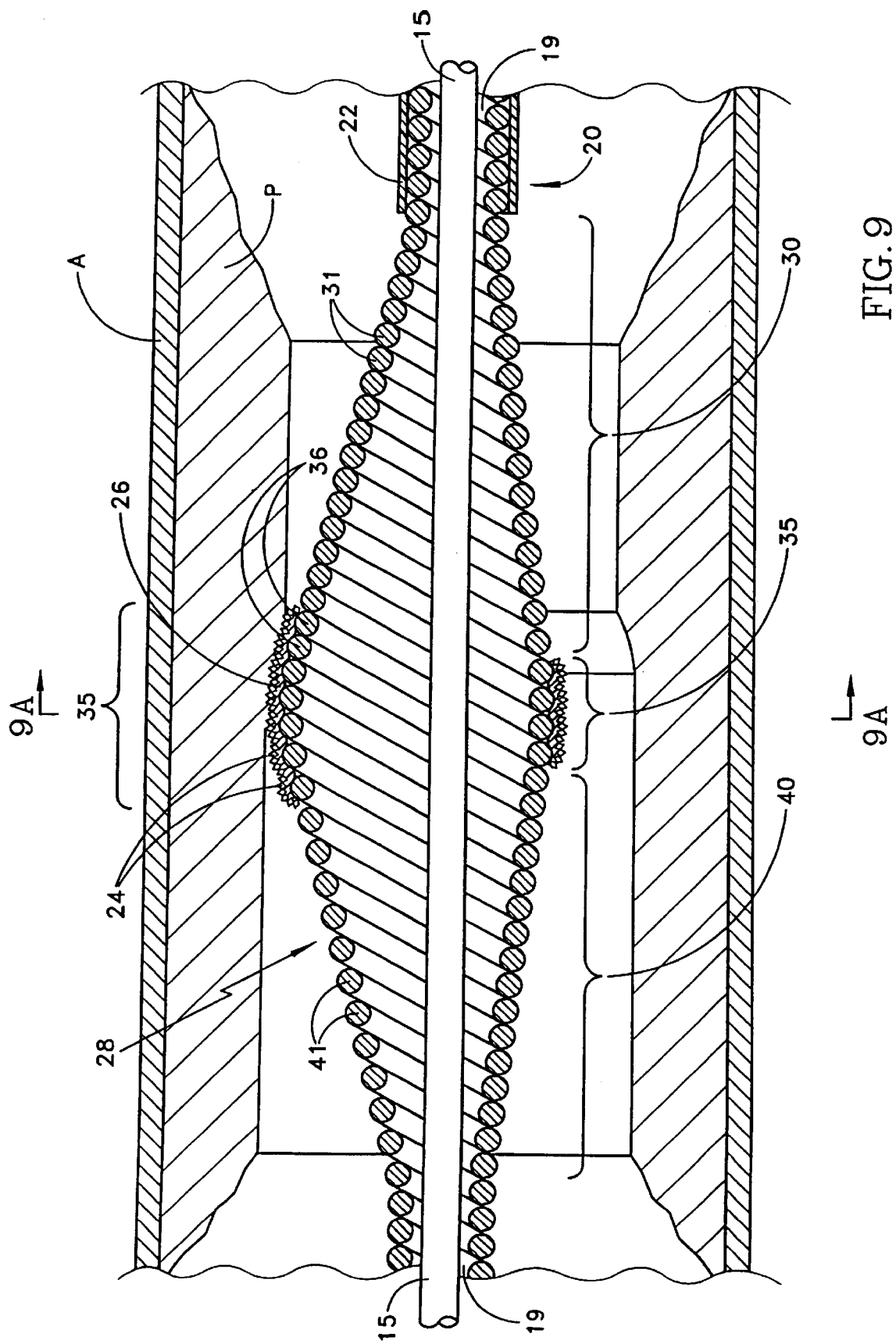
FIG. 9 is a longitudinal cross-sectional view similar to FIGS. 6–8, showing a subsequent stage of removal of stenotic tissue from an artery, the eccentric enlarged diameter section being moved proximally through a stenosis.
Figure 9A:
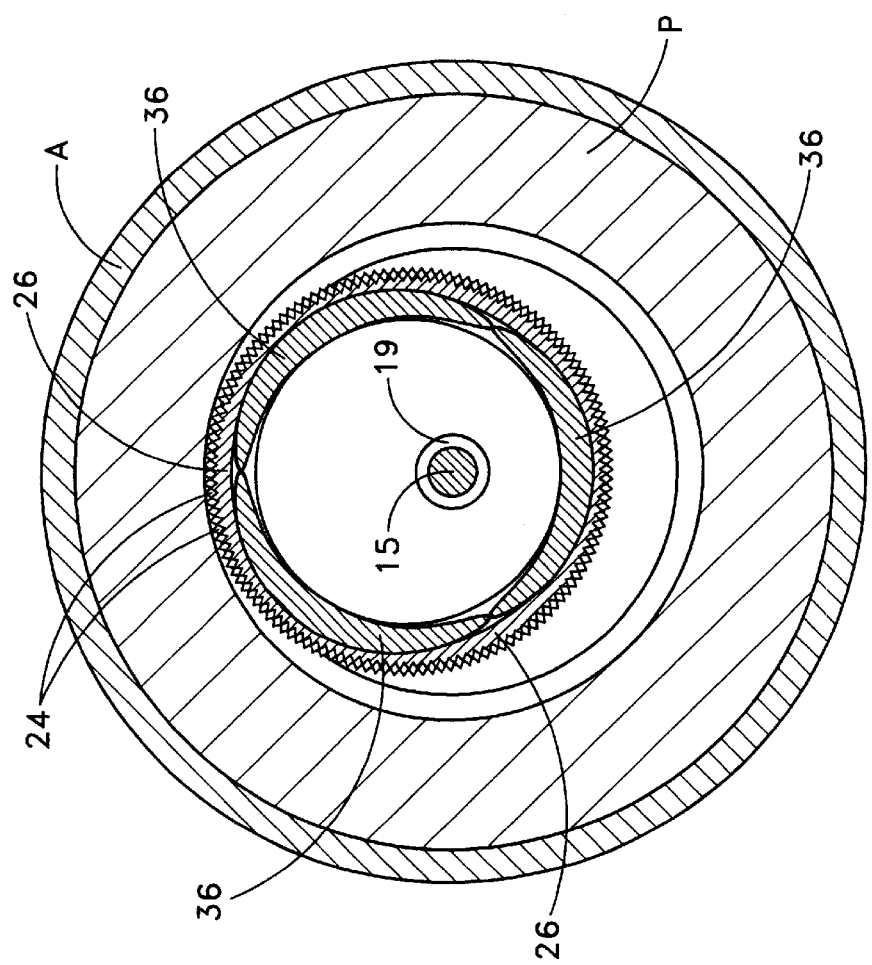
FIG. 9A is transverse cross-sectional view of FIG. 9, taken along lines 9A—9A thereof.

In FIGS. 9–9A the eccentric enlarged diameter section 28 is being withdrawn proximally across the stenosis. During this pass across the stenosis the inner diameter of the plaque "P" is larger than the nominal diameter of the eccentric enlarged diameter section 28. Nevertheless, the eccentric enlarged diameter section 28 of the invention is able to continue the tissue removal process due to a force pressing the intermediate portion 35 of the eccentric enlarged diameter section 28 laterally against the plaque "P." The actual total force $F_c$ pressing the rotating eccentric enlarged diameter section 28 against the plaque "P" is the sum of two forces, $F_c$, and $F_s$, (i.e., $F_t=F_c+F_s$), where $F_t$ is the total force, $F_c$ is the centrifugal force resulting from the center of mass of the eccentric enlarged diameter section 28 being offset from the rotational axis, and $F_s$, is the lateral spring force resulting from deformation of the proximal and distal portions of the eccentric enlarged diameter section 28 by the stenosis. The more the eccentric enlarged diameter section 28 is deformed by the plaque "P" into a "symmetric" or "balanced" configuration, the larger $F_s$ becomes. The further the center of mass is from the axis of rotation, and the faster the drive shaft and the eccentric enlarged diameter section 28 are rotated, the larger $F_c$ becomes.

Figure 10:
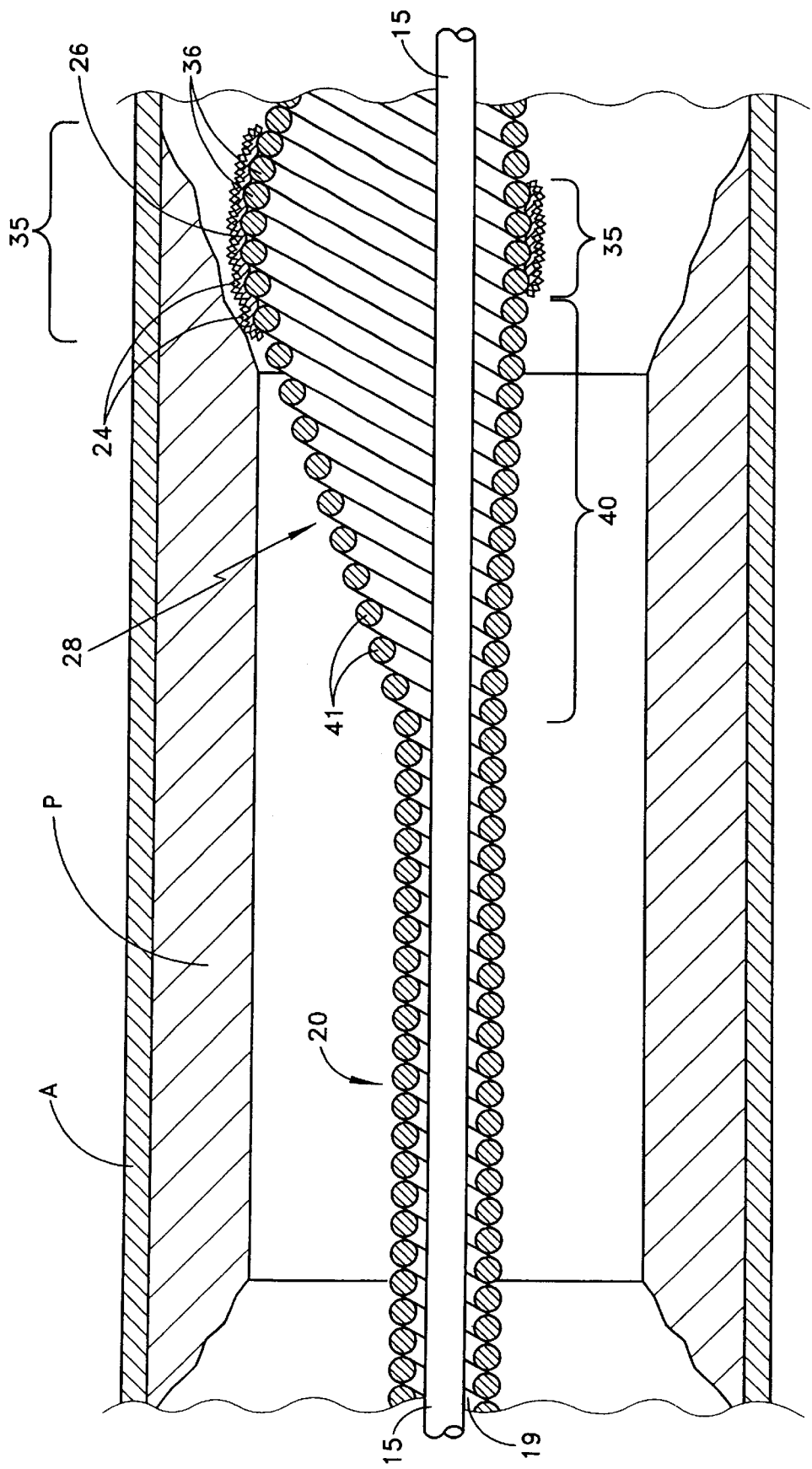
FIG. 10 is a longitudinal cross-sectional view similar to FIGS. 6–9, showing the eccentric enlarged diameter section after it has moved proximally through a stenosis.
Figure 11:
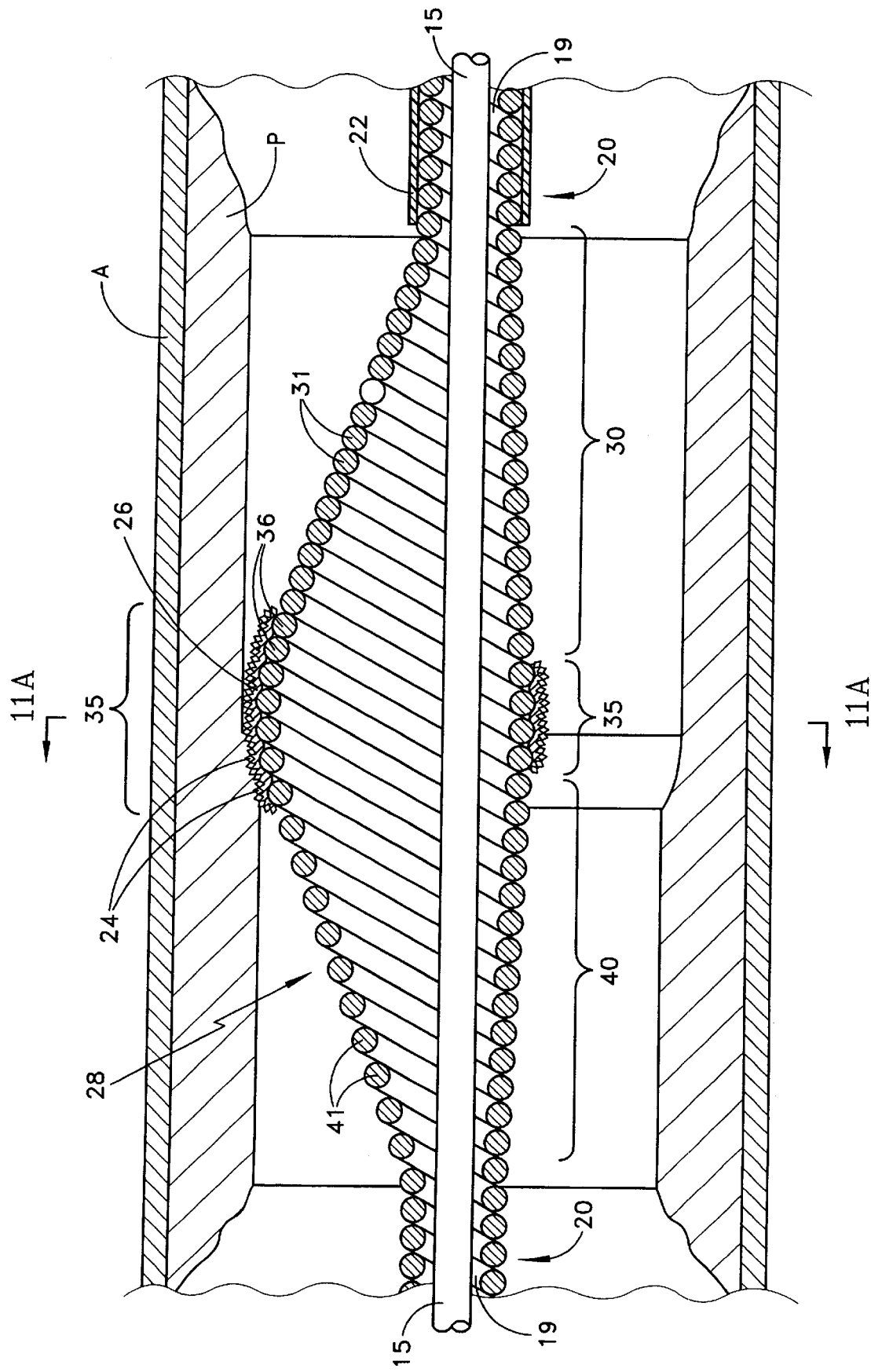
FIG. 11 is a longitudinal cross-sectional view similar to FIGS. 6–10, showing the eccentric enlarged diameter section again being moved distally through a stenosis.
Figure 11A:
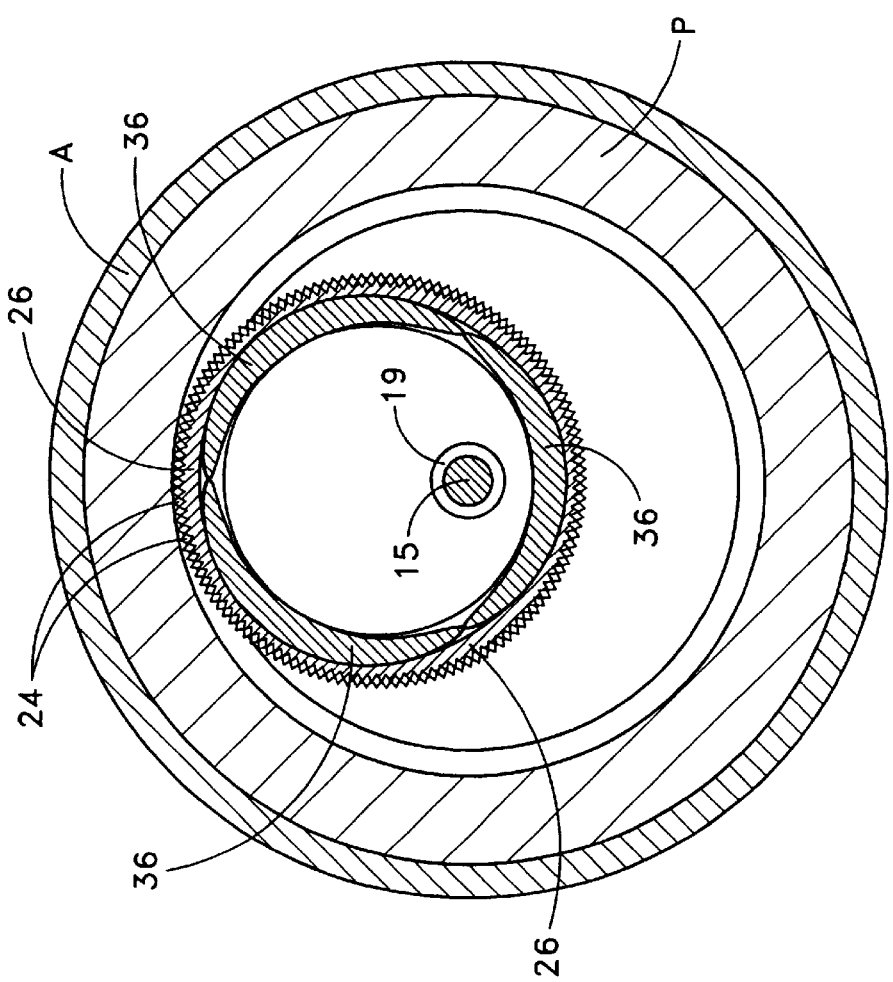
FIG. 11A is transverse cross-sectional view of FIG. 11, taken along lines 11A—11A.
Figure 12:
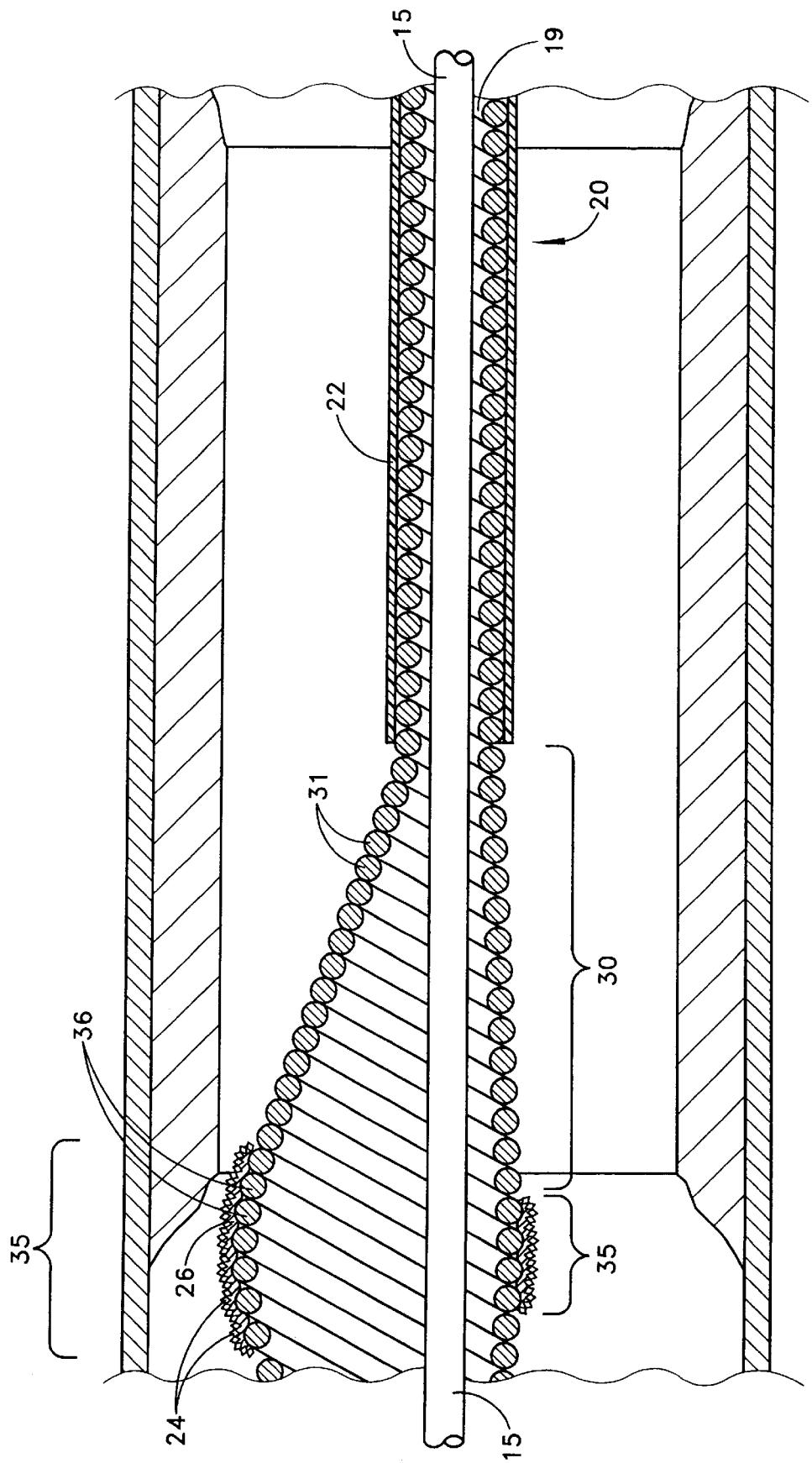
FIG. 12 is a longitudinal cross-sectional view similar to FIGS. 6–11, showing the eccentric enlarged diameter section after it has moved distally through a stenosis.

In FIG. 10 the eccentric enlarged diameter section 28 has again entirely crossed the stenosis, removing a second layer of the plaque "P" from the stenosis. Having emerged proximally from the stenosis, the eccentric enlarged diameter section 28 is depicted in its "at-rest" eccentric configuration.

As the drive shaft 20 is advanced and retracted to successively move the enlarged diameter section 28 across the stenosis, the rotating eccentric enlarged diameter section 28 will continue to remove plaque "P" from the artery "A", opening the stenosis to a diameter substantially larger than the nominal diameter of the enlarged diameter section 28. FIGS. 11–14A show successive stages of such tissue removal.

In FIG. 1 the diameter of the stenosis has been increased sufficiently so that the stenosis no longer deforms the eccentric enlarged diameter section 28, thereby reducing the lateral spring force $F_s$ to essentially zero and making the total force pressing the tissue removal surface against the plaque "P" essentially equal to the centrifugal force $F_c$.

Figure 13:
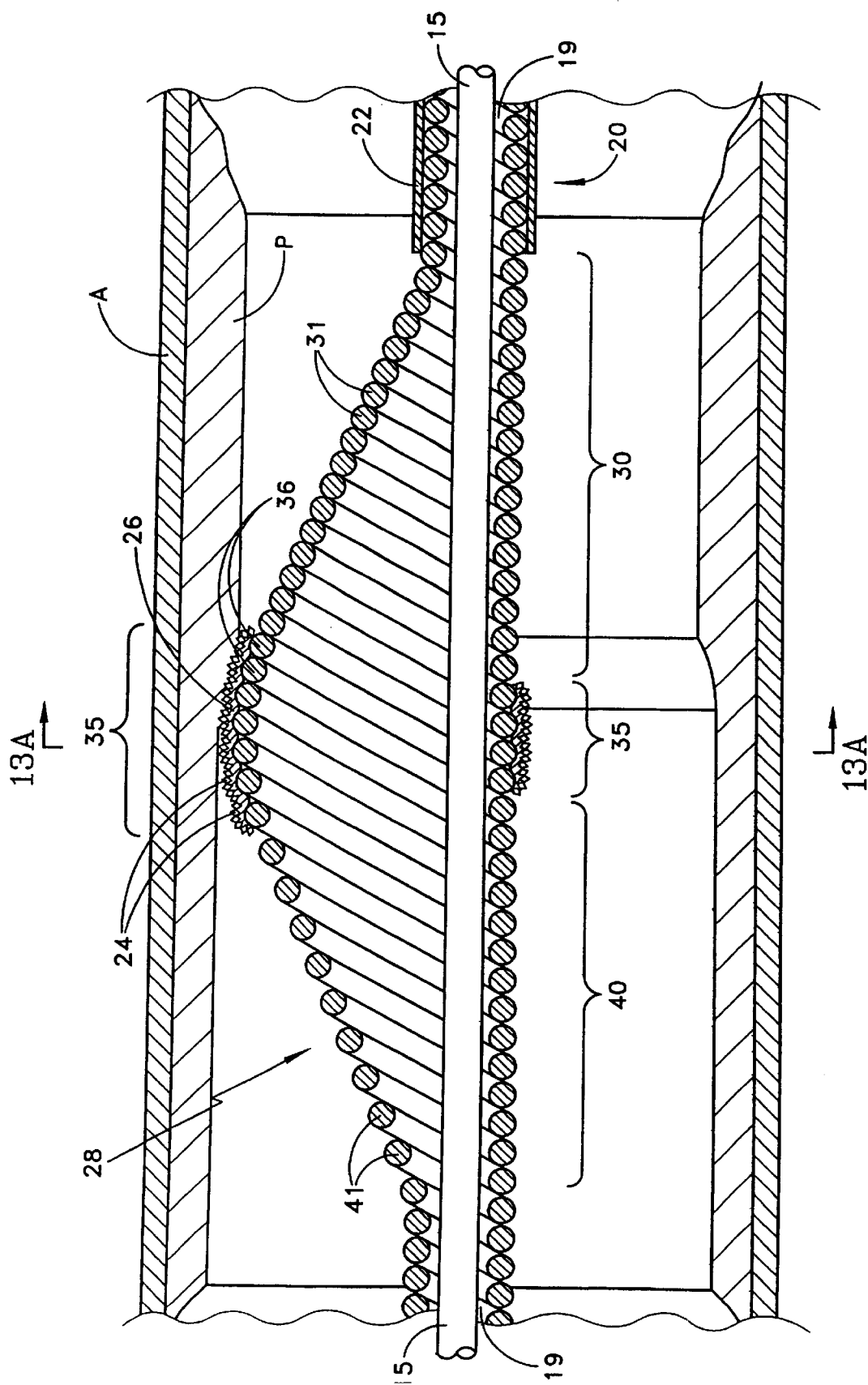
FIG. 13 is a longitudinal cross-sectional view similar to FIGS. 6–12, showing yet another subsequent stage of removal of stenotic tissue from an artery, the eccentric enlarged diameter section being moved proximally through a stenosis.
Figure 13A:
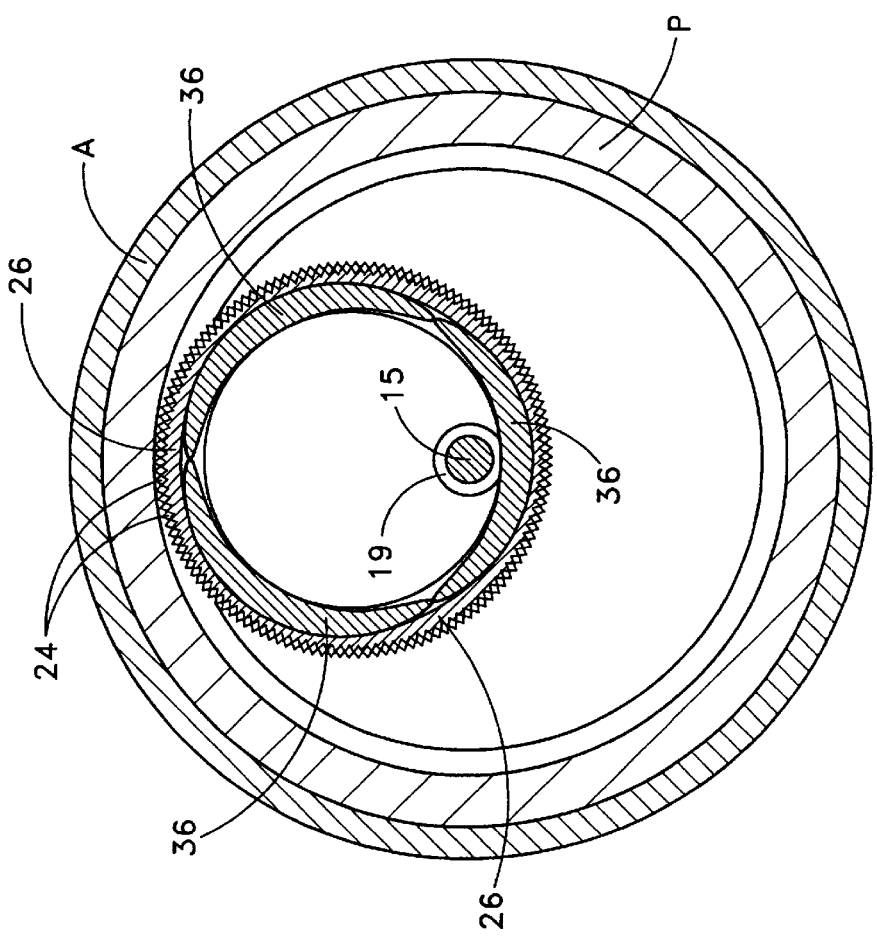
FIG. 13A is transverse cross-sectional view of FIG. 13, taken along lines 13A—13A thereof.

In the configuration depicted in FIGS. 13–13A, the eccentric enlarged diameter section 28 is again in a deformed shape, but this time the deformation is caused by centrifugal force $F_c$ rather than by the wall of the stenosis. In this situation, the lateral spring force $F_s$ is actually negative, as the lateral spring force is directed oppositely to the centrifugal force $F_c$. The lateral spring force thus tends to reduce the total force pressing the tissue removal surface against the plaque "P." When the inner wall of the eccentric enlarged diameter section 28 contacts the guide wire 15, as is shown in FIG. 13, additional friction between the inner wall and the guide wire 15 can be detected by the operator, signaling the fact that the device has opened the stenosis to a diameter which is approximately the maximum diameter to which the stenosis may be easily opened by the eccentric rotational atherectomy device of the invention.

Figure 14:
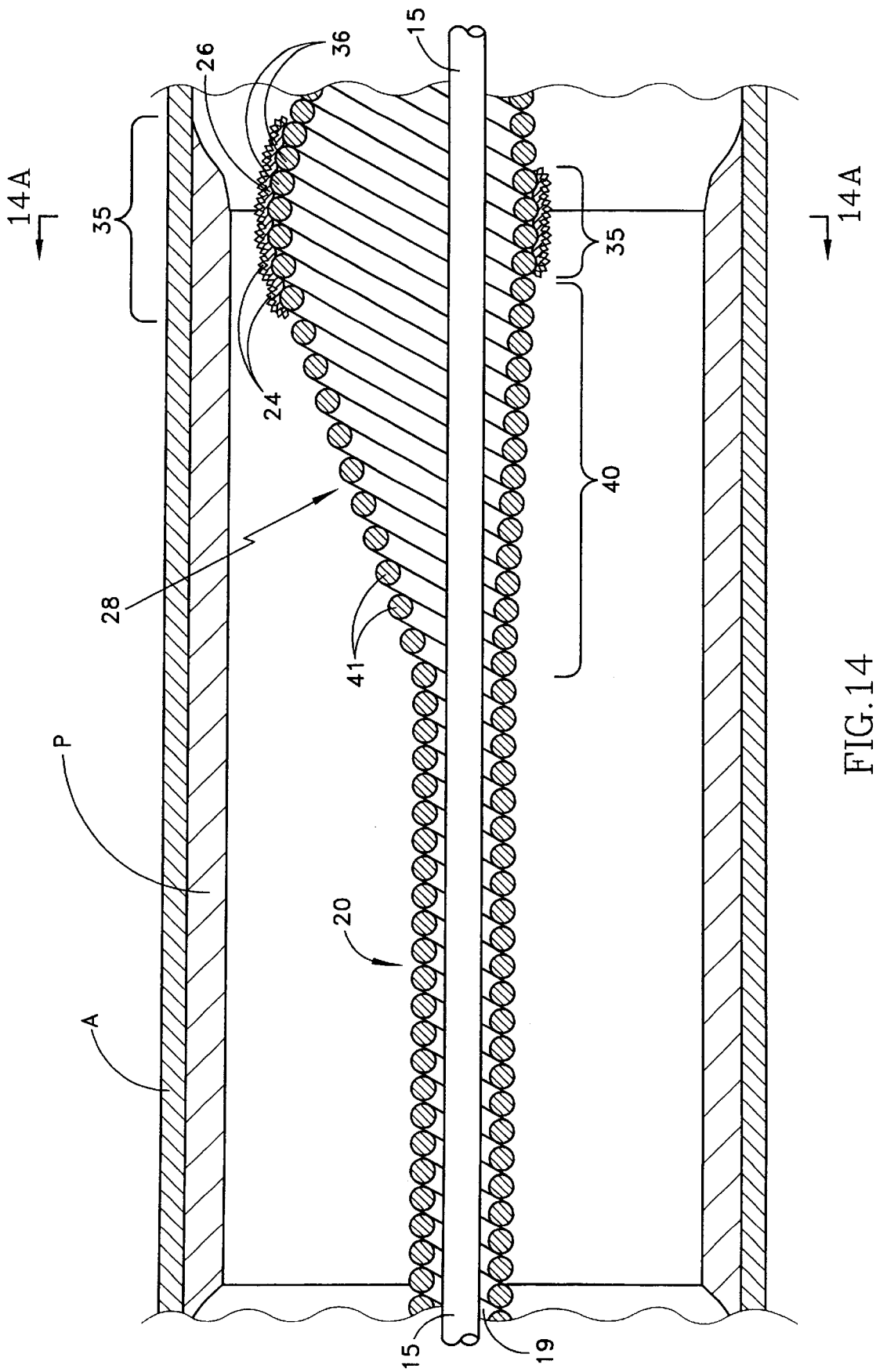
FIG. 14 is a longitudinal cross-sectional view similar to FIGS. 6–13, showing the eccentric enlarged diameter section in an at-rest (non-rotating) position after a stenosis has been substantially opened by the device.
Figure 14A:
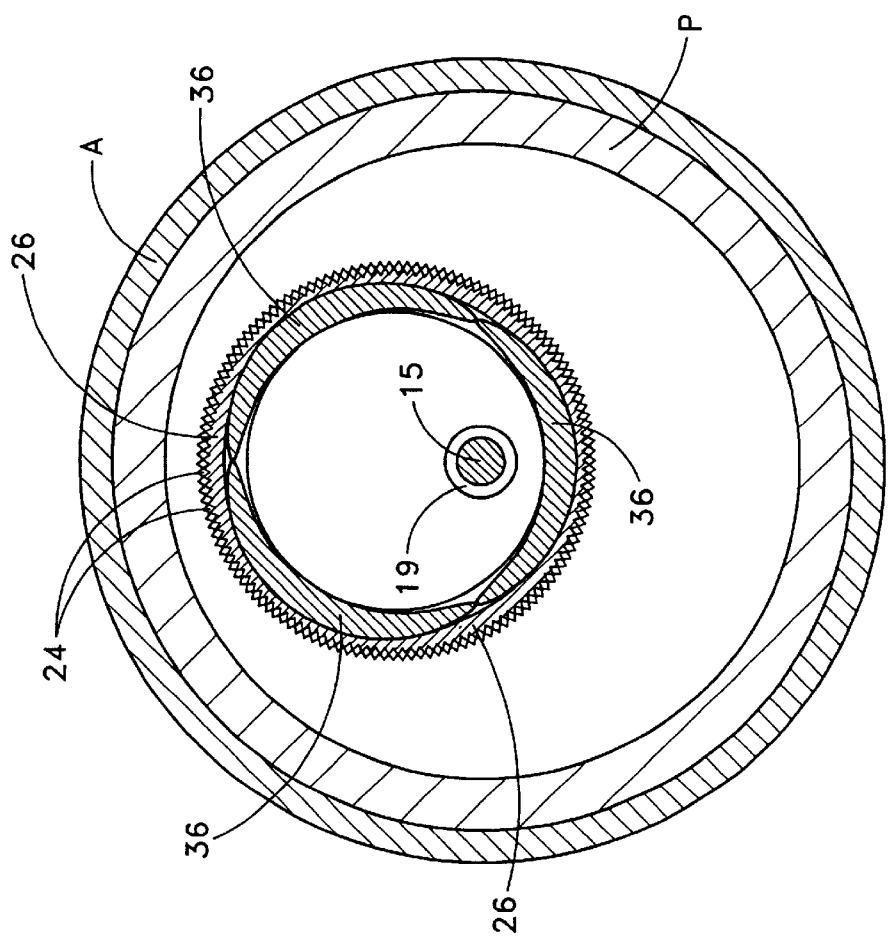
FIG. 14A is a transverse cross-sectional view of FIG. 14, taken along lines 14A—14A thereof.

FIGS. 14–14A depict the device in an "at-rest" position after the stenosis has been substantially opened. These figures illustrates the device's ability to open a stenosis to a diameter well in excess of the device's nominal diameter.

The extent to which a stenosis in an artery can be opened to a diameter larger than the nominal diameter of the eccentric enlarged diameter section depends on several parameters, including the shape of the eccentric enlarged diameter section, the mass of the eccentric enlarged diameter section, the distribution of that mass and, therefore, the location of the center of mass of this section with respect to the rotational axis of the drive shaft, and the speed of rotation. The speed of rotation is a significant factor in determining the centrifugal force with which the tissue removing surface of the enlarged diameter section is pressed against the stenotic tissue, thereby permitting the operator to control the rate of tissue removal. Control of the rotational speed also allows, to some extent, control over the maximum diameter to which the device will open a stenosis. Applicants have also found that the ability to reliably control the force with which the tissue removing surface is pressed against the stenotic tissue not only permits the operator to better control the rate of tissue removal but also provides better control of the size of the particles being removed.

Figure 15:
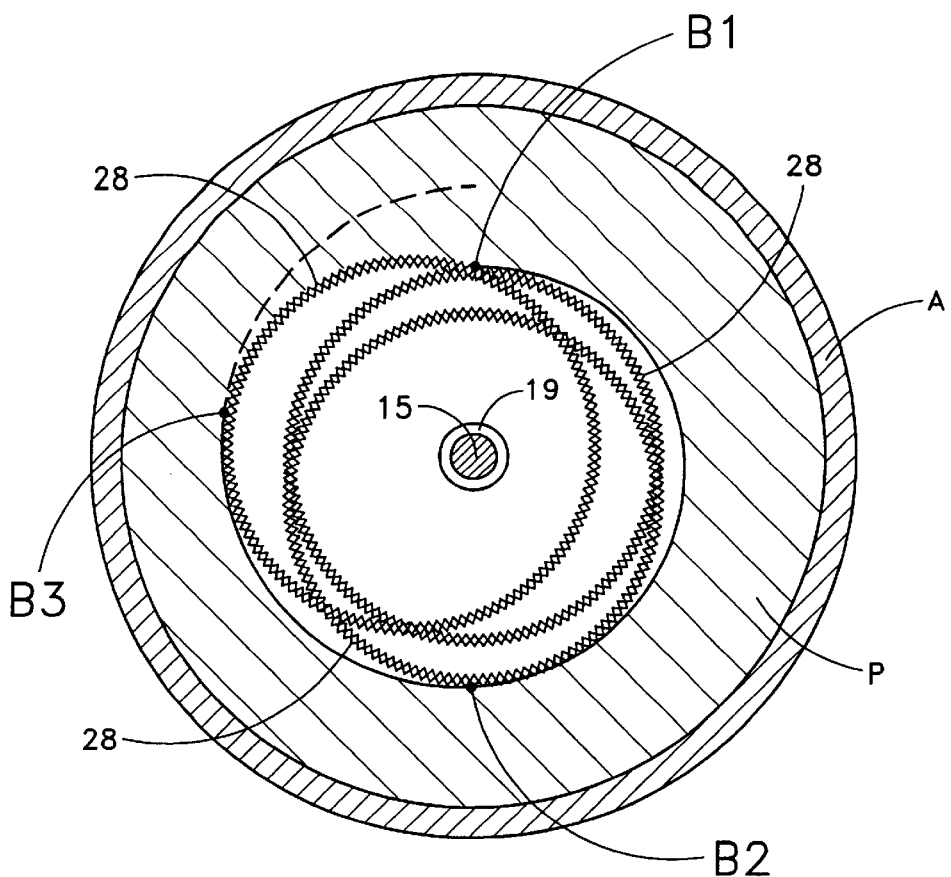
FIG. 15 is a transverse cross-sectional view similar to FIG. 14 illustrating three different positions of the rapidly rotating eccentric enlarged diameter section of an eccentric rotational atherectomy device of the invention.
Figure 16:
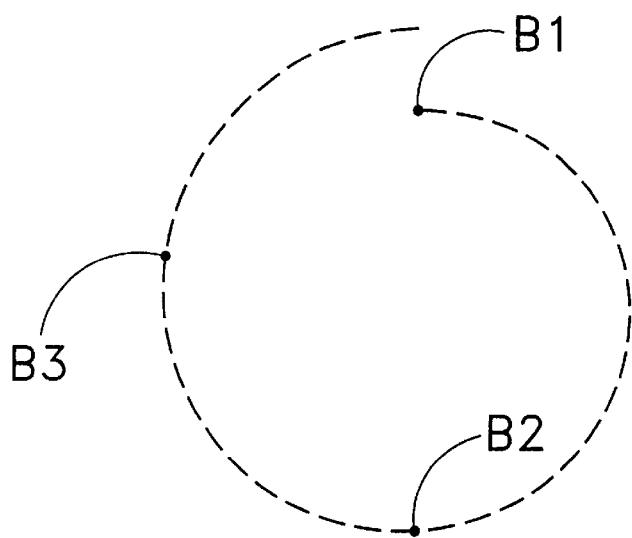
FIG. 16 is a schematic diagram illustrating in exaggerated fashion the spiral path taken by the eccentric enlarged diameter section as it removes stenotic tissue from an artery.

These advantages over the devices described above in the patents referred to in the background section are a result of the invention functioning differently than these prior art devices. That is, in the Auth '134 and Shturman '438 patents tissue is removed by a single distal pass of the atherectomy device through the stenosis (even though this pass may be made up of repeated distal strokes of the device)—the abrasive surface being primarily on the "front" of such devices. The pressure of the abrading surface on the plaque in these prior art devices is entirely dependent on the distal force applied by the operator. In contrast, FIGS. 15–16 illustrate the generally spiral path taken by the side-abrading device of the invention. The pitch of the spiral path in FIG. 15–16 is exaggerated for illustrative purposes—in reality, each spiral path of the eccentric enlarged diameter section 28 removes only a very thin layer of tissue, and many, many such spiral passes are made by the eccentric enlarged diameter section as the device is repeatedly moved forward and backward across the stenosis to fully open the stenosis. FIG. 15 shows schematically three different rotational positions of the eccentric enlarged diameter section 28 of a rotational atherectomy device of the invention. At each position the abrasive surface of the eccentric enlarged diameter section 28 contacts the plaque "P" to be removed—the three positions are identified by three different points of contact with the plaque "P", those points being designated in the drawing as points B1, B2, and B3. Notice that at each point it is generally the same portion of the abrasive surface of the eccentric enlarged diameter section 28 that contacts the tissue—the portion of the abrasive surface that is radially most distant from the rotational axis of the drive shaft.

Figure 17:
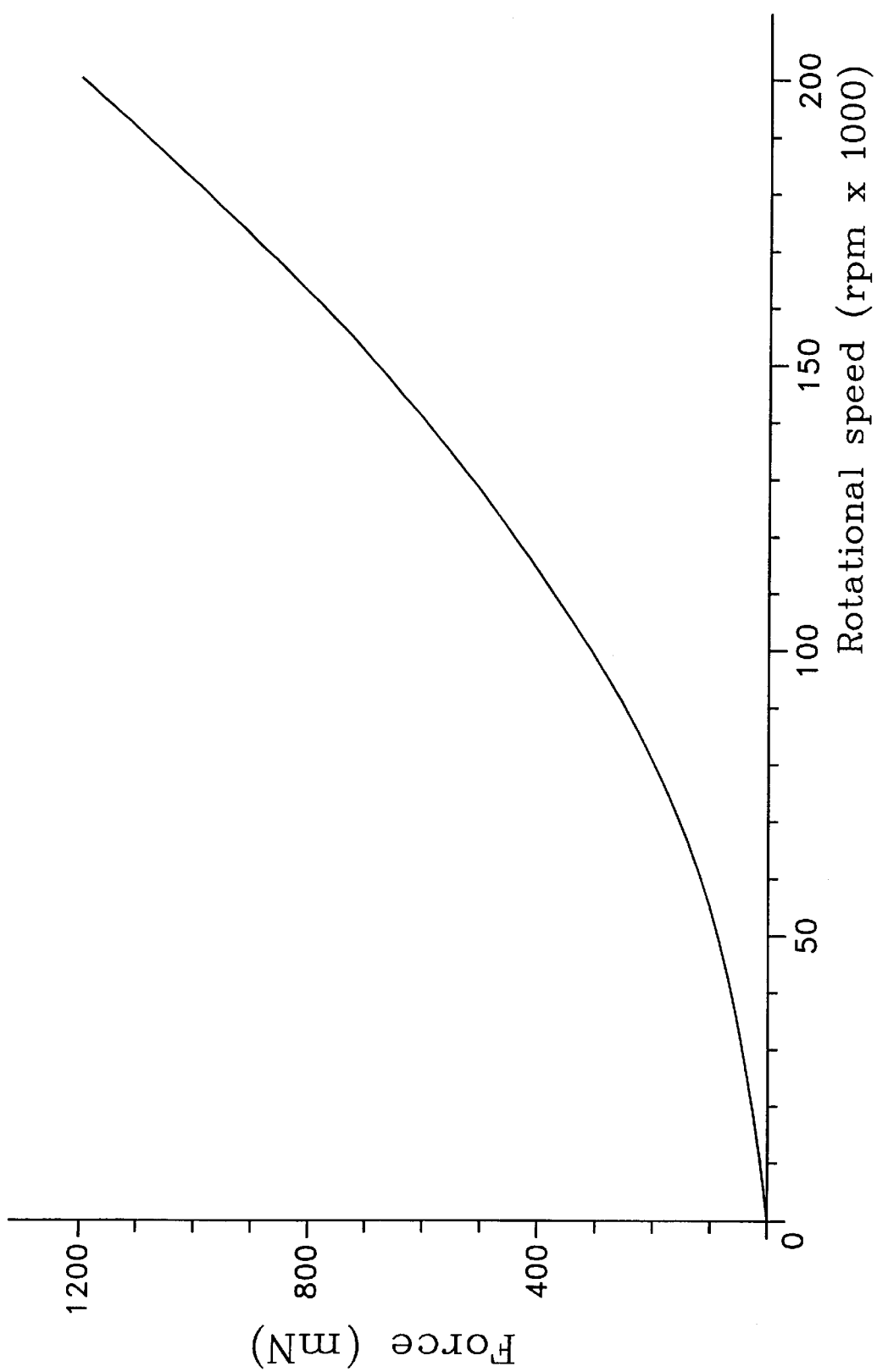
FIG. 17 is a graph illustrating the maximum centrifugal force with which a tissue removing surface of an eccentric enlarged diameter section, having a maximum diameter of about 1.75 mm, can press against a surface of a stenosis at various speeds of rotation.

Although not wishing to be constrained to any particular theory of operation, applicants believe that offsetting the center of mass from the axis of rotation produces an "orbital" movement of the enlarged diameter section of the drive shaft, the diameter of the "orbit" being controllable by varying the rotational speed of the drive shaft. Whether or not the "orbital" movement is as geometrically regular as is shown in FIGS. 15–16 has not been determined, but applicants have empirically demonstrated that by varying the rotational speed of the drive shaft one can control the centrifugal force urging the tissue removing surface of the eccentric enlarged diameter section against the surface of the stenosis. The centrifugal force can be determined according to the formula $$F_c = m \cdot \Delta x \cdot (\pi \cdot n/30)^2$$

where $F_c$ is the centrifugal force, m is the mass of the eccentric enlarged diameter section, $\Delta x$ is the distance between the center of mass of the eccentric enlarged diameter section and the rotational axis of the drive shaft, and n is the rotational speed in revolutions per minute (rpm). The graph shown in FIG. 17 illustrates calculations of the maximum centrifugal force $F_c$ with which a tissue removing surface of an eccentric enlarged diameter section, having a maximum diameter of about 1.75 mm, can press against a surface of a stenosis at rotational speeds up to about 200,000 rpm. Controlling this force $F_c$ provides control over the rapidity with which tissue is removed, control over the maximum diameter to which the device will open a stenosis, and improved control over the particle size of the tissue being removed.

Using the rotational atherectomy device of the invention the operator repeatedly moves the eccentric enlarged diameter section 28 distally and proximally through the stenosis. By changing the rotational speed of the device he is able to control the force with which the tissue removal surface is pressed against the stenotic tissue, thereby being able to better control the speed of the plaque removal as well as the particle size of tissue removed. Since the stenosis is being opened to a diameter larger than the nominal diameter of the enlarged diameter section, the cooling solution and the blood are able to constantly flow around the enlarged diameter section. Such constant flow of blood and cooling solution constantly flushes away removed tissue particles, thus providing more uniform release of removed particles than the Auth and Shturman devices referred to above.

Figure 18:
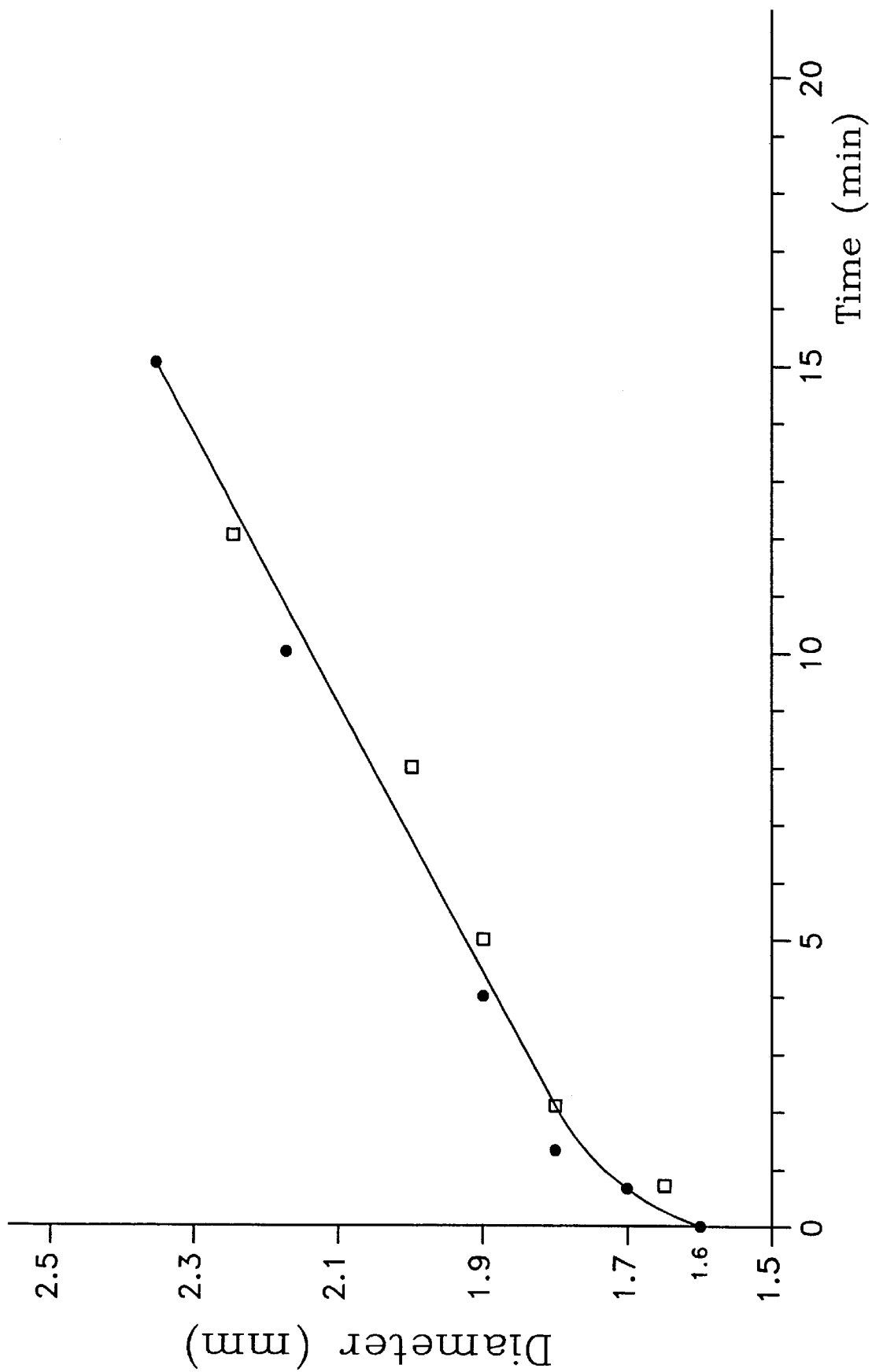
FIG. 18 is a graph of experimental data illustrating the extent to which the eccentric enlarged diameter section, having a maximum diameter of about 1.57 mm opens a 1.6 mm passageway to a progressively larger diameter as the eccentric atherectomy device is given more time to work.

FIG. 18 depicts experimental data of an eccentric enlarged diameter section having a nominal diameter of 1.57 mm being used to open a passageway in calcite (a stone comprised predominantly of $CaCO_3$) at a rotational speed of about 180,000 rpm. The experiment was initiated on test stones having 10 mm long passageways with diameters of 1.6 mm. The dots and squares represent two sets of data from two independent tests, and show that the eccentric enlarged diameter section, having a nominal diameter of 1.57 mm, was able to open the passageways to a diameter of about 2.3 mm. The data illustrate the time dependence of the procedure—i.e., an operator can control the diameter to which the stenosis will be opened by controlling the length of time the eccentric enlarged diameter section is rotated within the stenosis. The data also illustrate the ability of the device to open a stenosis to a diameter substantially larger than the nominal diameter of the eccentric enlarged diameter section.

Figure 19:
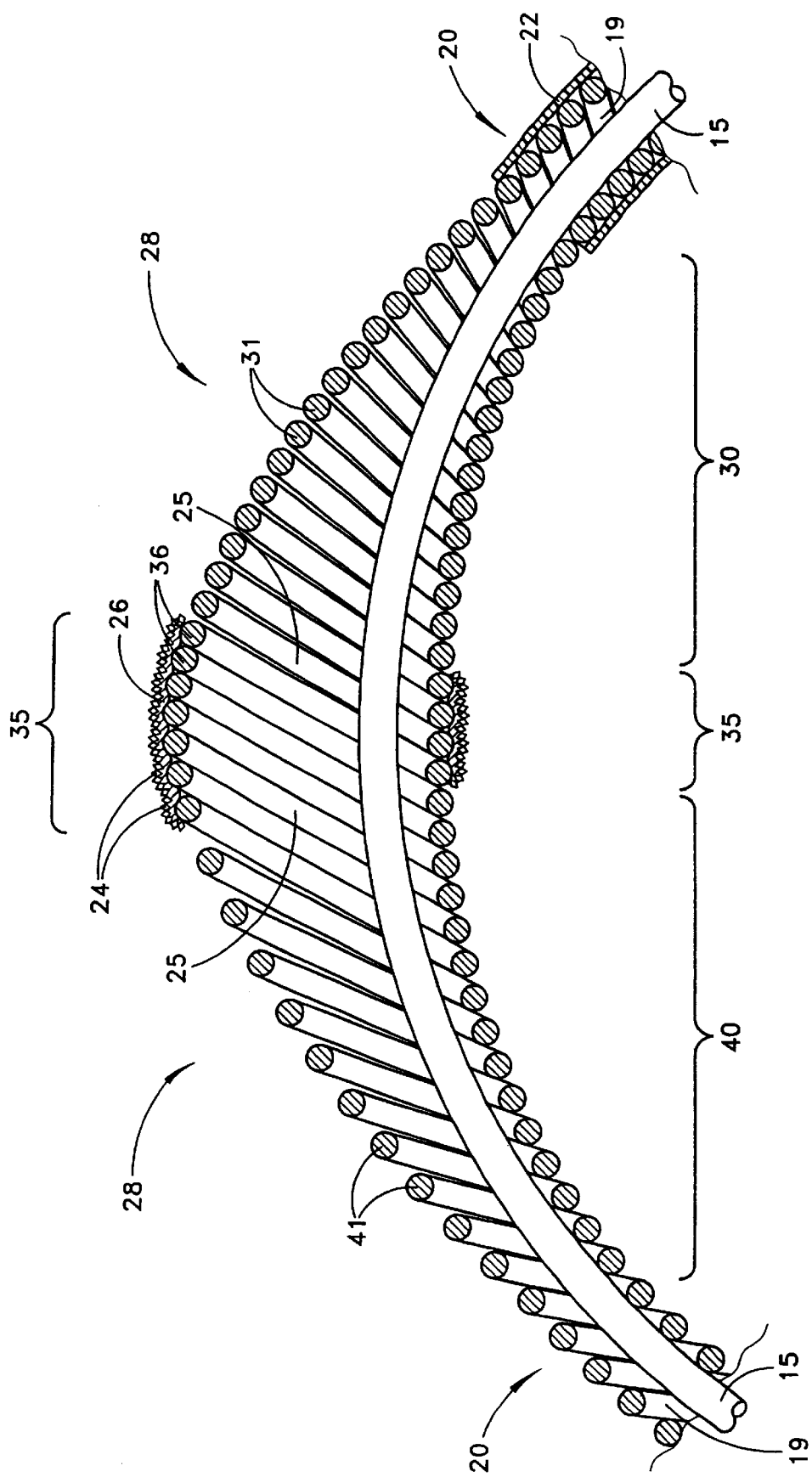
FIG. 19 is broken-away, longitudinal cross-sectional view similar to FIG. 3 illustrating the flexibility of the eccentric enlarged diameter section of the atherectomy device of the invention.

FIG. 19 illustrates the flexibility of the eccentric enlarged diameter section 28 of the invention. In the embodiment shown in this drawing adjacent wire turns of the intermediate portion 35 of the eccentric enlarged diameter section of the drive shaft are secured to one another by the binding material 26 securing the abrasive particles 24 to the wire turns 36. Adjacent wire turns of the proximal 30 and distal 40 portions of the eccentric enlarged diameter section of the drive shaft are not secured to one another, thereby permitting such portions of the drive shaft to flex, as shown in the drawing. Such flexibility facilitates advancement of the device through relatively tortuous passageways. If desired, adjacent wire turns of even the intermediate portion 35 of the eccentric enlarged diameter section 28 of the drive shaft may be not secured to one another, thereby providing even greater flexibility.

Figure 20:
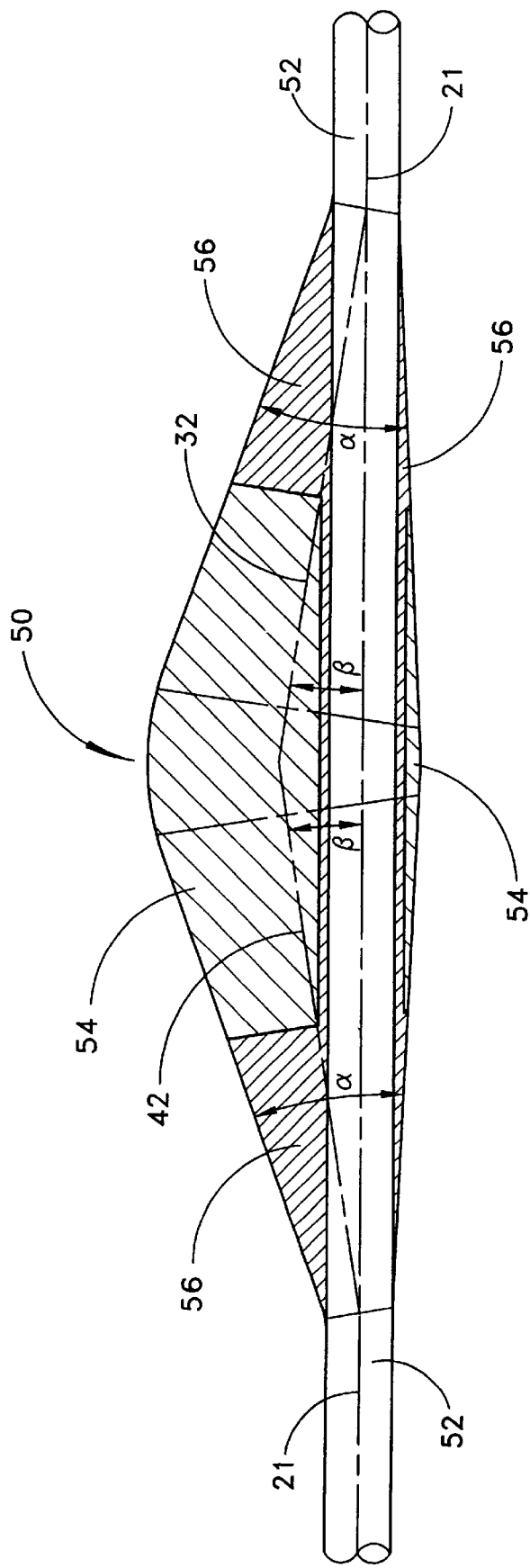
FIG. 20 is a broken-away, longitudinal cross-sectional view of a mandrel used in manufacturing an eccentric rotational atherectomy device of the invention.
Figure 21:
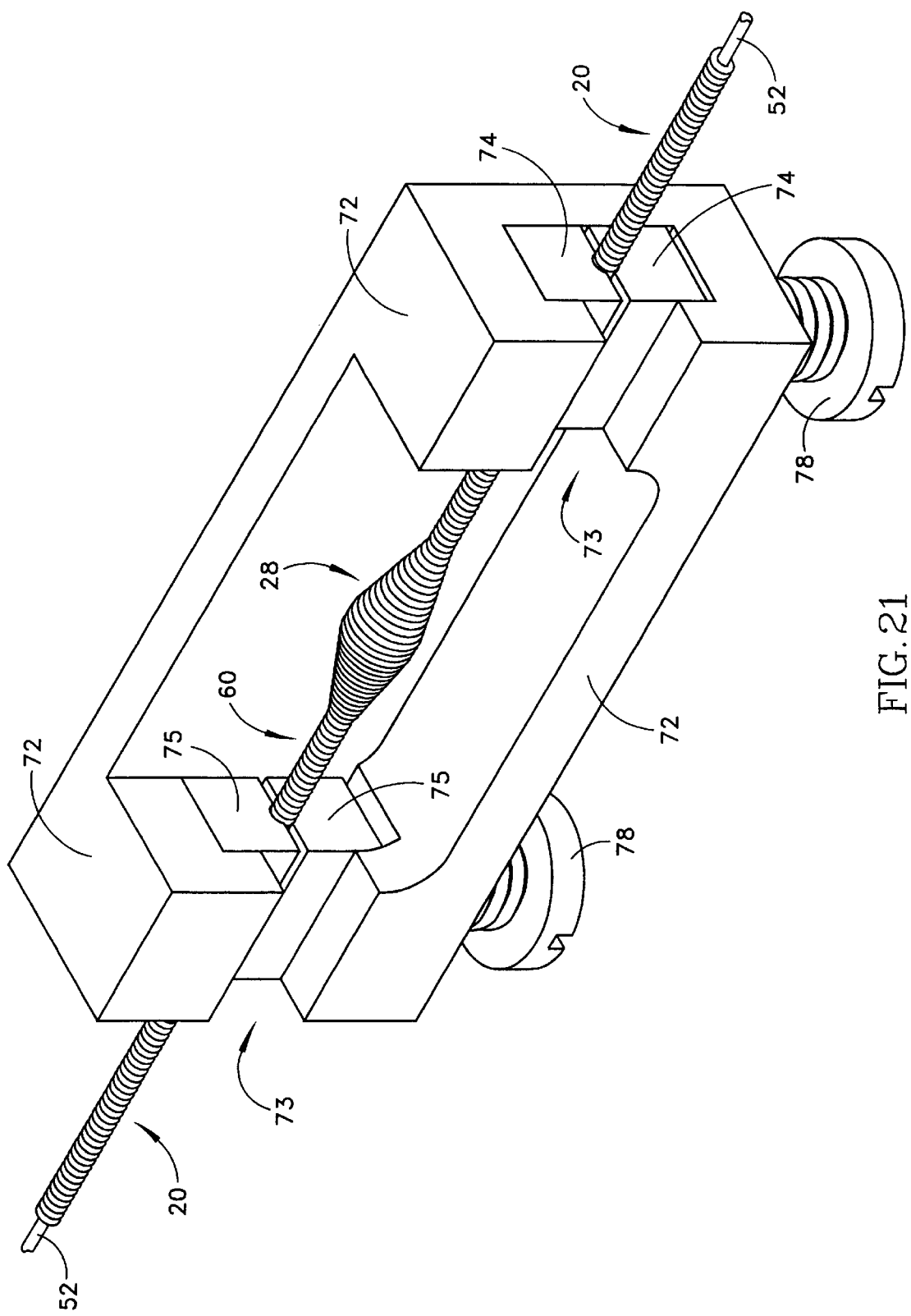
FIG. 21 is a perspective view of a clamp used in manufacturing an eccentric rotational atherectomy device of the invention.

Helically wound multifilar drive shafts usable in the invention may be manufactured by winding suitable wires about a mandrel. FIG. 20 depicts a mandrel 50 usable to manufacture the eccentric enlarged diameter section 28 of the atherectomy device depicted in FIGS. 2—5. The mandrel 50 includes a mandrel shaft 52 having a generally constant diameter along its entire length. An eccentric enlarged diameter component 54 of the mandrel may be machined from suitable material, such as brass (e.g., round brass rod sold by Vincent Metals, of Minneapolis, Minn. as "low leaded" brass rod comprised of 62.0% copper, 36.2% zinc and 1.8% lead, or "high speed-free cutting" brass rod comprised of 61.5% copper, 35.5% zinc and 3.0% lead). The eccentric enlarged diameter component 54 is disposed on the mandrel shaft 52 at the desired location, and is then secured in place with a suitable material, such as solder 56. Preferably the solder composition is 61% tin and 39% lead. The flux used in soldering the eccentric enlarged diameter component 54 to the mandrel shaft 52 preferably is comprised of 75% $ZnCl_2$ and 25% $NH_4Cl$, these compounds being dissolved in distilled water at maximum concentration (i.e., creating a saturated solution). The solder joint may be further machined or sanded to achieve a smooth transition between the eccentric enlarged diameter component 54 and the mandrel shaft 52.

After the mandrel 50 is so constructed, suitable wires may be wound about the mandrel 50, including both the mandrel shaft 52 and the eccentric enlarged diameter component 54. Before the winding tension on the wires has been released, a clamp 72 (shown in FIGS. 21–24) is secured on the drive shaft at the appropriate location. The clamp includes a clamp frame 72 with a slot 73, two sets of clamping blocks 74 and 75, and a pair of set screws 78. Fixation of the clamp on the drive shaft is accomplished by first passing the drive shaft through the slot 73 in the clamp frame 72, next positioning the clamping blocks 74 and 75 about the drive shaft 20 and moving them into the clamp frame 72, and finally tightening set screws 78 to firmly clench the drive shaft with its eccentric enlarged diameter section 28 between the clamping blocks 74 and 75. Once the set screws 78 are tightened, the winding tension on the drive shaft wires may be released. Those portions of the drive shaft wires not captured by the clamp will unwind to a diameter slightly larger than the mandrel, but the clamp will prevent such unwinding for the entire portion of the drive shaft located between the two sets of clamping blocks 74 and 75. Clamping blocks 74 and 75 preferably are made from a relatively soft metal such as nickel.

FIG. 22 illustrates in longitudinal cross-section how the drive shaft 20 is clenched by clamping blocks 74 and 75. In FIGS. 22 and 23 the portions of the drive shaft not captured by the clamp are shown as having unwound to a diameter larger than the diameter of the portion captured by the clamp. FIG. 23, however, significantly exaggerates the degree of unwinding—typically the outer diameter of the drive shaft, as a result of unwinding, will increase by only about 2–10%.

Once the clamp has been secured to the drive shaft and the portions of the drive shaft not captured by the clamp are allowed to unwind to a slightly larger diameter, then the distal length of the drive shaft, together with the clamp, is heat treated to give the wires of the drive shaft the desired "set." Only the distal length of the drive shaft, including the section of the drive shaft which is distal to the enlarged diameter section 28, the enlarged diameter section 28 itself, and about 80 mm of the drive shaft's length proximal to the eccentric enlarged diameter section 28 need be placed in the heat treatment oven.

Preferably the heat treatment is in the range of about 500° C. to about 560° C. for about 30–60 minutes to give the wires the desired set. The particular temperature selected will depend on the maximum diameter of the eccentric enlarged diameter section. Applicants have successfully used stainless steel wire with a diameter of about 0.006 inches for drive shafts having eccentric enlarged diameter sections with diameters of up to about 2.2 mm. Applicants have successfully used type 304 stainless steel wire available from Fort Wayne Metals Research Products Corp. (Fort Wayne, Indiana) under the name "Hyten." Preferably the wire has a tensile strength of about 445±10 ksi.

After the heat treatment has been completed and both the drive shaft 20 and the clamp have cooled, the drive shaft is removed from the clamp. The mandrel 50 is then removed from the drive shaft. Applicants have found that the mandrel 50 may be removed by constructing the components of the mandrel 50 from materials different from the drive shaft wire so that the mandrel components may be dissolved in appropriate solutions which do not materially adversely affect the drive shaft itself. For example, the mandrel shaft 52 may be made from high carbon steel, the eccentric enlarged diameter portion 54 from brass (as described above), and the helically wound wire from the "Hyten" stainless steel wire mentioned above. The entire drive shaft, together with the mandrel 50, is immersed in a 15% solution of hot nitric acid (typically at about 80–100° C.) for about 8–10 hours until the mandrel shaft 52 is completely dissolved. Applicants have found that the process of dissolving the mandrel shaft 52 usually is completed when gas bubbles stop rising to the surface of the nitric acid. As with the heat treatment process described above, preferably the drive shaft is kept generally straight when immersed in the hot nitric acid. Alternately, the drive shaft may be coiled, but, in that event, the diameter of the coil preferably should be not less than about seven or eight inches, because the heat of this process can also affect the shape of the drive shaft.

After the mandrel shaft 52 has been dissolved, the distal portion of the drive shaft, together with the enlarged diameter portion 54 of the mandrel (which has not yet been dissolved), preferably including at least a short section of the drive shaft proximal to the enlarged diameter section, is immersed in a 35% solution of hot nitric acid (typically at about 80–100° C.) for 8–10 hours to dissolve the enlarged diameter portion 54 of the mandrel and the solder 56.

Immediately after removing the drive shaft from this second immersion into nitric acid the: drive shaft is washed for several minutes in running water. The drive shaft then is placed into boiling distilled water for 15–20 minutes, and then dipped into 96% alcohol and air dried or wiped with a clean cloth.

Following these procedures, the entire drive shaft may be heat treated for the second time at temperatures ranging from 200 to 300° C. to relieve stress in the wire turns of the drive shaft. The drive shaft then is finished by electropolishing.

If desired, the eccentricity of the enlarged diameter section can be increased by placing the enlarged diameter section in a form having the desired shape, and then heat treating the enlarged diameter section to give it the new, more eccentric shape. Alternately, the enlarged diameter section may initially be constructed by winding the wire about a mandrel having a symmetrical (i.e., non-eccentric) enlarged diameter component, placing the resultant symmetrical enlarged diameter section in an eccentric form, and heat treating the enlarged diameter section to give it the desired eccentric shape.

The foregoing procedures may be utilized to make eccentric atherectomy devices of various desired diameters. Because, as described above, the eccentricity of the enlarged diameter section is dependent on a number of parameters, applicants have found that the following design parameters may be considered regarding the distance between the rotational axis of the drive shaft and the geometric center of a face of a transverse cross-section, taken at a position of maximum cross-sectional diameter of the eccentric enlarged diameter section: for a device having an eccentric enlarged diameter section with a maximum cross-sectional diameter between about 1.0 mm and about 1.5 mm, desirably the geometric center should be spaced away from the rotational axis of the drive shaft by a distance of at least about 0.02 mm, and preferably by a distance of at least about 0.035 mm; for a device having an eccentric enlarged diameter section with a maximum cross-sectional diameter between about 1.5 mm and about 1.75 mm, desirably the geometric center should be spaced away from the rotational axis of the drive shaft by a distance of at least about 0.05 mm, preferably by a distance of at least about 0.07 mm, and most preferably by a distance of at least about 0.09 mm; for a device having an eccentric enlarged diameter section with a maximum cross-sectional diameter between about 1.75 mm and about 2.0 mm, desirably the geometric center should be spaced away from the rotational axis of the drive shaft by a distance of at least about 0.1 mm, preferably by a distance of at least about 0.15 mm, and most preferably by a distance of at least about 0.2 mm; and for a device having an eccentric enlarged diameter section with a maximum cross-sectional diameter above 2.0 mm, desirably the geometric center should be spaced away from the rotational axis of the drive shaft by a distance of at least about 0.1 5 mm, preferably by a distance of at least about 0.25 mm, and most preferably by a distance of at least about 0.3 mm Design parameters can also be based on the location of the center of mass. For a device having an eccentric enlarged diameter section with a maximum cross-sectional diameter between about 1.0 mm and about 1.5 mm, desirably the center of mass should be spaced away from the rotational axis of the drive shaft by a distance of at least about 0.013 mm, and preferably by a distance of at least about 0.02 mm; for a device having an eccentric enlarged diameter section with a maximum cross-sectional diameter between about 1.5 mm and about 1.75 mm, desirably the center of mass should be spaced away from the rotational axis of the drive shaft by a distance of at least about 0.03 mm, and preferably by a distance of at least about 0.05 mm; for a device having an eccentric enlarged diameter section with a maximum cross-sectional diameter between about 1.75 mm and about 2.0 mm, desirably the center of mass should be spaced away from the rotational axis of the drive shaft by a distance of at least about 0.06 mm, and preferably by a distance of at least about 0.1 mm; and for a device having an eccentric enlarged diameter section with a maximum cross-sectional diameter above 2. 0mm, desirably the center of mass should be spaced away from the rotational axis of the drive shaft by a distance of at least about 0.1 mm, and preferably by a distance of at least about 0.16 mm.

Preferably the design parameters are selected so that the enlarged diameter section is sufficiently eccentric that, when rotated over a stationary guide wire (held sufficiently taut so as to preclude any substantial movement of the guide wire) at a rotational speed of not more than 60 rpm, at least a portion of its tissue removing surface rotates through a path (whether or not such path is perfectly regular or circular) having a diameter larger than the maximum nominal diameter of the eccentric enlarged diameter section (e.g., for an enlarged diameter section having a maximum diameter between about 1.5 mm and about 1.75 mm, at least a portion of the tissue removal section should rotate through a path having a diameter at least about 10% larger than the maximum nominal diameter of the eccentric enlarged diameter section, preferably at least about 15% larger than the maximum nominal diameter of the eccentric enlarged diameter section, and most preferably at least about 20% larger than the maximum nominal diameter of the eccentric enlarged diameter section; for an enlarged diameter section having a maximum diameter between about 1.75 mm and about 2.0 mm, at least a portion of the tissue removal section should rotate through a path having a diameter at least about 20% larger than the maximum nominal diameter of the eccentric enlarged diameter section, preferably at least about 25% larger than the maximum nominal diameter of the eccentric enlarged diameter section, and most preferably at least about 30% larger than the maximum nominal diameter of the eccentric enlarged diameter section; and for an enlarged diameter section having a maximum diameter of at least about 2.0 mm, at least a portion of the tissue removal section should rotate through a path having a diameter at least about 30% larger than the maximum nominal diameter of the eccentric enlarged diameter section, and preferably at least about 40% larger than the maximum nominal diameter of the eccentric enlarged diameter section).

Preferably design parameters are selected so that the enlarged diameter section is sufficiently eccentric that, when rotated over a stationary guide wire at a speed between about 20,000 rpm and about 200,000 rpm, at least a portion of its tissue removing surface rotates through a path (whether or not such path is perfectly regular or circular) substantially larger than the maximum nominal diameter of the eccentric enlarged diameter section. Desirably such path is at least about 30% larger than the maximum nominal diameter of the eccentric enlarged diameter section, preferably the path is at least about 50% larger than the maximum nominal diameter of the eccentric enlarged diameter section, and most preferably the path is at least about 70% larger than the maximum nominal diameter of the eccentric enlarged diameter section.

Figure 25:
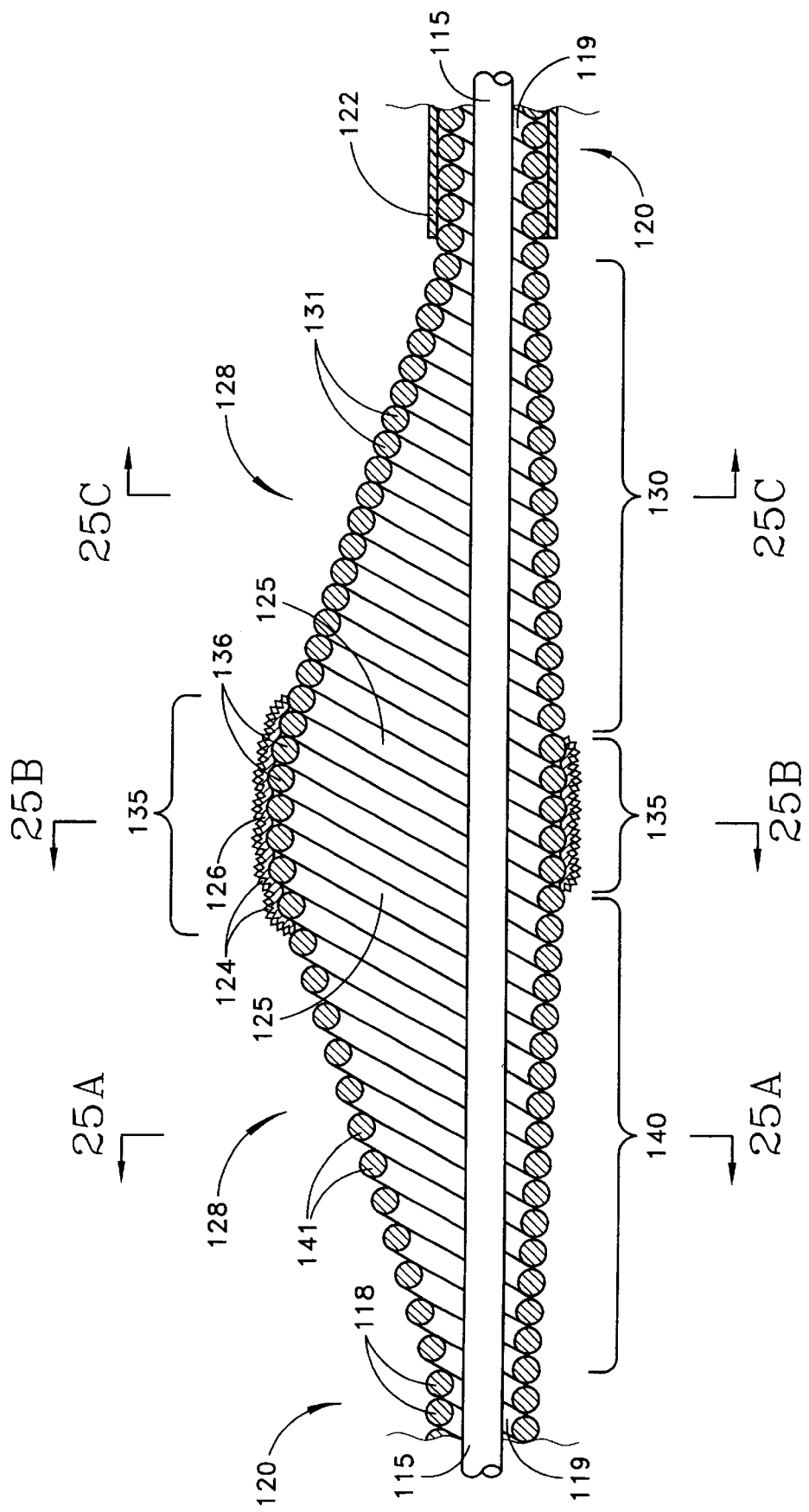
FIG. 25 is a longitudinal cross-sectional view of an alternate embodiment of the invention employing a slightly differently shaped eccentric enlarged diameter section.
Figures 25A, 25B, 25C:
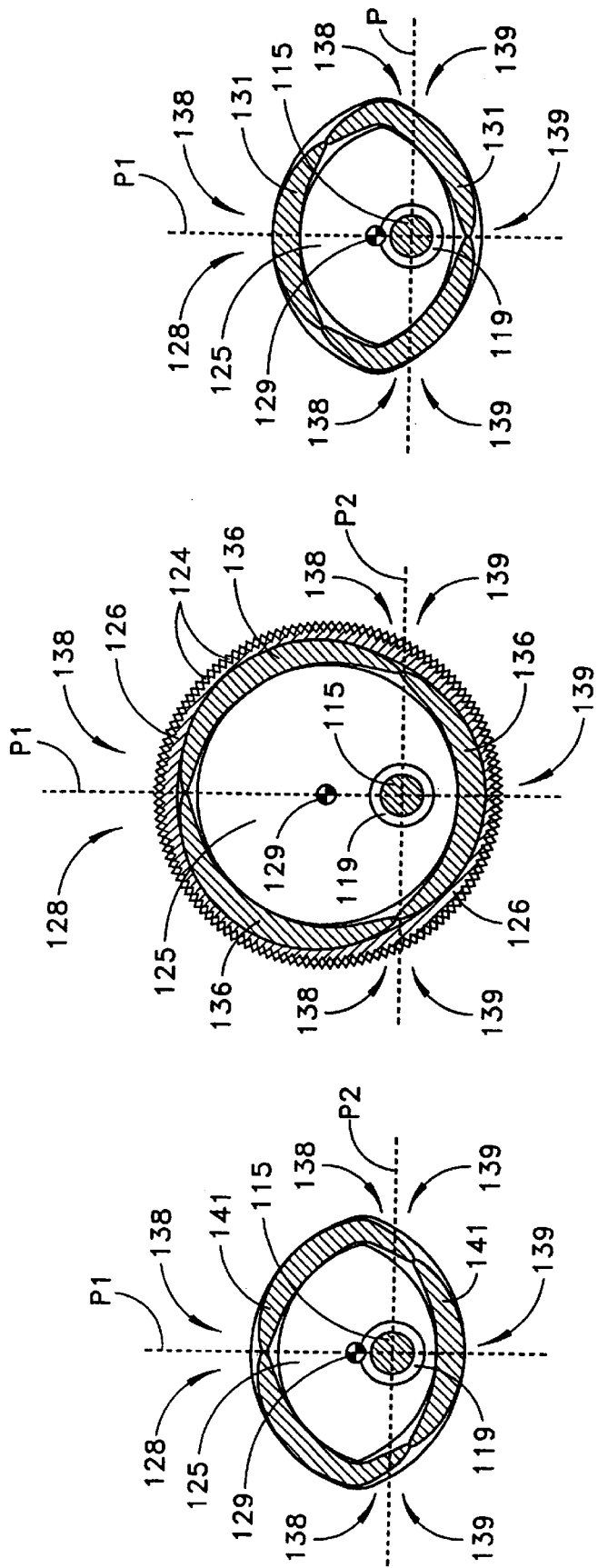
FIGS. 25A–25C are transverse cross-sectional views of FIG. 25, taken along lines 25A—25A through 25C—25C thereof.

FIGS. 25–25C depict a modified embodiment of an eccentric enlarged diameter section 128 of the invention. (Reference numbers in FIGS. 25–30 are in the 100 series, but otherwise generally correspond to those utilized in FIGS. 1–24.) The general shape, and, particularly, the longitudinal cross-sectional profile of the eccentric enlarged diameter section 128, is substantially similar to the general shape and the longitudinal cross-sectional profile of the bi-conical eccentric enlarged diameter section 28 of FIGS. 3–4. The proximal 130 and distal 140 portions of the eccentric enlarged diameter section 128 are substantially equal in length and are mirror images of each other, being generally symmetrical with respect to a plane which passes through the intermediate portion 135 of the eccentric enlarged diameter section 128 and is generally perpendicular to the rotational axis of the drive shaft. The difference between the eccentric enlarged diameter section 128 and the eccentric enlarged diameter section 28 may be seen by comparing the transverse cross-sectional profiles of the proximal 130 and distal 140 portions of the enlarged diameter section 128 (shown in FIGS. 25A and 25C) to the transverse cross-sectional profiles of corresponding portions of the eccentric enlarged diameter section 28 (shown in FIGS. 3A and 3C).

Figure 26:
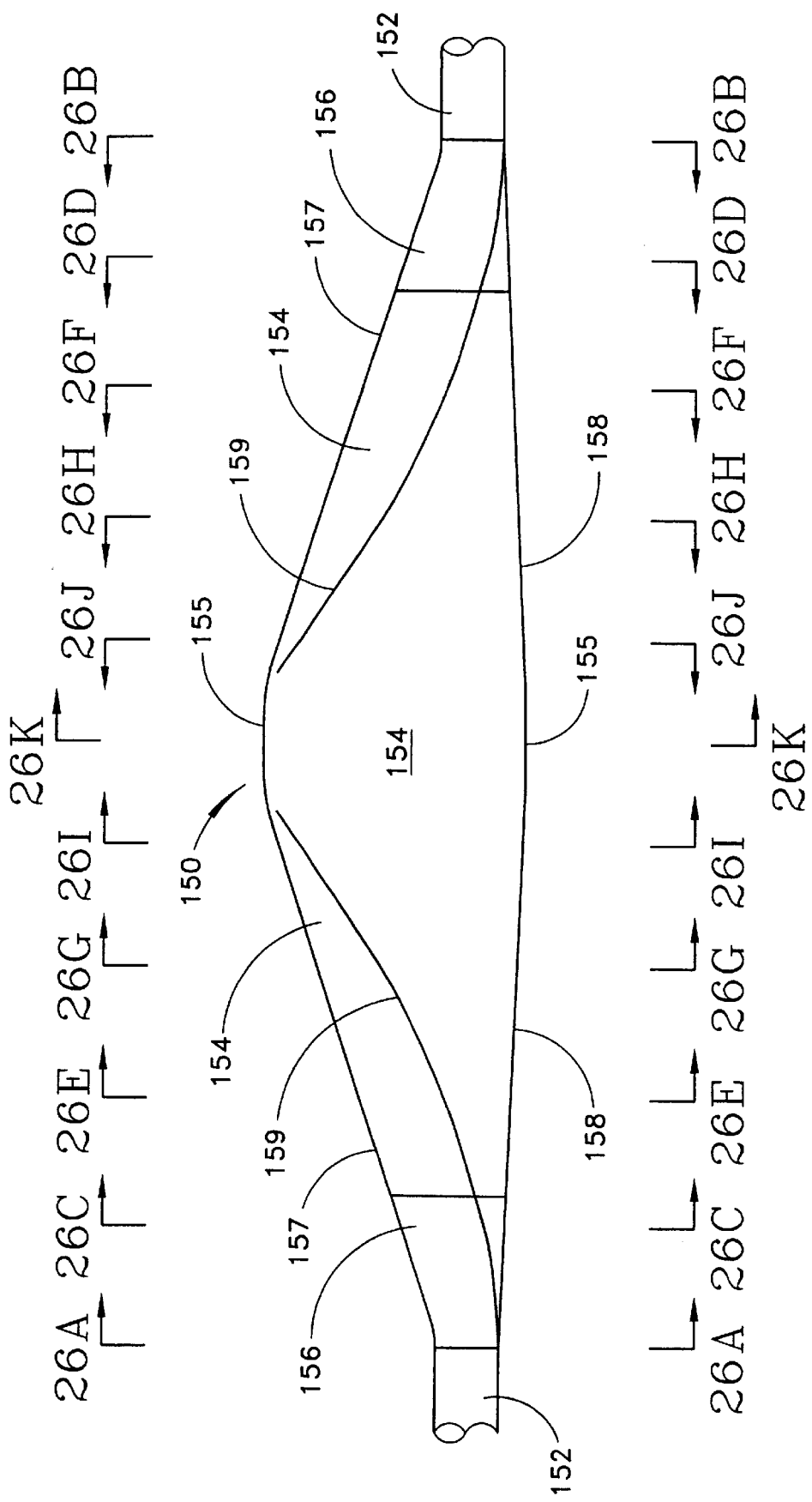
FIG. 26 is a side, broken-away view of a mandrel which can be used to manufacture the eccentric rotational atherectomy device of FIG. 25.
Figure 26G:
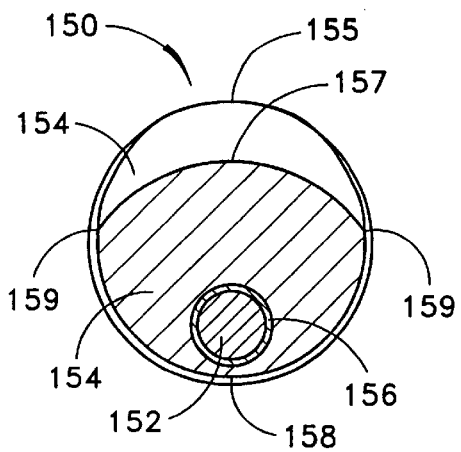
Figure 26H:
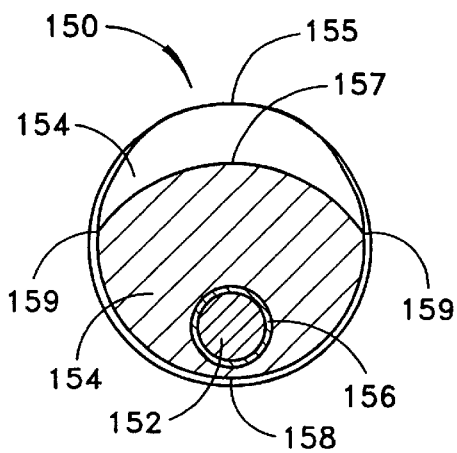
Figure 26I:
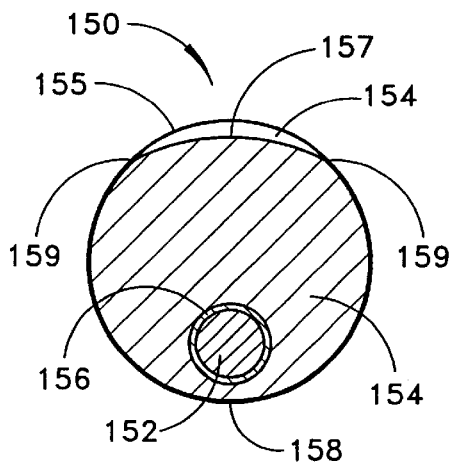
Figure 26J:
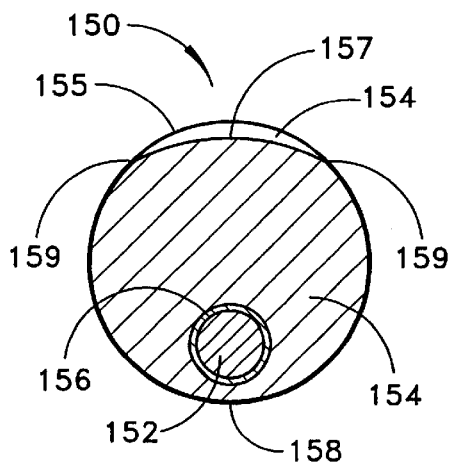
Figure 26K:
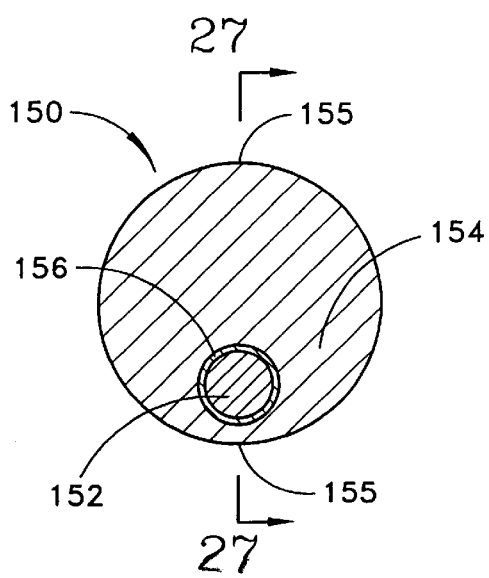
Figure 27:
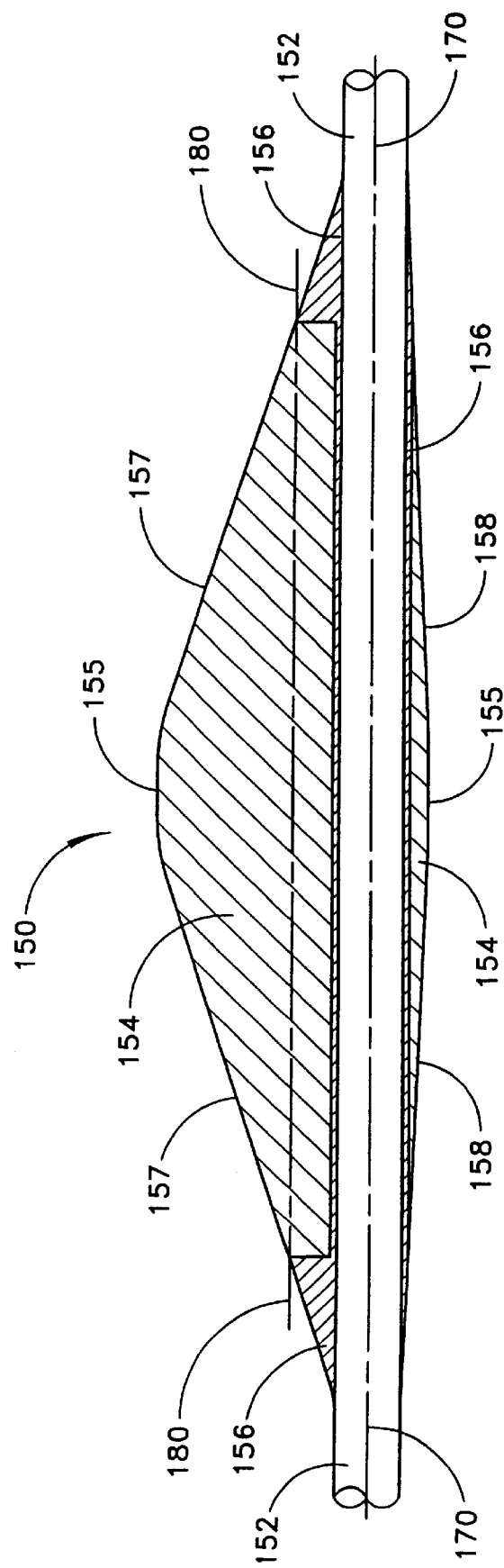
FIG. 27 is a longitudinal cross-sectional view of FIG. 26K, taken along lines 27—27 thereof.

The three-dimensional shape of the eccentric enlarged diameter section 128 can most easily be understood with reference to FIGS. 26–27, which illustrate a mandrel 150 that can be used in manufacturing the drive shaft 120 and the eccentric enlarged diameter section 128. The mandrel 150 includes a round mandrel shaft 152 and an eccentric enlarged diameter component 154. The eccentric enlarged diameter component 154 is secured to the mandrel shaft 152 with a suitable material, such as solder 156. All materials used in manufacturing the components of the mandrel 150 can be the same as the materials used to manufacture the corresponding components of the mandrel described above and shown in FIG. 20.

Figure 28:
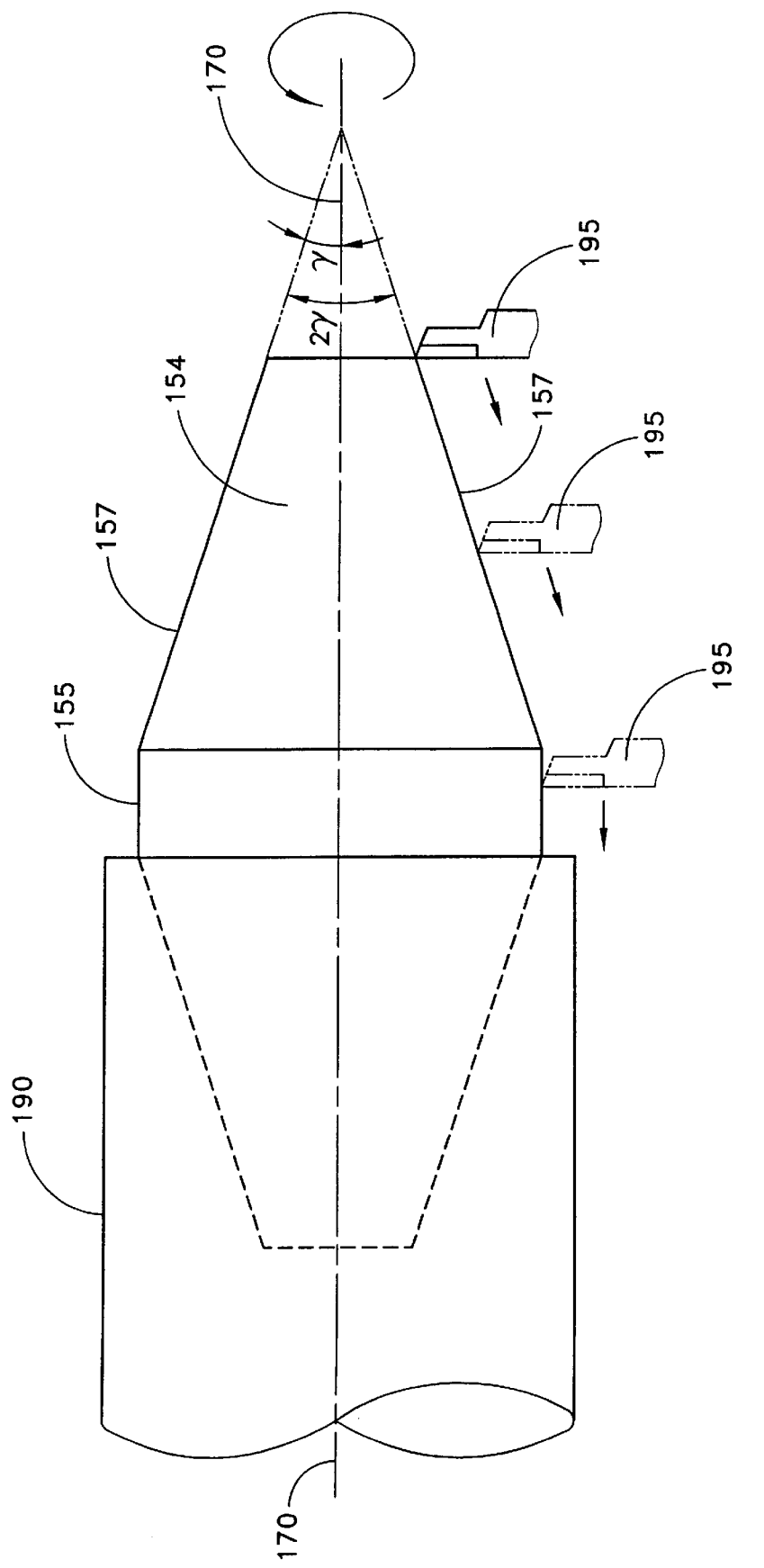

FIGS. 28–30 illustrate a preferred method of machining the eccentric enlarged diameter component 154 of the mandrel 150. These figures are also useful in understanding the three-dimensional shape of the eccentric enlarged diameter component 154 and the corresponding three-dimensional shape of the eccentric enlarged diameter section 128 of the drive shaft 120.

As with the proximal and distal portions of the eccentric enlarged diameter section 128, the corresponding proximal and distal portions of the eccentric enlarged diameter component 154 of the mandrel are not only equal in length but are also essentially mirror images of each other. Each portion has an outer surface comprised of at least two areas, a first of the two areas being substantially defined by a lateral surface of a frustum of a first cone 157, and a second of the two areas being substantially defined by a lateral surface of a frustum of a second cone 158. The junction of the conical surfaces of the first and second cones is shown as a line 159 in FIG. 26. Cross-sectional views 25A–25K also illustrate the surfaces of these cones. Both first cones 157 of the proximal and distal portions of the eccentric enlarged diameter component 154 have a common axis 170 (shown in FIGS. 27–30), which coincides with the axis of rotation of the drive shaft 120. Both second cones 158 of the proximal and distal portions of the eccentric enlarged diameter component 154 also have a common axis 180 (shown in FIGS. 27 and 29–30), which is parallel to and spaced away from the common axis 170 of the first cones 157 and, thus, the rotational axis of the drive shaft 120. The central bases of the second cones 158 of both the proximal and distal portions of the eccentric enlarged diameter component 154 have diameters that are generally equal to each other. These diameters are also equal to the diameter of the cylinder which substantially defines the outer surface 155 of the intermediate portion of the eccentric enlarged diameter component 154. The axis of this cylinder coincides with the common axis 180 of the second cones 158, thereby positioning the axis of the cylinder parallel to and spaced away from the rotational axis of the drive shaft 120. The shape of the cylinder may be modified, if desired, so that the corresponding intermediate portion of the eccentric enlarged diameter section has a surface which is shaped to provide a smooth transition between surfaces of the proximal and distal portions of the eccentric enlarged diameter section.

As mentioned above, FIGS. 28–30 illustrate a preferred method of machining the eccentric enlarged diameter component 154 of the mandrel. Preferably the eccentric enlarged diameter component 154 is machined from about 8 mm brass stock rod using a precision two spindle computer numerical controlled (CNC) lathe center. It is important that rotation of both spindles is synchronized in order to assure that both the proximal and distal portions of the eccentric enlarged diameter component 154 of the mandrel represent mirror images of each other. The "220 CNC" lather center sold by Schaublin (Switzerland) and the "CNC 230" lathe center sold by Ebosa (Switzerland) are both suitable for this purpose. The brass stock rod 190 is first rotated about an axis 170 and a cutting element 195 is moved along a path, the result of which is to give the stock 190 the combination of the conical 157 and cylindrical 155 shapes shown in FIG. 28. The stock 190 is then automatically remounted in the CNC lathe center so that it can be rotated around a second axis 180, parallel to but spaced away from the first axis 170, as is shown in FIGS. 29–30 (the eccentric enlarged diameter component 154 of the mandrel is shown rotated 180 degrees in FIG. 30 with respect to the position shown in FIG. 29). The cutting element 195 is then moved along a second path, the result of which is to add the second conical profile 158, resulting in the shape depicted in FIGS. 26–27. Preferably the angle γ formed between the lateral surface of the first cone 157 and the axis 170 of the first cone 157 is larger than the angle Φ formed between the lateral surface of the second cone 158 and the axis 180 of the second cone 158. The result of this reproducible machining process is an eccentric enlarged diameter component 154 usable for manufacturing the eccentric enlarged diameter section 128 of the atherectomy device depicted in FIGS. 25–25C.

Figure 31:
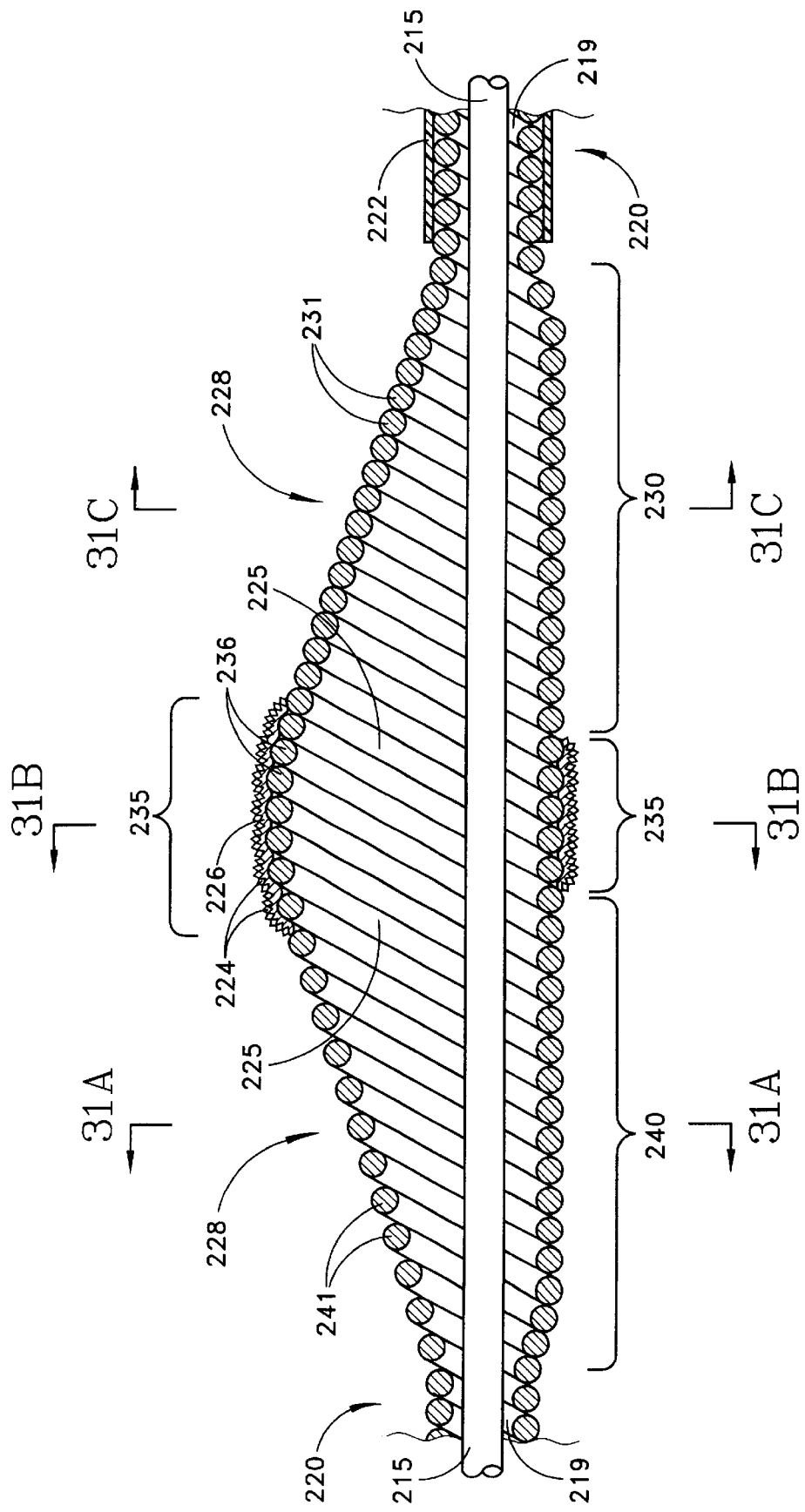
FIG. 31 is a longitudinal cross-sectional view of another alternate embodiment of the invention employing another differently shaped eccentric enlarged diameter section.
Figure 32:
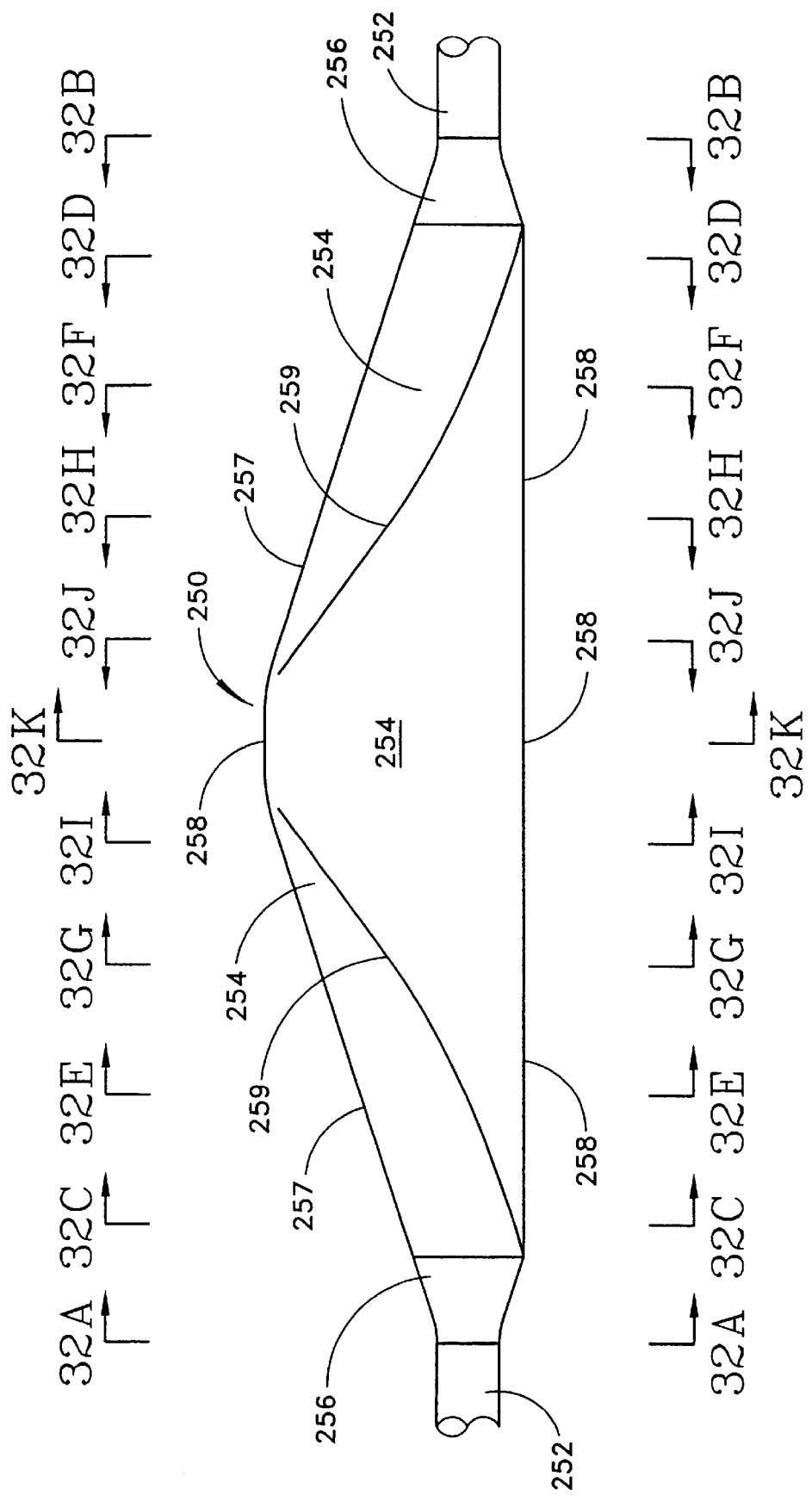
FIG. 32 is a side, broken-away view of a mandrel which can be used to manufacture the eccentric rotational atherectomy device of FIG. 31.
Figure 32A:
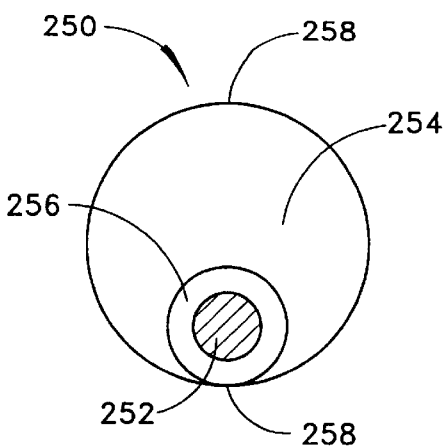
FIGS. 32A–32K are transverse cross-sectional views of FIG. 32, taken along lines 32A—32A through 32K—32K thereof.
Figure 32B:
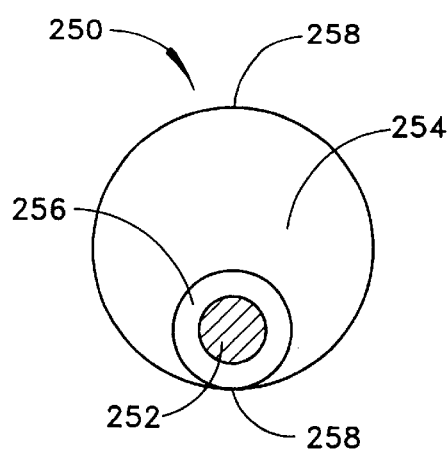
Figure 32C:
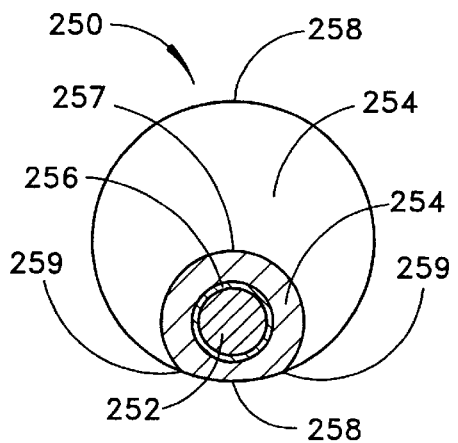
Figure 32D:
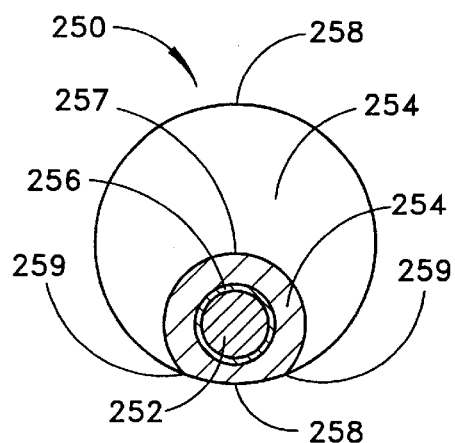
Figure 32E:
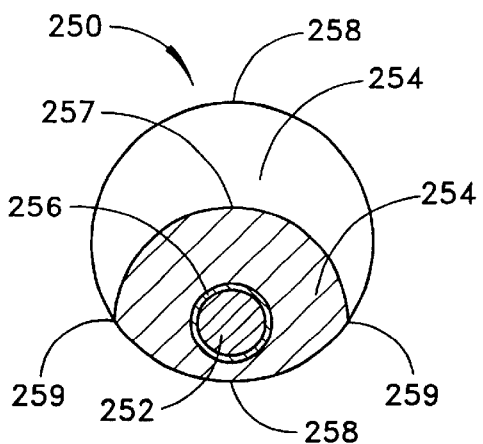
Figure 32F:
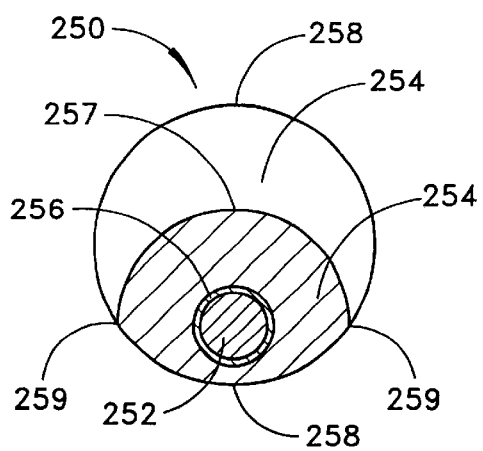
Figure 32G:
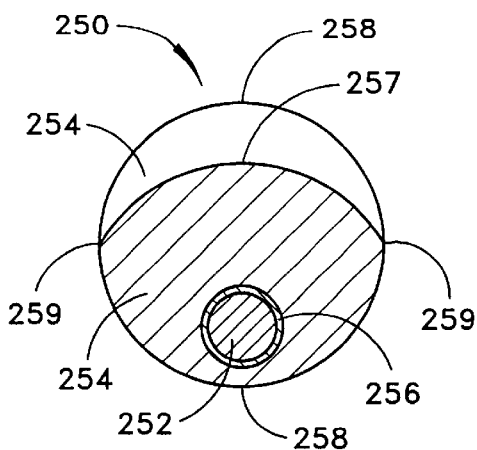
Figure 32H:
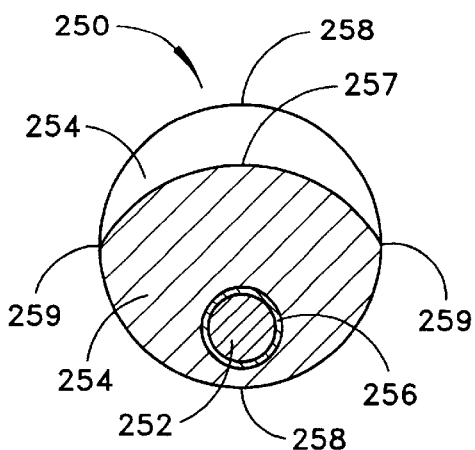
Figure 32I:
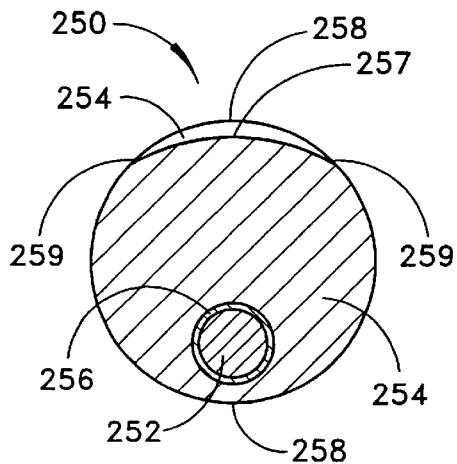
Figure 32J:
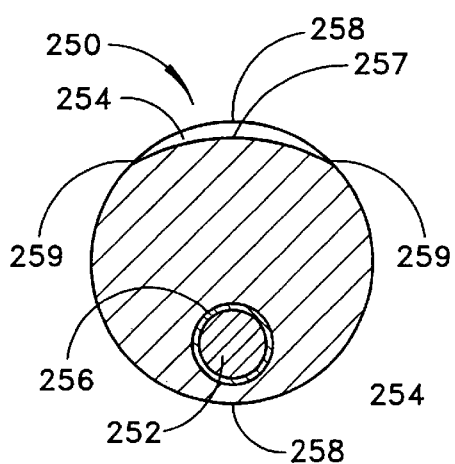
Figure 32K:
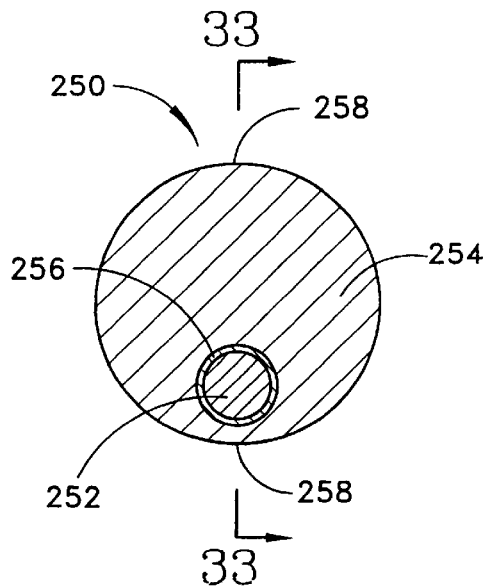
Figure 33:
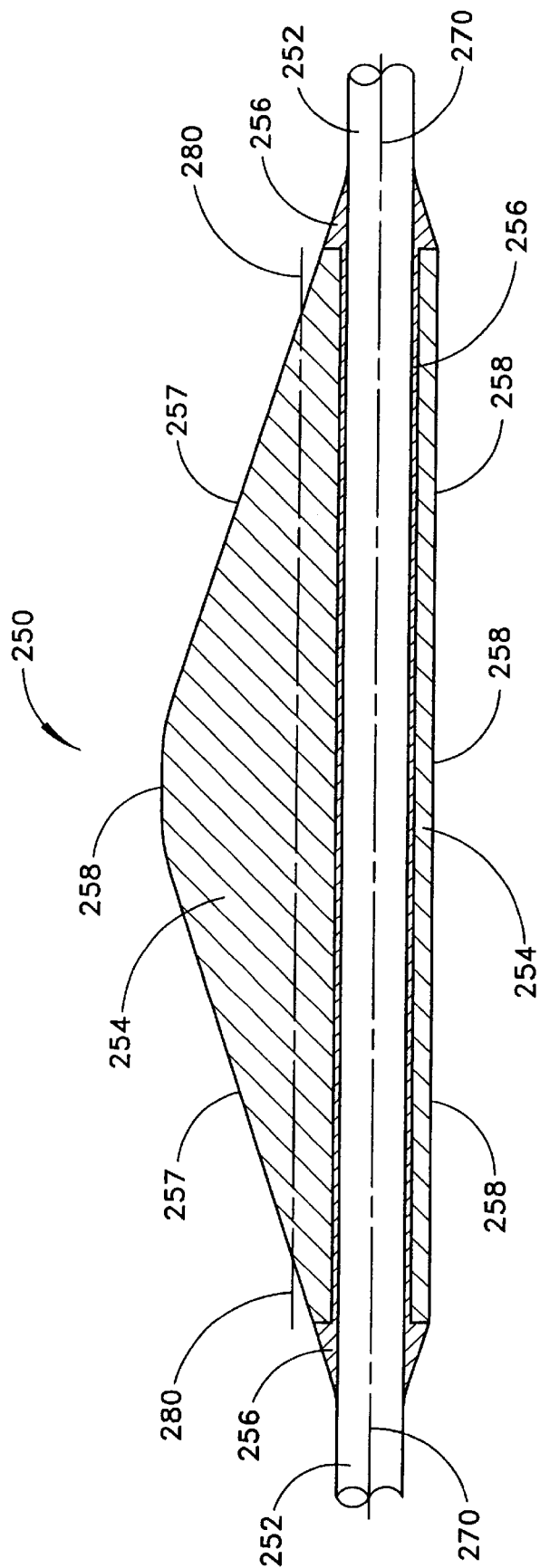
FIG. 33 is a longitudinal cross-sectional view of FIG. 32K, taken along lines 33—33 thereof.

FIGS. 31–33 depict another variation of the eccentric enlarged diameter section 228 of the invention and an eccentric enlarged diameter component 254 of a mandrel 250 for making the drive shaft of the invention. (Reference numbers in FIGS. 31–33 are in the 200 series, but otherwise generally correspond to those utilized in FIGS. 1–24 and in FIGS. 25–30.)

Both the longitudinal and transverse cross-sectional profiles of the eccentric enlarged diameter section 228 are slightly different from the corresponding profiles of the eccentric enlarged diameter sections 28 and 128 described above. Relatively small differences between the three-dimensional shape of the eccentric enlarged diameter section 228 and the three dimensional shapes of the eccentric enlarged diameter sections 28 and 128 may be best understood by reference to FIGS. 31–31C, which show the eccentric enlarged diameter section 228, and by reference to FIGS. 32–33, which show the mandrel 250 for making the drive shaft. As can be seen in FIGS. 31–33, the proximal 230 and distal 240 portions of the eccentric enlarged diameter section 228 each have an outer surface comprised of at least two areas, a first of the two areas being substantially defined by a lateral surface of a cone and a second of the two areas being substantially defined by a lateral surface of a cylinder. FIGS. 32–33 show that the cones 257 of both the proximal and distal portions of the eccentric enlarged diameter component 254 of the mandrel 250 have a common axis 221 which coincides with the rotational axis of the drive shaft. The intermediate portion 235 of the eccentric enlarged diameter section 228 has an outer surface which is substantially defined by a lateral surface of a cylinder having an axis which is parallel to and spaced away from the rotational axis of the drive shaft. The same cylinder which defines the outer surface of the intermediate portion 235 of the eccentric enlarged diameter section 228 also defines cylindrical areas of the outer surfaces of both the proximal 230 and distal 240 portions of the eccentric enlarged diameter section 228. The junction of the cylindrical surface with the proximal and distal conical surfaces is shown as lines 259 in FIG. 32.

Again, the geometric shape of the cones 257 and the cylinder 258, as well as the fact that the axis 280 of the cylinder 258 is parallel to and spaced away from the common axes 270 of the cones 257, may be best understood with reference to FIGS. 32–33, showing the mandrel 250 and its various cross-sections.

As with the proximal and distal portions of the eccentric enlarged diameter component 254 of the mandrel, the corresponding proximal and distal portions of the eccentric enlarged diameter section 228 of the drive shaft are not only equal in length but are also essentially mirror images of each other.

Figure 34:
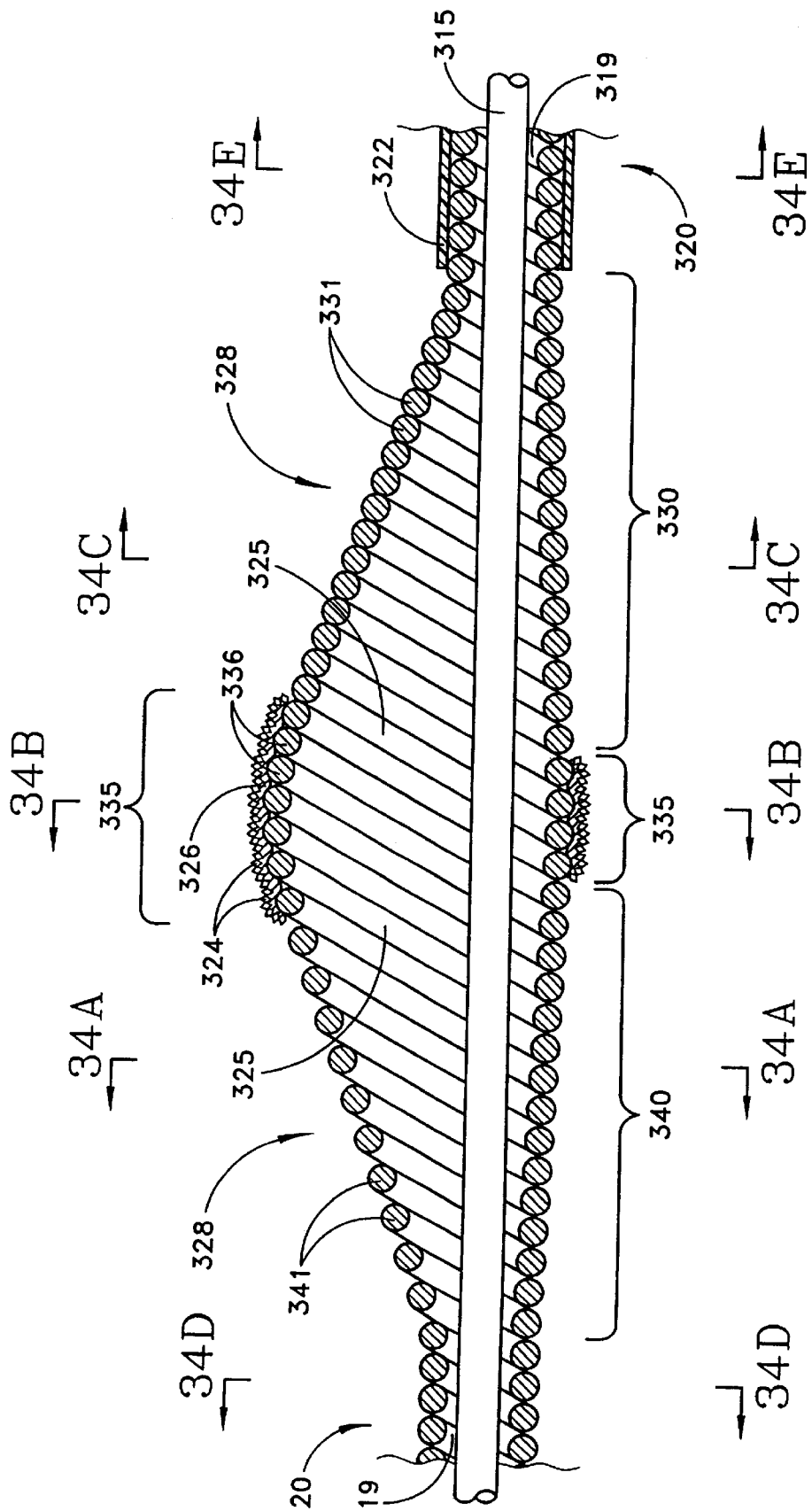
FIG. 34 is a longitudinal cross-sectional view of another alternate embodiment of the invention employing a slightly differently shaped eccentric enlarged diameter section.

FIGS. 34–34E depict yet another variation on the eccentric enlarged diameter section of the invention. (Reference numbers in FIGS. 34–34E are in the 300 series, but again otherwise generally correspond to those utilized in FIGS. 1–33.) As can be seen (particularly in the transverse cross-sections shown in FIGS. 34A–34C) the major lobe 338 of the eccentric enlarged diameter section 328 extends laterally significantly further away from the rotational axis of the drive shaft than the major lobes of the eccentric enlarged diameter sections 28, 128 and 228 described above, thereby providing a substantially oblong shape to the transverse cross-sections shown in FIGS. 34A–34C. The center of mass 329 of each cross-sectional slice (and the center of mass of the entire enlarged diameter section 328) is spaced further away from the rotational axis of the drive shaft than in the eccentric enlarged diameter sections 28, 128 and 228. Obviously, the further away the center of mass is spaced from the rotational axis the more eccentric is the rotational atherectomy device of the invention. For an eccentric enlarged diameter section 328 having an oblong shape, the eccentricity can be quantified by reference to a maximum length chord (i.e., the longest chordoincident with plane $P_1$ in FIG. 34B) drawn through the rotational axis of the drive shaft, the chord connecting two points on a perimeter of a transverse cross-section taken at a position where the perimeter of the enlarged diameter section 328 has its maximum length. The mid-point of this maximum length chord is spaced away from the rotational axis of the drive shaft, and, in FIG. 34B substantially coincides with the center of mass 329 of the cross-sectional slice. For an eccentric enlarged diameter section 328 having a maximum length chord between about 1.5 mm and about 1.75 mm, the chord mid-point desirably is spaced away from the rotational axis of the drive shaft by a distance of at least about 0.07 mm, preferably by a distance of at least about 0.1 mm, and most preferably by a distance of at least about 0.13 mm; for an eccentric enlarged diameter section 328 having a maximum length chord between about 1.75 mm and about 2.0 mm, the chord mid-point desirably is spaced away from the rotational axis of the drive shaft by a distance of at least about 0.15 mm, preferably by a distance of at least about 0.2 mm, and most preferably by a distance of at least about 0.25 mm; and for an eccentric enlarged diameter section 328 having a maximum length chord of at least about 2.0 mm, the chord mid-point desirably is spaced away from the rotational axis of the drive shaft by a distance of at least about 0.3 mm, preferably by a distance of at least about 0.35 mm, and most preferably by a distance of at least about 0.4 mm.

Figure 35:
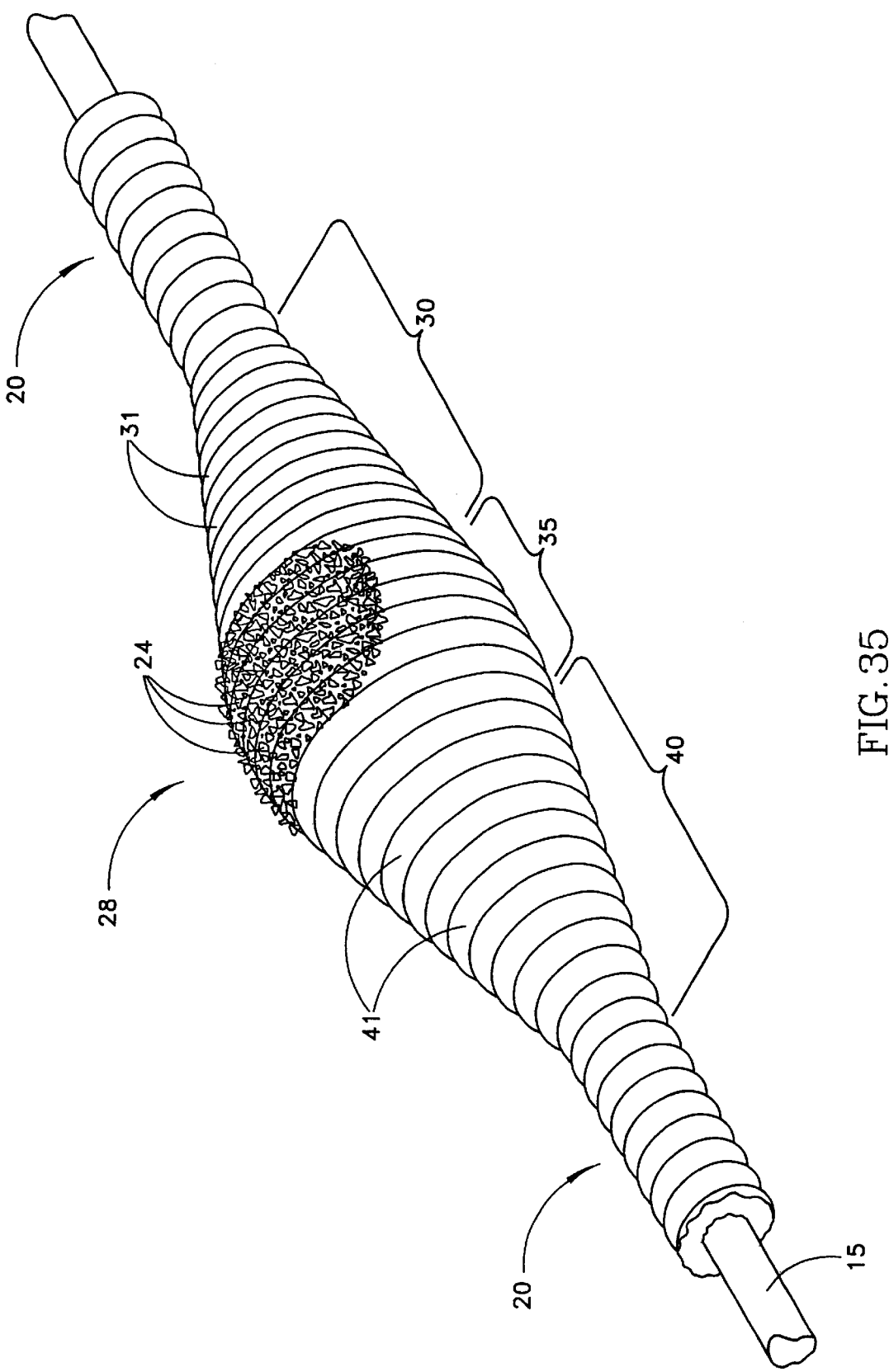
FIG. 35 is a perspective view of an enlarged diameter section of an alternate embodiment of the invention.

In the embodiments shown in FIGS. 1–34 the abrasive surface of the eccentric enlarged diameter section is disposed around both the major and minor lobes, and, in all these embodiments, the abrasive surface of the major lobe preferably is longitudinally longer than the abrasive surface of the minor lobe. In the embodiment shown in FIG. 35, the abrasive surface of the eccentric enlarged diameter section 28 of the drive shaft 20 is disposed substantially only on the major lobe, defining a tissue removal segment that does not extend all the way around the eccentric enlarged diameter section 28. Such asymmetrical location of the abrasive surface around the enlarged diameter section 28 is possible because usually only a portion of the abrasive surface of the major lobe performs almost all of the tissue removal.

Although most of the drawings illustrate the abrasive surface defining the tissue removing segment of the drive shaft to be contained within the intermediate portion of the eccentric enlarged diameter section of the drive shaft, the abrasive surface may also extend, if desired, into the proximal or distal portions of the enlarged diameter section.

Figure 36:
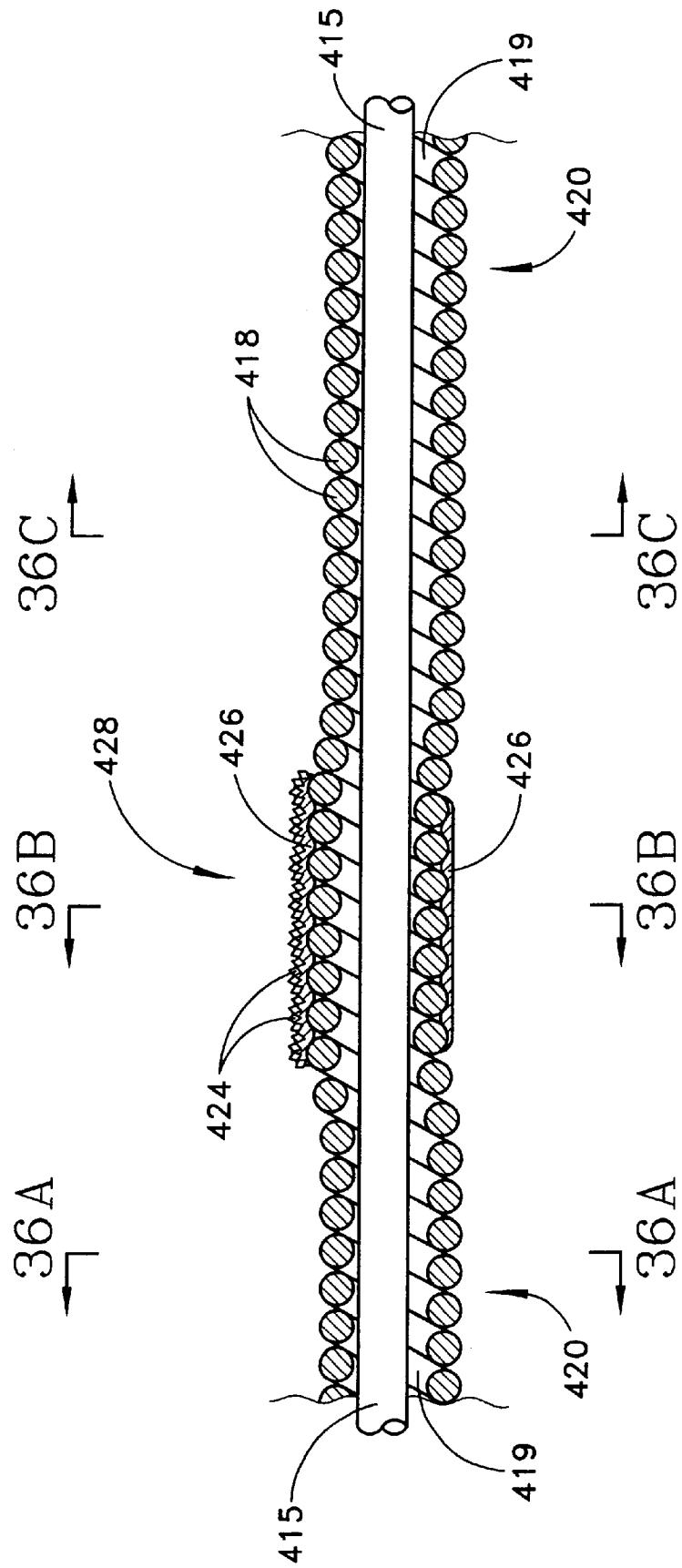
FIG. 36 is a longitudinal cross-sectional view of a very low profile embodiment of the invention employing a tissue removing section that is eccentric but the wire turns of which have generally the same diameter as the wire turns of the rest of the drive shaft.
Figure 37:
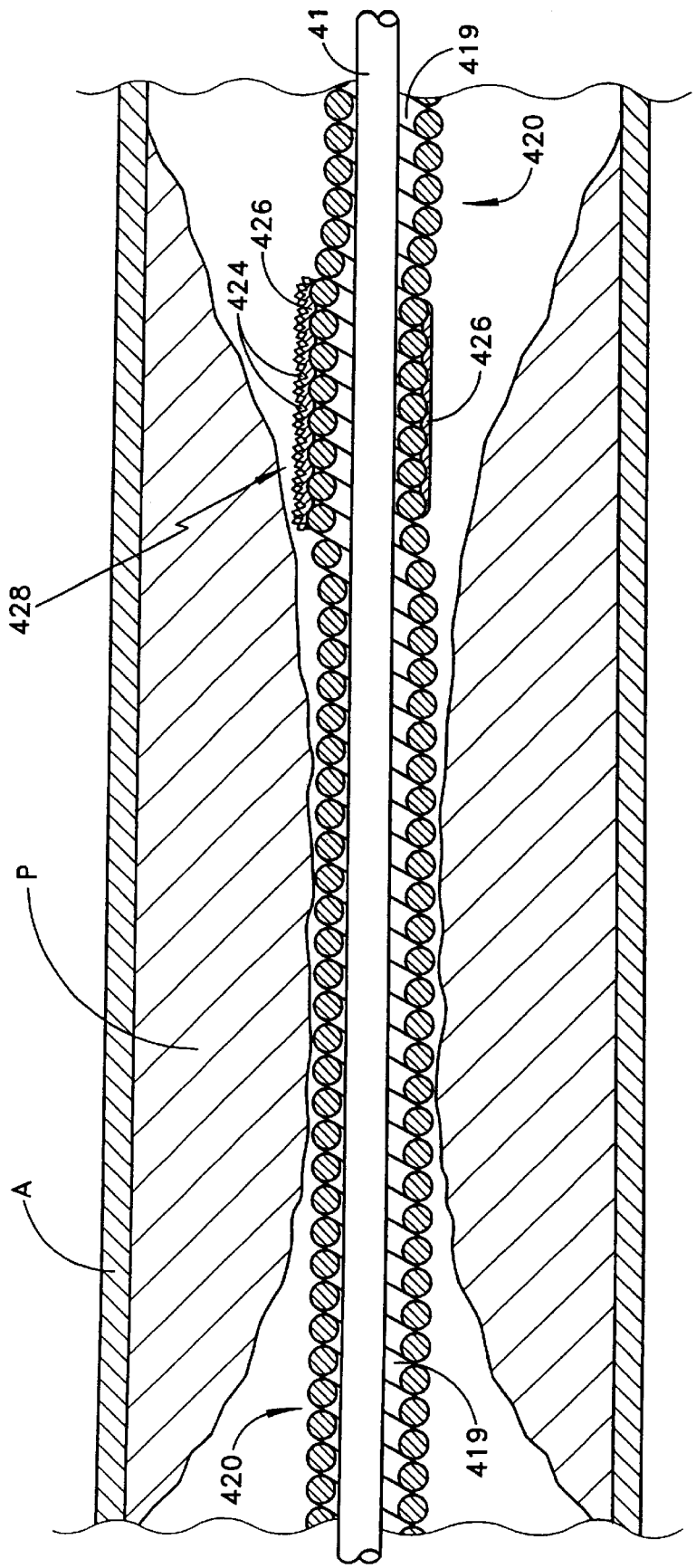
FIG. 37 shows a longitudinal cross-sectional view of the eccentric atherectomy device of FIG. 36 with its tissue removing segment just prior to being advanced distally across a stenosis.
Figure 38:
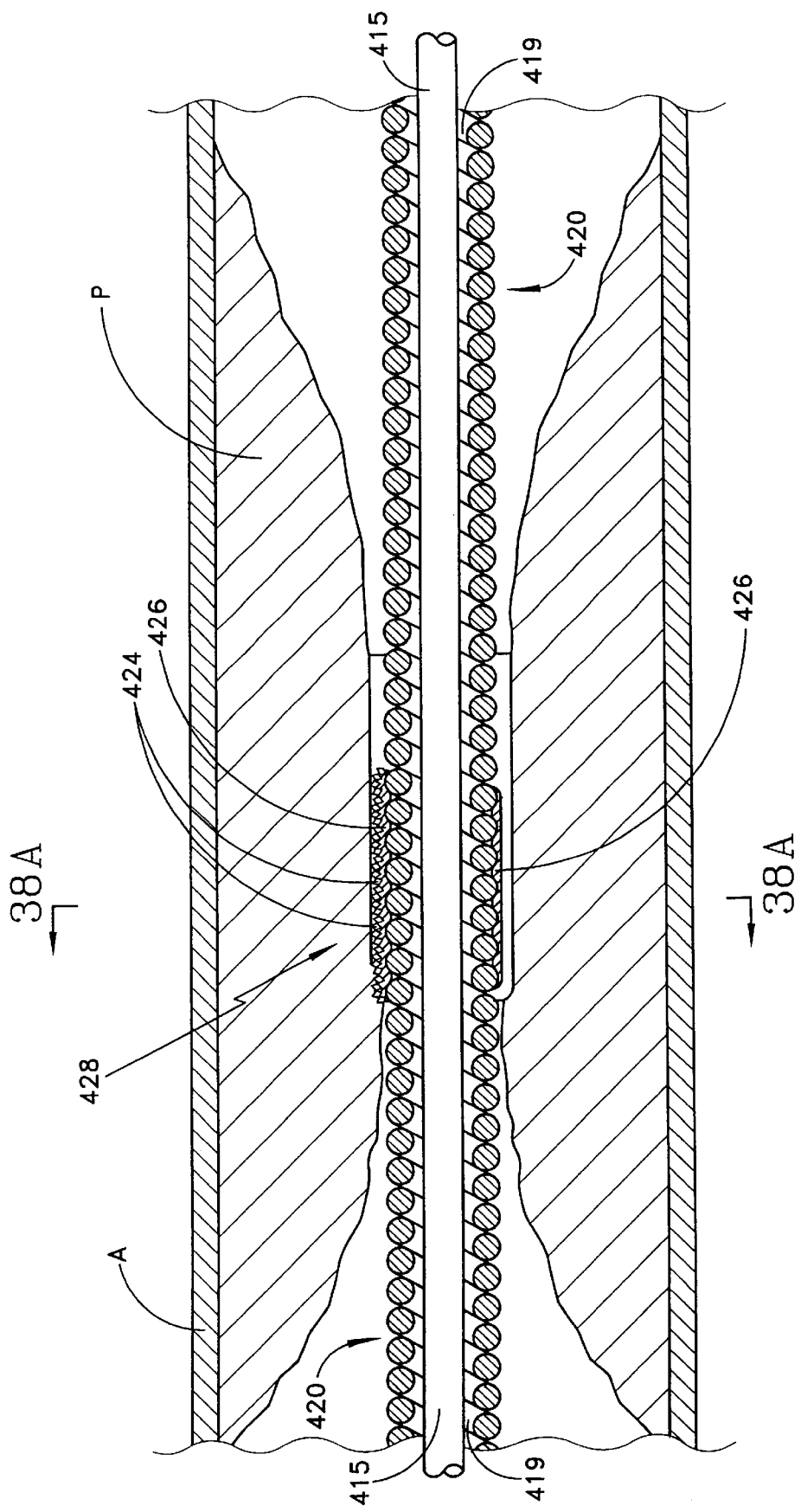
FIG. 38 is a longitudinal cross-sectional view similar to FIG. 37, showing the tissue removing segment being moved distally to remove stenotic tissue from an artery.
Figure 38A:
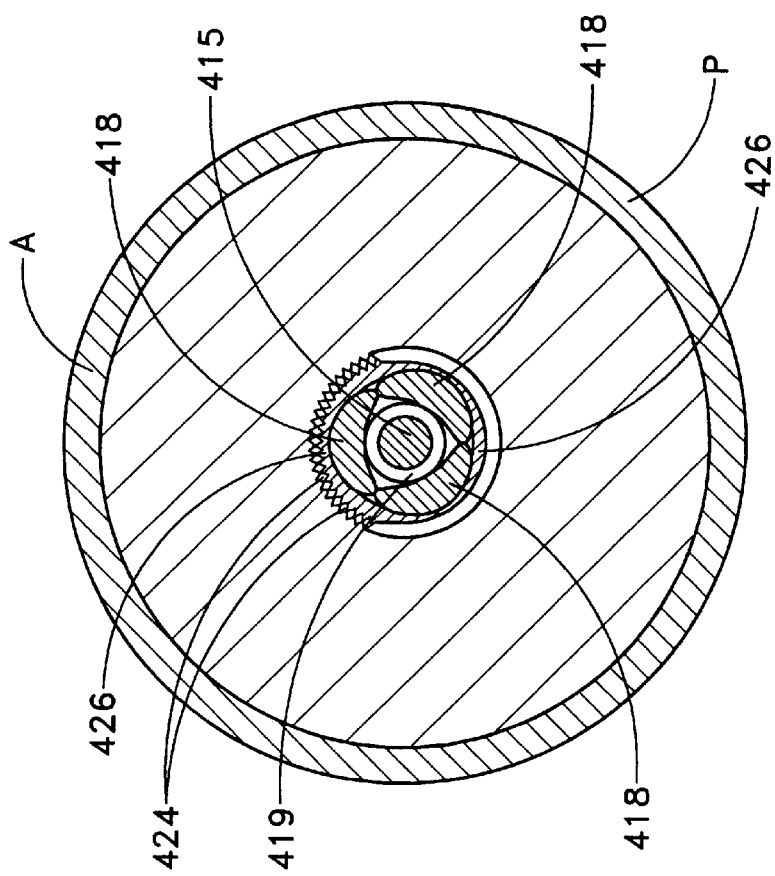
FIG. 38A is a transverse cross-sectional view of FIG. 38, taken along lines 38A—38A thereof.
Figure 39:
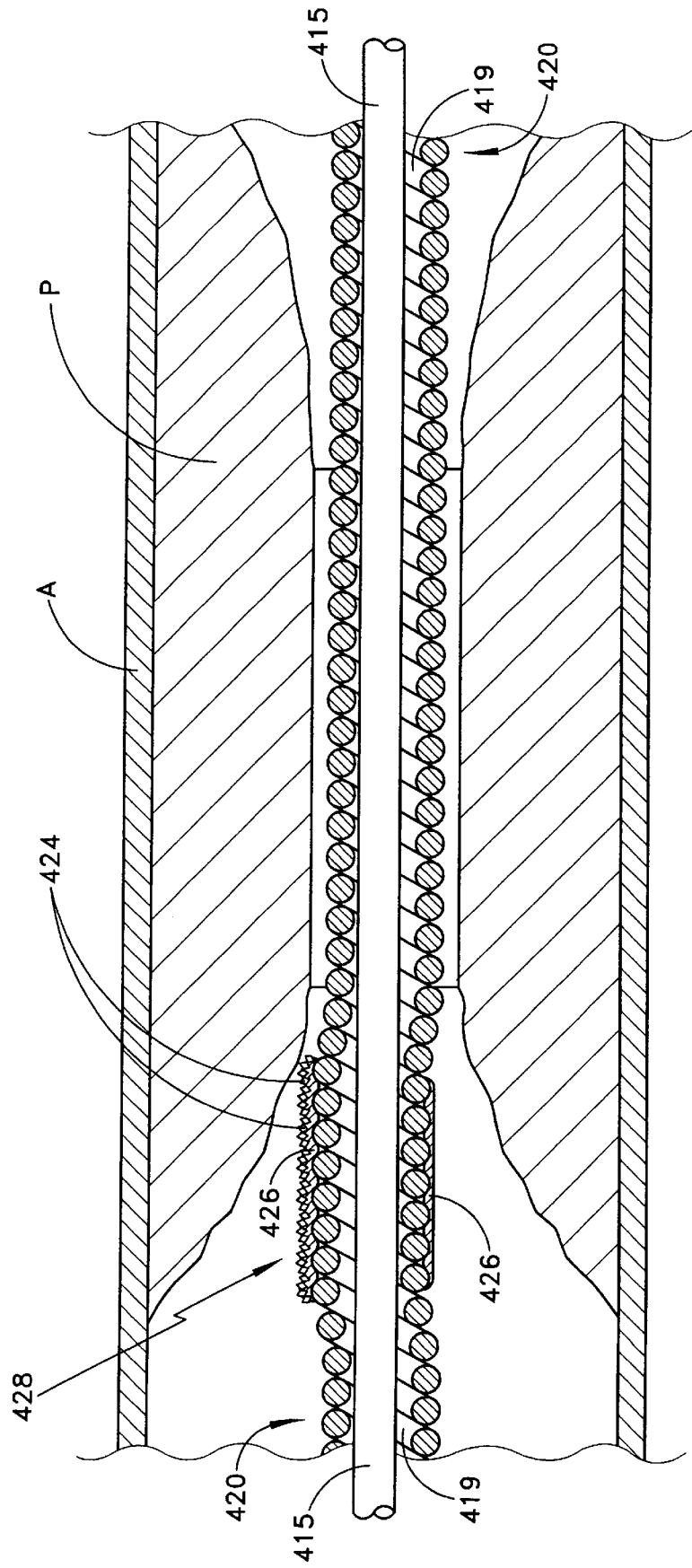
FIG. 39 is a longitudinal cross-sectional view similar to FIGS. 37–38, showing the tissue removing segment after it has moved distally through a stenosis.
Figure 40:
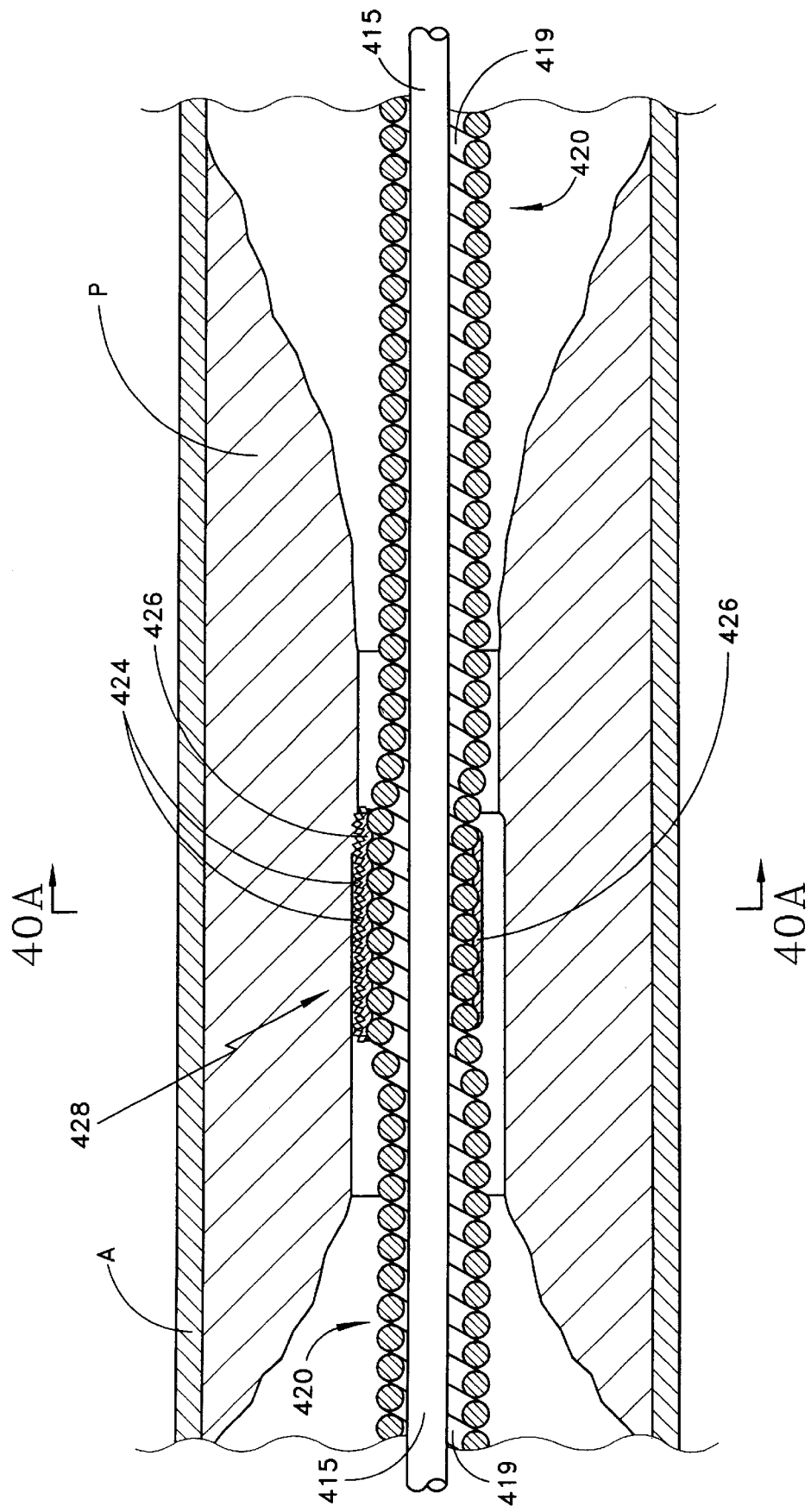
FIG. 40 is a longitudinal cross-sectional view similar to FIGS. 37–39, showing a subsequent stage of removal of stenotic tissue from an artery, the tissue removing segment being moved proximally through a stenosis.
Figure 40A:
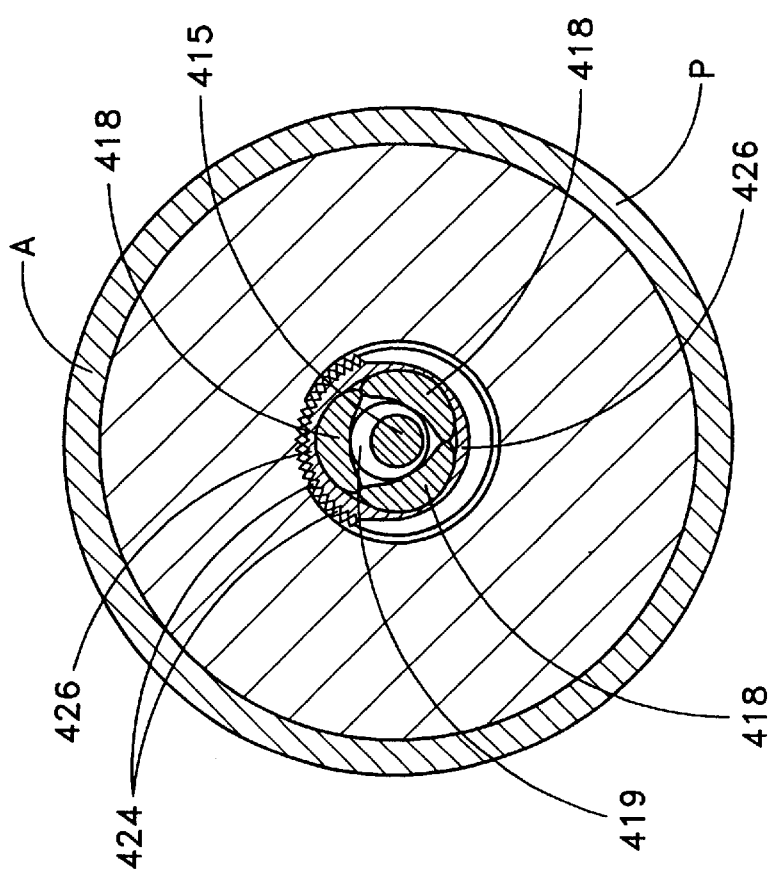
FIG. 40A is transverse cross-sectional view of FIG. 40, taken along lines 40A—40A thereof.

The invention has been described with reference to a rotational atherectomy device comprised of a helically wound drive shaft with an eccentric enlarged diameter section. The concept of an eccentric tissue removal device, however, could also be applied to other types or shapes of rotational atherectomy devices. For example, as shown in FIGS. 36–41, the invention could be utilized in connection with a rotational atherectomy device comprising a helically wound drive shaft 420 of a generally constant diameter (i.e., without an enlarged diameter section) having an abrasive surface formed by electroplating abrasive particles 424 to the drive shaft 420. (Reference numbers in FIGS. 36–41 are in the 400 series, but again otherwise generally correspond to those utilized in FIGS. 1–35.) As is shown in FIG. 36, the tissue removing section 428 of the drive shaft 420 can be made eccentric by simply forming a short length of the drive shaft with a geometric axis which is parallel to but slightly offset with respect to the geometric axis (and, thus, the rotational axis) of the rest of the drive shaft 420. Providing such a shape to the drive shaft may be accomplished by winding a straight drive shaft, placing it into an appropriately shaped mold or form, and heating for an appropriate period of time at a temperature adequate to give the drive shaft the new shape. Usually, offsetting the geometric axis of the tissue removing section will also cause the center of mass of the tissue removing section 428 to become offset with respect to the rotational axis of the drive shaft 420. Electroplating abrasive particles 424 only on one side of the tissue removing section 428 (or removing abrasive material from one side of the tissue removing section 428), as shown in FIG. 36, will further increase the eccentricity of the atherectomy device of the invention. Thus, in such a device a face of a transverse cross-section (such as FIG. 36B) of the tissue removing section 428 has a geometric center which is spaced radially away from the rotational axis of the drive shaft 420. A device of this type has an extremely low profile, and yet can open a stenosis to a diameter larger than the nominal diameter of the device. FIGS. 37–40A illustrate the multiple forward and backward movements of the rotating eccentric tissue removal section 428 across a stenosis, thereby demonstrating that the use of the device shown in FIGS. 36–36C is substantially the same as the device having an eccentric enlarged diameter section 28 (shown in use in FIGS. 6–14A).

Figure 41:
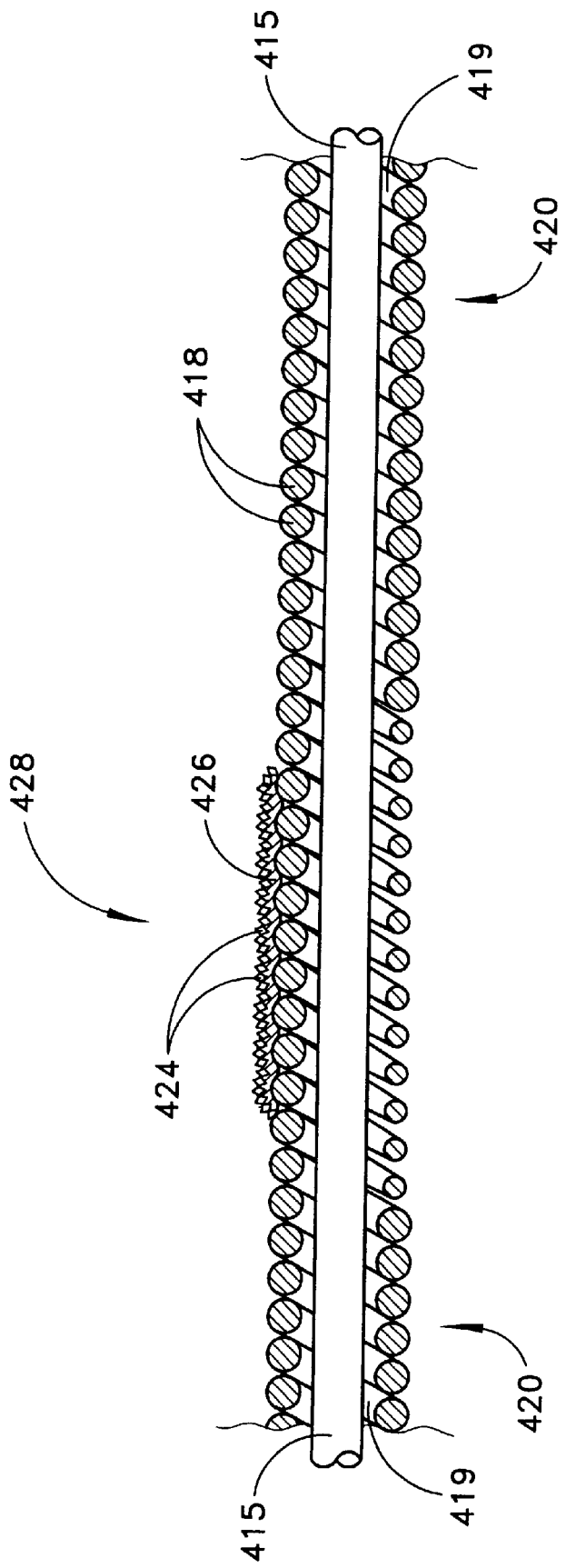
FIG. 41 is a longitudinal cross-sectional view of another very low profile embodiment of the invention.

Alternately, the tissue removal section 428 of the drive shaft 420 having an abrasive surface can be made eccentric by adding mass to one side (such as by coating abrasive material 424 only on one side of the tissue removing section 428) and/or by removing mass only from one side (such as by thinning the helically wound wire 418 on one side), both of such techniques being illustrated in FIG. 41. Thinning of the helically wound wire on one side of the tissue removing section 428 can be accomplished, e.g., by electro-polishing or grinding.

Figure 42:
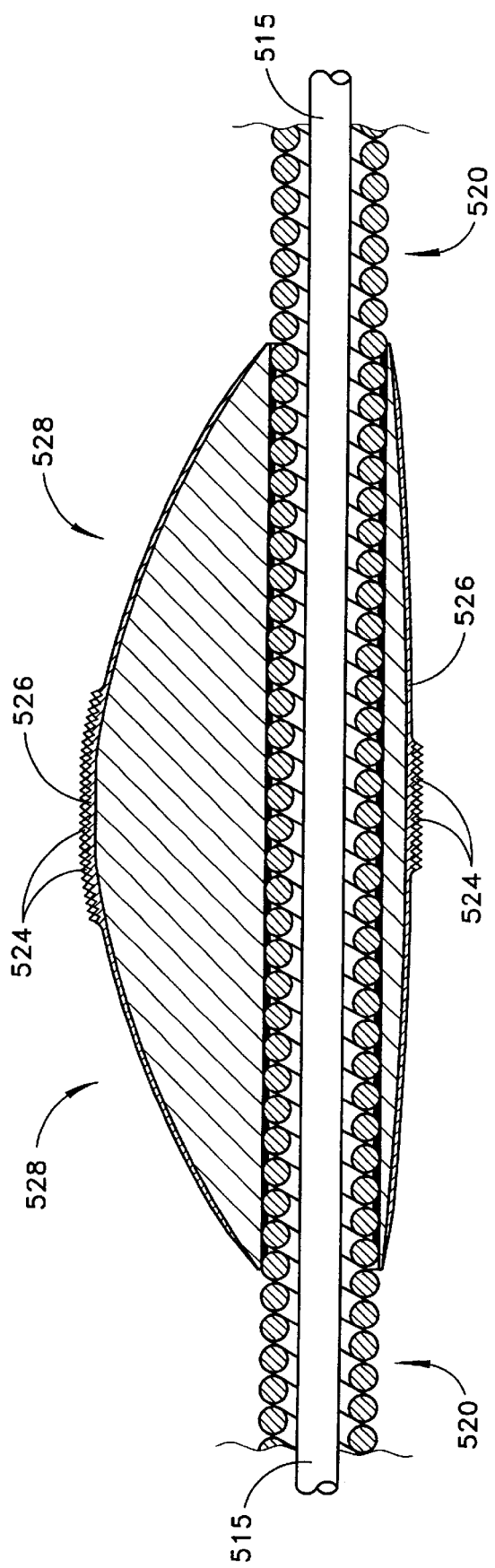
FIG. 42 is a longitudinal cross-sectional view of another embodiment of the invention employing an eccentric abrasive burr attached to a drive shaft.

In yet another application of the invention, FIG. 42 illustrates a rotational atherectomy device which employs an eccentric tissue removing burr 528 attached to a flexible drive shaft 520, rotated over a guide wire 515. The eccentric tissue removing burr 528. has a coating of abrasive particles 524 secured to a portion of its outer surface by a suitable binding material 526. As with the other embodiments described above, the eccentricity of the burr 528 can be achieved by placing the center of mass offset from the axis of rotation, by placing the geometric center offset from the axis of rotation, or a combination of these techniques. Preferably the center of mass of the eccentric tissue removing burr 528 is spaced radially away from the rotational axis of the drive shaft by a distance of at least about 0.02 mm, and preferably the geometric center of the eccentric tissue removing burr 528 is spaced radially away from the rotational axis by a distance of at least about 0.035 mm.

While a preferred embodiment of the present invention has been described, it should be understood that various changes, adaptations and modifications may be made therein without departing from the spirit of the invention and the scope of the appended claims.

What is claimed is:

1. A rotational atherectomy device for opening a stenosis in an artery having a given diameter, comprising a guide wire having a maximum diameter less than the diameter of the artery, and a flexible, elongated, rotatable drive shaft advanceable over the guide wire, the drive shaft having a rotational axis and an eccentric enlarged diameter section, at least part of the eccentric enlarged diameter section having a tissue removing surface to define a tissue removing segment of the drive shaft, the drive shaft, including its eccentric enlarged diameter section, being comprised of one or more helically wound wires.

2. The rotational atherectomy device of claim 1 wherein the helically wound wires define a guide wire lumen and a hollow cavity within the eccentric enlarged diameter section.

3. The rotational atherectomy device of claim 2 further comprising a guide wire, the guide wire being disposed within the guide wire lumen of the drive shaft and traversing the hollow cavity of the enlarged diameter section, the hollow cavity, except for the presence of the guide wire, being substantially empty.

4. The rotational atherectomy device of claim 2 wherein the eccentric enlarged diameter section includes proximal, intermediate and distal portions, wire turns of the proximal portion having diameters that increase distally and wire turns of the distal portion having diameters that decrease distally.

5. The rotational atherectomy device of claim 4 wherein the proximal portion of the eccentric enlarged diameter section has an outer surface which is substantially defined by a lateral surface of a cone, the cone having an axis which intersects the rotational axis of the drive shaft.

6. The rotational atherectomy device of claim 5 wherein the distal portion of the eccentric enlarged diameter section has an outer surface which is substantially defined by a lateral surface of a cone, the cone having an axis which intersects the rotational axis of the drive shaft.

7. The rotational atherectomy device of claim 6 wherein the intermediate portion of the eccentric enlarged diameter section has a convex outer surface which is shaped to provide a smooth transition between surfaces of the proximal and distal portions of the enlarged diameter section.

8. The rotational atherectomy device of claim 7 wherein the tissue removing surface defining the tissue removing segment of the drive-shaft includes at least a surface of the intermediate portion of the eccentric enlarged diameter section of the drive shaft.

9. The rotational atherectomy device of claim 7 wherein the tissue removing surface defining the tissue removing segment of the drive shaft is substantially limited to a surface of the intermediate portion of the eccentric enlarged diameter section of the drive shaft.

10. The rotational atherectomy device of claim 6 wherein the cone axis of the proximal portion and the cone axis of the distal portion intersect each other and are coplanar with the rotational axis of the drive shaft.

11. The rotational atherectomy device of claim 4 wherein wire turns of the proximal portion of the eccentric enlarged diameter section have diameters that increase distally at a generally constant rate, thereby forming generally the shape of a cone.

12. The rotational atherectomy device of claim 11 wherein wire turns of the distal portion of the eccentric enlarged diameter section have diameters that decrease distally at a generally constant rate, thereby forming generally the shape of a cone.

13. The rotational atherectomy device of claim 12 wherein opposing sides of each cone are at angle α of between about 10° and about 30° with respect to each other.

14. The rotational atherectomy device of claim 12 wherein opposing sides of each cone are at angle α of between about 20° and about 24° with respect to each other.

15. The rotational atherectomy device of claim 12 wherein each of the cones of the eccentric enlarged diameter section has an axis that is not parallel to the rotational axis of the drive shaft.

16. The rotational atherectomy device of claim 12 wherein the axes of the cones of the eccentric enlarged diameter section are coplanar and intersect the rotational axis of the drive shaft at an angle β of between about 2° and about 8°.

17. The rotational atherectomy device of claim 12 wherein the axes of the cones of the eccentric enlarged diameter section are coplanar and intersect the rotational axis of the drive shaft at an angle β of between about 3° and about 6°.

18. The rotational atherectomy device of claim 4 wherein adjacent wire turns of the intermediate portion of the eccentric enlarged diameter section of the drive shaft are secured to one another.

19. The rotational atherectomy device of claim 4 wherein adjacent wire turns of the proximal and distal portions of the eccentric enlarged diameter section of the drive shaft are not secured to one another, thereby permitting such portions of the drive shaft to flex.

20. The rotational atherectomy device of claim 1 wherein at least some adjacent wire turns of the eccentric enlarged diameter section of the drive shaft are not secured to one another, thereby permitting centrifugal forces to deform the eccentric enlarged diameter section of the drive shaft when the drive shaft is rotated.

21. The rotational atherectomy device of claim 4 wherein the proximal portion of the eccentric enlarged diameter section has an outer surface comprised of at least two areas, a first of the two areas being substantially defined by a lateral surface of a frustum of a first cone, and a second of the two areas being substantially defined by a lateral surface of a frustum of a second cone, the first cone having an axis which coincides with the rotational axis of the drive shaft and the second cone having an axis which is parallel to and spaced away from the axis of the first cone.

22. The rotational atherectomy device of claim 4 wherein the distal portion of the eccentric enlarged diameter section has an outer surface comprised of at least two areas, a first of the two areas being substantially defined by a lateral surface of a frustum of a first cone, and a second of the two areas being substantially defined by a lateral surface of a frustum of a second cone, the first cone having an axis which coincides with the rotational axis of the drive shaft, and the second cone having an axis which is parallel to and spaced away from the axis of the first cone.

23. The rotational atherectomy device of claim 21 or 22 wherein an angle formed between the lateral surface of the first cone and the axis of the first cone is larger than an angle formed between the lateral surface of the second cone and the axis of the second cone.

24. The rotational atherectomy device of claim 4 wherein the distal portion and the proximal portion of the eccentric enlarged diameter section each has an outer surface comprised of at least two areas, a first of the two areas being substantially defined by a lateral surface of a frustum of a first cone, and a second of the two areas being substantially defined by a lateral surface of a frustum of a second cone, the first cone having an axis which coincides with the rotational axis of the drive shaft, and the second cone having an axis which is parallel to and spaced away from the axis of the first cone.

25. The rotational atherectomy device of claim 24 wherein the second cones of the proximal and distal portions of the eccentric enlarged diameter section have a common axis which is parallel to and spaced away from the rotational axis of the drive shaft.

26. The rotational atherectomy device of claim 24 wherein the intermediate portion of the eccentric enlarged diameter section has an outer surface which is substantially defined by a lateral surface of a cylinder.

27. The rotational atherectomy device of claim 26 wherein each of the two second cones of the proximal and distal portions of the enlarged diameter section has a base having a diameter which is equal to a diameter of the cylinder defining the outer surface of the intermediate portion of the enlarged diameter section.

28. The rotational atherectomy device of claim 24 wherein the intermediate portion of the eccentric enlarged diameter section has an outer surface which is substantially defined by a lateral surface of a cylinder having an axis which is common to the axes of the second cones of the proximal and distal portions of the eccentric enlarged diameter section.

29. The rotational atherectomy device of claim 24 wherein the intermediate portion of the eccentric enlarged diameter section has a surface which is shaped to provide a smooth transition between surfaces of the proximal and distal portions of the eccentric enlarged diameter section.

30. The rotational atherectomy device of claim 24 wherein the proximal and distal portions of the eccentric enlarged diameter section of the drive shaft are substantially equal in length.

31. The rotational atherectomy device of claim 24 wherein the proximal and distal portions of the eccentric enlarged diameter section are generally symmetrical to each other with respect to a plane which passes through the intermediate portion of the eccentric enlarged diameter section and is generally perpendicular to the rotational axis of the drive shaft.

32. The rotational atherectomy device of claim 4 wherein the proximal portion of the eccentric enlarged diameter section has an outer surface comprised of at least two areas, a first of the two areas being substantially defined by a lateral surface of a proximal cone and a second of the two areas being substantially defined by a lateral surface of a cylinder, the proximal cone having an axis which coincides with the rotational axis of the drive shaft and the cylinder having an axis which is parallel to and spaced away from the rotational axis of the drive shaft.

33. The rotational atherectomy device of claim 4 wherein the distal portion of the eccentric enlarged diameter section has an outer surface comprised of at least two areas, a first of the two areas being substantially defined by a lateral surface of a distal cone and a second of the two areas being substantially defined by a lateral surface of a cylinder, the distal cone having an axis which coincides with the rotational axis of the drive shaft and the cylinder having an axis which is parallel to and spaced away from the rotational axis of the drive shaft.

34. The rotational atherectomy device of claim 4 wherein the distal portion and the proximal portion of the eccentric enlarged diameter section each has an outer surface comprised of at least two areas, a first of the two areas being substantially defined by a lateral surface of a cone and a second of the two areas being substantially defined by a lateral surface of a cylinder, the cones having a common axis which coincides with the rotational axis of the drive shaft and the cylinder having an axis which is parallel to and spaced away from the rotational axis of the drive shaft.

35. The rotational atherectomy device of claim 34 wherein the intermediate portion of the eccentric enlarged diameter section has an outer surface substantially defined by a lateral surface of the cylinder which defines the second areas of the proximal and distal portions of the eccentric enlarged diameter section.

36. The rotational atherectomy device of claim 34 wherein the proximal and distal portions of the eccentric enlarged diameter section are generally symmetrical with respect to a plane which passes through the intermediate portion of the eccentric enlarged diameter section and is generally perpendicular to the rotational axis of the drive shaft.

37. The rotational atherectomy device of claim 1 or 2 wherein the eccentric enlarged diameter section has an outer surface shaped so that the eccentric enlarged diameter section is divided into two generally symmetrical lobes by a plane that is drawn through the rotational axis of the drive shaft and a point on the outer surface of the eccentric enlarged diameter section which is most distant from the rotational axis of the drive shaft.

38. The rotational atherectomy device of claim 1 or 2 wherein the eccentric enlarged diameter section has an outer surface shaped so that the eccentric enlarged diameter section is divided into major and minor lobes by a plane that is drawn through the rotational axis of the drive shaft and is perpendicular to another plane that is drawn through the rotational axis and a point on the outer surface of the eccentric enlarged diameter section which is most distant from the rotational axis of the drive shaft.

39. The rotational atherectomy device of claim 38 wherein the eccentric enlarged diameter section has a center of mass located within the major lobe.

40. The rotational atherectomy device of claim 38 wherein the lobes each have a mass, the mass of the major lobe being larger than the mass of the minor lobe.

41. The rotational atherectomy device of claim 38 wherein the lobes each have an outer surface, the outer surface of the major lobe being larger than the outer surface of the minor lobe.

42. The rotational atherectomy device of claim 38 wherein the lobes each have a mass and an outer surface, the mass and the outer surface of the major lobe being larger than the mass and the outer surface of the minor lobe.

43. The rotational atherectomy device of claim 38 wherein the tissue removing surface of the eccentric enlarged diameter section of the drive shaft is disposed substantially only on the major lobe.

44. The rotational atherectomy device of claim 38 wherein the tissue removing surface of the eccentric enlarged diameter section is disposed around both the major and minor lobes, the tissue removing surface of the major lobe being longitudinally longer than the tissue removing surface of the minor lobe.

45. The rotational atherectomy device of claim 38 wherein the lobes each have an outer surface, a maximum distance from the rotational axis of the drive shaft to the outer surface of the major lobe is larger than a maximum distance from the rotational axis to the outer surface of the minor lobe.

46. The rotational atherectomy device of claim 1 or 2 wherein the eccentric enlarged diameter section has a center of mass which is spaced radially away from the rotational axis of the drive shaft.

47. The rotational atherectomy device of claim 46 wherein the eccentric enlarged diameter section has a shape such that a plane that is drawn through the rotational axis and the center of mass of the eccentric enlarged diameter section divides the eccentric enlarged diameter section into two generally symmetrical lobes.

48. The rotational atherectomy device of claim 46 wherein the eccentric enlarged diameter section has a shape such that a plane drawn through the rotational axis and perpendicular to another plane drawn through the same axis and the center of mass of the eccentric enlarged diameter section divides the eccentric enlarged diameter section into major and minor lobes.

49. The rotational atherectomy device of claim 48 wherein the center of mass of the eccentric enlarged diameter section is located within the major lobe.

50. The rotational atherectomy device of claim 48 wherein the lobes each have a mass, the mass of the major lobe being larger than the mass of the minor lobe.

51. The rotational atherectomy device of claim 48 wherein the lobes each have an outer surface, the outer surface of the major lobe being larger than the outer surface of the minor lobe.

52. The rotational atherectomy device of claim 48 wherein the lobes each have a mass and an outer surface, the mass and the outer surface of the major lobe being larger than the mass and the outer surface of the minor lobe.

53. The rotational atherectomy device of claim 48 wherein the tissue removing surface of the eccentric enlarged diameter section of the drive shaft is disposed substantially only on the major lobe.

54. The rotational atherectomy device of claim 48 wherein the tissue removing surface of the eccentric enlarged diameter section is disposed around both the major and minor lobes, the tissue removing surface of the major lobe being longitudinally longer than the tissue removing surface of the minor lobe.

55. The rotational atherectomy device of claim 48 wherein the lobes each have an outer surface, a maximum distance from the rotational axis of the drive shaft to the outer surface of the major lobe is larger than a maximum distance from the rotational axis to the outer surface of the minor lobe.

56. The rotational atherectomy device of claim 46 wherein the eccentric enlarged diameter section has a maximum diameter between about 1.0 mm and about 1.5 mm, and the center of mass is spaced away from the rotational axis of the drive shaft by a distance of at least about 0.013 mm.

57. The rotational atherectomy device of claim 46 wherein the eccentric enlarged diameter section has a maximum diameter between about 1.5 mm and about 1.75 mm, and the center of mass is spaced away from the rotational axis of the drive shaft by a distance of at least about 0.03 mm.

58. The rotational atherectomy device of claim 46 wherein the eccentric enlarged diameter section has a maximum diameter between about 1.75 mm and about 2.0 mm, and the center of mass is spaced away from the rotational axis of the drive shaft by a distance of at least about 0.06 mm.

59. The rotational atherectomy device of claim 46 wherein the eccentric enlarged diameter section has a maximum diameter of at least about 2.0 mm, and the center of mass is spaced away from the rotational axis of the drive shaft by a distance of at least about 0.1 mm.

60. The rotational atherectomy device of claim 46 wherein the eccentric enlarged diameter section has a maximum diameter between about 1.0mm and about 1.5 mm, and the center of mass is spaced away from the rotational axis of the drive shaft by a distance of at least about 0.02 mm.

61. The rotational atherectomy device of claim 46 wherein the eccentric enlarged diameter section has a maximum diameter between about 1.5 mm and about 1.75 mm, and the center of mass is spaced away from the rotational axis of the drive shaft by a distance of at least about 0.05 mm.

62. The rotational atherectomy device of claim 46 wherein the eccentric enlarged diameter section has a maximum diameter between about 1.75 mm and about 2.0 mm, and the center of mass is spaced away from the rotational axis of the drive shaft by a distance of at least about 0.1 mm.

63. The rotational atherectomy device of claim 46 wherein the eccentric enlarged diameter section has a maximum diameter of at least about 2.0 mm, and the center of mass is spaced away from the rotational axis of the drive shaft by a distance of at least about 0.16 mm.

64. The rotational atherectomy device of claim 1 or 2 wherein a face of a transverse cross-section of the eccentric enlarged diameter section, taken at a position of maximum cross-sectional diameter of the eccentric enlarged diameter section has a geometric center spaced away from the rotational axis of the drive shaft.

65. The rotational atherectomy device of claim 64 wherein the eccentric enlarged diameter section has a maximum cross-sectional diameter between about 1.0 mm and about 1.5 mm, and the geometric center is spaced away from the rotational axis of the drive shaft by a distance of at least about 0.02 mm.

66. The rotational atherectomy device of claim 64 wherein the eccentric enlarged diameter section has a maximum cross-sectional diameter between about 1.5 mm and about 1.75 mm, and the geometric center is spaced away from the rotational axis of the drive shaft by a distance of at least about 0.05 mm.

67. The rotational atherectomy device of claim 64 wherein the eccentric enlarged diameter section has a maximum cross-sectional diameter between about 1.75 mm and about 2.0 mm, and the geometric center is spaced away from the rotational axis of the drive shaft by a distance of at least about 0.1 mm.

68. The rotational atherectomy device of claim 64 wherein the eccentric enlarged diameter section has a maximum cross-sectional diameter of at least about 2.0 mm, and the geometric center is spaced away from the rotational axis of the drive shaft by a distance of at least about 0.15 mm.

69. The rotational atherectomy device of claim 64 wherein the eccentric enlarged diameter section has a maximum cross-sectional diameter between about 1.0 mm and about 1.5 mm, and the geometric center is spaced away from the rotational axis of the drive shaft by a distance of at least about 0.035 mm.

70. The rotational atherectomy device of claim 64 wherein the eccentric enlarged diameter section has a maximum cross-sectional diameter between about 1.5 mm and about 1.75 mm, and the geometric center is spaced away from the rotational axis of the drive shaft by a distance of at least about 0.07 mm.

71. The rotational atherectomy device of claim 64 wherein the eccentric enlarged diameter section has a maximum cross-sectional diameter between about 1.75 mm and about 2.0 mm, and the geometric center is spaced away from the rotational axis of the drive shaft by a distance of at least about 0.15 mm.

72. The rotational atherectomy device of claim 64 wherein the eccentric enlarged diameter section has a maximum cross-sectional diameter of at least about 2.0 mm, and the geometric center is spaced away from the rotational axis of the drive shaft by a distance of at least about 0.25 mm.

73. The rotational atherectomy device of claim 64 wherein the eccentric enlarged diameter section has a maximum cross-sectional diameter between about 1.5 mm and about 1.75 mm, and the geometric center is spaced away from the rotational axis of the drive shaft by a distance of at least about 0.09 mm.

74. The rotational atherectomy device of claim 64 wherein the eccentric enlarged diameter section has a maximum cross-sectional diameter between about 1.75 mm and about 2.0 mm, and the geometric center is spaced away from the rotational axis of the drive shaft by a distance of at least about 0.20 mm.

75. The rotational atherectomy device of claim 64 wherein the eccentric enlarged diameter section has a maximum cross-sectional diameter of at least about 2.0 mm, and the geometric center is spaced away from the rotational axis of the drive shaft by a distance of at least about 0.30 mm.

76. The rotational atherectomy device of claim 1 or 2 wherein the eccentric enlarged diameter section has a maximum length chord which is drawn through the rotational axis of the drive shaft and connects two points on a perimeter of a transverse cross-section taken at a position where the perimeter of the enlarged diameter section has its maximum length, the maximum length chord having a mid-point that is spaced away from the rotational axis of the drive shaft.

77. The rotational atherectomy device of claim 76 wherein the eccentric enlarged diameter section has a maximum length chord between about 1.5 mm and about 1.75 mm, and the chord mid-point is spaced away from the rotational axis of the drive shaft by a distance of at least about 0.07 mm.

78. The rotational atherectomy device of claim 76 wherein the eccentric enlarged diameter section has a maximum length chord between about 1.5 mm and about 1.75 mm, and the chord mid-point is spaced away from the rotational axis of the drive shaft by a distance of at least about 0.1 mm.

79. The rotational atherectomy device of claim 76 wherein the eccentric enlarged diameter section has a maximum length chord between about 1.5 mm and about 1.75 mm, and the chord mid-point is spaced away from the rotational axis of the drive shaft by a distance of at least about 0.13 mm.

80. The rotational atherectomy device of claim 76 wherein the eccentric enlarged diameter section has a maximum length chord between about 1.75 mm and about 2.0 mm, and the chord mid-point is spaced away from the rotational axis of the drive shaft by a distance of at least about 0.15 mm.

81. The rotational atherectomy device of claim 76 wherein the eccentric enlarged diameter section has a maximum length chord between about 1.75 mm and about 2.0 mm, and the chord mid-point is spaced away from the rotational axis of the drive shaft by a distance of at least about 0.2 mm.

82. The rotational atherectomy device of claim 76 wherein the eccentric enlarged diameter section has a maximum length chord between about 1.75 mm and about 2.0 mm, and the chord mid-point is spaced away from the rotational axis of the drive shaft by a distance of at least about 0.25 mm.

83. The rotational atherectomy device of claim 76 wherein the eccentric enlarged diameter section has a maximum length chord of at least about 2.0 mm, and the chord mid-point is spaced away from the rotational axis of the drive shaft by a distance of at least about 0.3 mm.

84. The rotational atherectomy device of claim 76 wherein the eccentric enlarged diameter section has a maximum length chord of at least about 2.0 mm, and the chord mid-point is spaced away from the rotational axis of the drive shaft by a distance of at least about 0.35 mm.

85. The rotational atherectomy device of claim 76 wherein the eccentric enlarged diameter section has a maximum length chord of at least about 2.0 mm, and the chord mid-point is spaced away from the rotational axis of the drive shaft by a distance of at least about 0.4 mm.

86. The rotational atherectomy device of claim 1 or 2 wherein the enlarged diameter section has a maximum diameter between about 1.5 mm and about 1.75 mm, and is sufficiently eccentric that, when rotated over a stationary guide wire at a rotational speed of not more than 60 rpm, at least a portion of its tissue removing surface rotates through a path having a diameter at least about 10% larger than the maximum nominal diameter of the eccentric enlarged diameter section.

87. The rotational atherectomy device of claim 1 or 2 wherein the enlarged diameter section has a maximum diameter between about 1.5 mm and about 1.75 mm, and is sufficiently eccentric that, when rotated over a stationary guide wire at a rotational speed of not more than 60 rpm, at least a portion of its tissue removing surface rotates through a path having a diameter at least about 15% larger than the maximum nominal diameter of the eccentric enlarged diameter section.

88. The rotational atherectomy device of claim 1 or 2 wherein the enlarged diameter section has a maximum diameter between about 1.5 mm and about 1.75 mm, and is sufficiently eccentric that, when rotated over a stationary guide wire at a rotational speed of not more than 60 rpm, at least a portion of its tissue removing surface rotates through a path having a diameter at least about 20% larger than the maximum nominal diameter of the eccentric enlarged diameter section.

89. The rotational atherectomy device of claim 1 or 2 wherein the enlarged diameter section has a maximum diameter between about 1.75 mm and about 2.0 mm, and is sufficiently eccentric that, when rotated over a stationary guide wire at a rotational speed of not more than 60 rpm, at least a portion of its tissue removing surface rotates through a path having a diameter at least about 20% larger than the maximum nominal diameter of the eccentric enlarged diameter section.

90. The rotational atherectomy device of claim 1 or 2 wherein the enlarged diameter section has a maximum diameter between about 1.75 mm and about 2.0 mm, and is sufficiently eccentric that, when rotated over a stationary guide wire at a rotational speed of not more than 60 rpm, at least a portion of its tissue removing surface rotates through a path having a diameter at least about 25% larger than the maximum nominal diameter of the eccentric enlarged diameter section.

91. The rotational atherectomy device of claim 1 or 2 wherein the enlarged diameter section has a maximum diameter between about 1.75 mm and about 2.0 mm, and is sufficiently eccentric that, when rotated over a stationary guide wire at a rotational speed of not more than 60 rpm, at least a portion of its tissue removing surface rotates through a path having a diameter at least about 30% larger than the maximum nominal diameter of the eccentric enlarged diameter section.

92. The rotational atherectomy device of claim 1 or 2 wherein the enlarged diameter section has a maximum diameter of at least about 2.0 mm, and is sufficiently eccentric that, when rotated over a stationary guide wire at a rotational speed of not more than 60 rpm, at least a portion of its tissue removing surface rotates through a path having a diameter at least about 30% larger than the maximum nominal diameter of the eccentric enlarged diameter section.

93. The rotational atherectomy device of claim 1 or 2 wherein the enlarged diameter section has a maximum diameter of at least about 2.0 mm, and is sufficiently eccentric that, when rotated over a stationary guide wire at a rotational speed of not more than 60 rpm, at least a portion of its tissue removing surface rotates through a path having a diameter at least about 40% larger than the maximum nominal diameter of the eccentric enlarged diameter section.

94. The rotational atherectomy device of claim 1 or 2 wherein the enlarged diameter section is sufficiently eccentric that, when rotated over a stationary guide wire at a speed between about 20,000 rpm and about 200,000 rpm, at least a portion of its tissue removing surface rotates through a path having a diameter at least about 30% larger than the maximum nominal diameter of the eccentric enlarged diameter section.

95. The rotational atherectomy device of claim 1 or 2 wherein the enlarged diameter section is sufficiently eccentric that, when rotated over a stationary guide wire at a speed between about 20,000 rpm and about 200,000 rpm, at least a portion of its tissue removing surface rotates through a path having a diameter at least about 50% larger than the maximum nominal diameter of the eccentric enlarged diameter section.

96. The rotational atherectomy device of claim 1 or 2 wherein the enlarged diameter section is sufficiently eccentric that, when rotated over a stationary guide wire at a speed between about 20,000 rpm and about 200,000 rpm, at least a portion of its tissue removing surface rotates through a path having a diameter at least about 70% larger than the maximum nominal diameter of the eccentric enlarged diameter section.

97. The atherectomy device of claim 1 or 2 wherein the elongated drive shaft has proximal and distal sections, located proximally and distally of the eccentric enlarged diameter section of the drive shaft.

98. The atherectomy device of claim 97 wherein the proximal section of the elongated drive shaft has a generally constant inner diameter along substantially its entire length, the distal section of the elongated drive shaft also having a generally constant inner diameter along substantially its entire length, the inner diameter of the distal section of the drive shaft being less than the inner diameter of the proximal section of the drive shaft, substantially the entire distal section of the drive shaft functioning as a bearing to facilitate rotation of the drive shaft around the guide wire.

99. The atherectomy device of claim 97 wherein the proximal section of the elongated drive shaft has a generally constant inner diameter along substantially its entire length except for a reduced inner diameter segment located near the eccentric enlarged diameter section, the reduced inner diameter segment functioning as a bearing to facilitate smooth rotation of the drive shaft around the guide wire.

100. The atherectomy device of claim 99 wherein substantially the entire length of the distal section of the elongated drive shaft has an inner diameter which is about equal to the inner diameter of the reduced inner diameter segment of the proximal section of the drive shaft, whereby substantially the entire distal section of the drive shaft functioning as a bearing to facilitate rotation of the drive shaft around the guide wire.

101. The atherectomy device of claim 97 wherein the distal section of the elongated drive shaft has a generally constant inner diameter along substantially its entire length except for a reduced inner diameter segment located near the eccentric enlarged diameter section, the reduced inner diameter segment functioning as a bearing to facilitate smooth rotation of the drive shaft around the guide wire.

102. The rotational atherectomy device of claim 1 wherein the elongated drive shaft includes two or more reduced inner diameter segments, at least one being located distally of the eccentric enlarged diameter section, and at least one being located proximally of the eccentric enlarged diameter section, the reduced diameter segments of the drive shaft functioning as bearings to facilitate smooth rotation of the drive shaft around the guide wire.

103. The rotational atherectomy device of claim 1 or 2 wherein the tissue removing surface is an abrasive surface.

104. A rotational atherectomy device for opening a stenosis in an artery having a given diameter, comprising a guide wire having a maximum diameter less than the diameter of the artery, and a flexible, elongated, rotatable drive shaft advanceable over the guide wire, the drive shaft having a rotational axis and a tissue removing section having a center of mass spaced radially from the rotational axis of the drive shaft, the drive shaft, including its tissue removing section, being comprised of one or more helically wound wires.

105. A rotational atherectomy device for opening a stenosis in an artery having a given diameter, comprising a guide wire having a maximum diameter less than the diameter of the artery, and a flexible, elongated, rotatable drive shaft advanceable over the guide wire, the drive shaft having an axis about which the drive shaft is rotated, the drive shaft including a tissue removing section having a shape such that a face of a transverse cross-section of the tissue removing section has a geometric center which is spaced radially away from the rotational axis of the drive shaft, the drive shaft, including its tissue removing section, being comprised of one or more helically wound wires.

106. A method of removing stenotic tissue from a stenotic lesion in an artery, comprising:

providing a flexible, elongated, rotatable drive shaft having an eccentric enlarged diameter section with a nominal diameter, at least part of the eccentric enlarged diameter section having a tissue removing surface, the drive shaft, including its eccentric enlarged diameter section, being comprised of one or more helically wound wires, at least some adjacent wire turns of the eccentric enlarged diameter section being not secured with respect to each other, thereby permitting the eccentric enlarged diameter section to be deformed by centrifugal force;

advancing the rotatable drive shaft over the guide wire to a location adjacent to the stenotic tissue;

rotating the drive shaft at a speed sufficient to deform the eccentric enlarged diameter section by centrifugal force to a shape more eccentric than its at-rest shape; and while rotating the drive shaft at such speed, moving the eccentric enlarged diameter section across the stenotic lesion, thereby opening the stenotic lesion to a diameter larger than the nominal diameter of the eccentric enlarged diameter section.

* * * * *